United States Patent [19]

Jacobs et al.

[11] Patent Number: 5,550,136
[45] Date of Patent: Aug. 27, 1996

[54] METHANOANTHRANCENYL PIPERIDYL ANTIPSYCHOTICS

[75] Inventors: Robert T. Jacobs; Cyrus J. Ohnmacht; Diane A. Trainor, all of Wilmington, Del.

[73] Assignee: Zeneca Limited, London, England

[21] Appl. No.: 374,053

[22] Filed: Jan. 19, 1995

Related U.S. Application Data

[62] Division of Ser. No. 927,685, Aug. 6, 1992, Pat. No. 5,399,568.

[30] Foreign Application Priority Data

Aug. 15, 1991 [GB] United Kingdom .................. 9117644
Apr. 7, 1992 [GB] United Kingdom .................. 9207539

[51] Int. Cl.$^6$ ....................... C07D 401/06; A61K 34/445
[52] U.S. Cl. ................... 514/322; 514/316; 514/319; 514/320; 514/325; 546/191; 546/199; 546/203; 546/207; 546/209; 546/210; 546/213; 546/214
[58] Field of Search ....................... 546/146, 149, 546/152, 168, 193, 194, 203, 191, 207, 209, 210, 213, 214, 199; 514/307, 311, 316, 317, 318, 319, 320, 322, 325, 326

[56] References Cited

U.S. PATENT DOCUMENTS

| | | | |
|---|---|---|---|
| 3,399,201 | 8/1968 | Schmidt et al. | 544/380 |
| 3,422,106 | 1/1969 | Boissier et al. | 544/380 |
| 3,455,928 | 7/1969 | Schmidt et al. | 544/380 |
| 3,489,799 | 1/1970 | Schmidt et al. | 564/219 |
| 3,632,653 | 1/1972 | Schmidt et al. | 568/439 |
| 3,706,765 | 12/1972 | Wilhelm et al. | 564/219 |
| 3,778,467 | 12/1973 | Wilhelm et al. | 560/250 |
| 3,870,796 | 3/1975 | Hunger et al. | 514/655 |
| 4,017,542 | 4/1977 | Wilhelm et al. | 546/195 |
| 4,045,560 | 8/1977 | Sunagawa et al. | 514/239 |
| 4,045,580 | 8/1977 | Wilhelm et al. | 514/653 |
| 4,153,629 | 5/1979 | Tanida et al. | 546/195 |
| 4,216,231 | 8/1980 | Tanida et al. | 514/644 |
| 4,224,344 | 9/1980 | Sunagawa et al. | 514/649 |
| 4,318,926 | 5/1982 | Schmidt-Ruppin et al. | 514/654 |
| 4,358,620 | 11/1982 | Sunagawa et al. | 568/439 |
| 5,226,570 | 11/1993 | Yee et al. | 514/23702 |

FOREIGN PATENT DOCUMENTS

| | | |
|---|---|---|
| 610863 | 10/1961 | Belgium . |
| 843875 | 7/1975 | Belgium . |
| 918677 | 1/1973 | Canada . |
| 2556143 | 12/1974 | Germany . |
| 52068-170 | 12/1975 | Japan . |
| 52122-358 | 4/1976 | Japan . |
| 53005-175 | 5/1976 | Japan . |
| 52007953 | 1/1977 | Japan . |
| 52122358 | 10/1977 | Japan . |
| 6907455 | 5/1965 | Netherlands . |
| 533079 | 3/1973 | Switzerland . |

*Primary Examiner*—Ceila Chang
*Attorney, Agent, or Firm*—Michael D. Alexander; Ruth H. Newtson

[57] ABSTRACT

Compounds of formula I

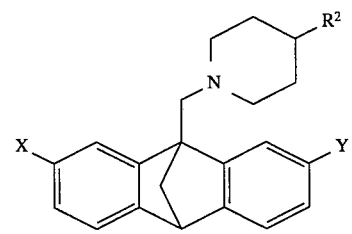

wherein X and Y are H or halo;
$R^2$ is: [structures Ia, Ib or Ic;]

Ia:

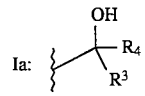

-continued

Ib:

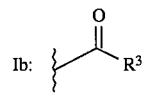

Ic:

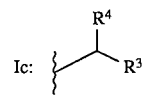

$R^3$ is selected from unsubstituted or substituted alkyl, aryl or heteroaryl groups;
$R^4$ is selected from H or (C1–6)alkyl,
and pharmaceutically acceptable salts thereof, useful in the treatment of neuropsychiatric disoders such as psychoses; pharmaceutical compositions comprising a compound of formula I and a pharmaceutically acceptable diluent or carrier; and methods of treating neuropschiatric disorders comprising administering to a mammal (including man) in need of such treatment an effective mount of a compound of formula I, or a pharmaceutically acceptable salt thereof.

6 Claims, No Drawings

METHANOANTHRANCENYL PIPERIDYL ANTIPSYCHOTICS

This is a divisional of application Ser. No. 07/927,685 filed on Aug. 6, 1992, now U.S. Pat. No. 5,399,568.

This invention relates to methanoanthracene compounds useful because they have been determined to be antagonists of dopamine at $D_2$ receptors. The compounds exhibit antidopaminergic activity and are useful in alleviating neuropsychiatric disorders such as psychoses, as antipsychotics, and as neuroleptics. In addition, as $D_2$ antagonists, compounds according to the invention may also be useful in the amelioration of other disorders in which dopaminergic activity has been implicated, for example gastrointestinal disorders, emesis, and tardive dyskinesia.

According to the invention there is provided a compound of formula I (formula set out, together with other formulae referred to by Roman Numerals, on pages following the Examples), or a pharmaceutically acceptable salt thereof, wherein X and Y are independently selected from hydrogen and halo;

R is selected from the structures shown as formulae Ia, Ib, and Ic, wherein:

R3 is selected from (3–6C)cycloalkyl;

(1 . 6C)alkyl;

phenyl and naphthyl each of which may bear 0–3 substituents independently selected from the group consisting of (1–6C)alkyl, (1–6C)alkoxy, hydroxy, halo, cyano, nitro, benzoyl, di(1–6C)alkylamino(1–6C)alkyl aminosulfonyl having the formula $SO_2NR^aR^b$ and aminocarbonyl having the formula $CONR^cR^d$ wherein $R^a$ Rb, $R^c$ and $R^d$ are independently selected from hydrogen and (1–6C)alkyl, or wherein $R^a$ and $R^b$, and $R^c$ and $R^d$, together with the nitrogen atom to which each is attached, form a 5-membered or 6-membered heterocyclic ring in which the said nitrogen is the only heteroatom;

five- and six-membered heteroaryl rings containing from 1–3 heteroatoms selected from nitrogen, oxygen, and sulfur, and benz derivatives thereof, which may bear 0–2 substitutents selected from hydroxy, (1–6C)alkyl, (1–6C)alkoxy, (1–6C)hydroxyalkyl, phenyl, chloro, and fluoro; and R4 is selected from hydrogen and (1–6C)alkyl.

The invention further provides a pharmaceutical composition suitable for the treatment of neurological disorders, comprising a compound of formula I, or a pharmaceutically acceptable salt thereof, and a pharmaceutically acceptable diluent or carrier.

The invention further provides a method for the treatment of neuropsychiatric disorders, comprising administering to a mammal in need of such treatment an effective amount of a compound of formula I as defined above, or a pharmaceutically acceptable salt thereof.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

It will be appreciated by those skilled in the art that compounds of formula I may contain an asymmetrically substituted carbon and/or sulfur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of psychoses, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of psychoses by the standard tests described hereinafter.

Particular values of (3–6C)cycloalkyl include cyclopropyl, cyclobutyl, cyclopentyl, and cyclohexyl.

Particular values of (1–6C)alkyl include methyl, ethyl, propyl, isopropyl, butyl, isobutyl, sec-butyl, tert-butyl, pentyl, isopentyl, neopentyl, hexyl, and isohexyl.

Particular values of (1–6C)alkoxy include methoxy, ethoxy, propoxy, isopropoxy, butoxy, isobutoxy, sec-butoxy, tert-butoxy, pentoxy, isopentoxy, neopentoxy, hexoxy, and isohexoxy.

Particular values of five- and six-membered heteroaryl rings containing from 1–3 heteroatoms selected from nitrogen, oxygen, and sulfur include 2, 3-, and 4-pyridyl, 2-pyrazinyl, 2- and 4-pyrimidinyl, 3- and 4-pyridazinyl, 3-, 4- and 5-isothiazolyl, 2-, 4- and 5-oxazolyl, 2-, 4- and 5-thiazolyl, 4- and 5-oxadiazolyl, 2- and 3-furyl, 2-, 4-, and 5-imidazolyl, and 2- and 3-thienyl. The preceding rings may be optionally substituted with substituents as previously defined.

Particular values of benz derivatives of five- and six membered heteroaryl rings include the various values of quinolyl and isoquinolyl, optionally substituted as defined above.

Particular values of (1–6C)hydroxyalkyl include hydroxymethyl, 1-hydroxyethyl, 2-hydroxyethyl, 1-hydroxypropyl, 2-hydroxypropyl, 3-hydroxypropyl, 1-hydroxyprop-2-yl, 1-hydroxybutyl, 2-hydroxybutyl, and 3-hydroxybutyl.

Particular values of $R^3$ include phenyl and naphthyl each of which may bear 0–2 substituents independently selected from the group consisting of (1–6C)alkyl, (1–6C)alkoxy, halo, aminosulfonyl having the formula $SO_2NR^aR^b$ wherein $R^a$ and $R^b$ are independently selected from hydrogen and (1–6C)alkyl, aminocarbonyl having the formula $CONR^cR^d$ wherein $R^c$ and $R^d$ are independently selected from hydrogen and (1–6C)alkyl; and the particular values given above for five- and six-membered heteroaryl rings (which can be optionally substituted as previously defined).

Particular values of $R^4$ include hydrogen and values of (1–3C)alkyl, including methyl, ethyl, propyl, and isopropyl.

More particular values of (1–6C)alkyl include values of (1–3C)alkyl, including methyl, ethyl, propyl, and isopropyl.

More particular values of (1–6C)alkoxy include values of (1–3C)alkoxy, including methoxy, ethoxy, propoxy, and isopropoxy.

More particular values of five- and six-membered heteroaryl rings containing from 1–3 heteroatoms selected from nitrogen, oxygen, and sulfur include 2, 3-, and 4-pyridyl, 3-, 4- and 5-isothiazolyl, 2-, 4- and 5-thiazolyl, and 2- and 4-imidazolyl.

More particular values of benz derivatives of 5- and 6-membered heteroaryl rings include 4-isoquinolyl and 3-quinolyl.

More particular values of (1–6C)hydroxyalkyl include values of (1–3C)hydroxyalkyl, including hydroxymethyl, 1-hydroxyethyl, 2-hydroxyethyl, 1-hydroxypropyl, 2-hydroxypropyl, and 3-hydroxypropyl.

More particular values of $R^3$ include 3-(1–3C)alkylphenyl, 2-(1–3C)alkoxyphenyl, 3-(1–3C)alkoxyphenyl, 3-(1–3C)alkylnaphthyl, 2-(1–3C)alkoxynaphthyl, 3-(1–3C)alkoxynaphthyl, 2-imidazolyl, 5-imidazolyl, 5-thiazolyl, 2-pyridyl, 3-pyridyl, and 2-hydroxy-3-pyridyl.

Preferred compounds of formula I include compounds wherein X and Y are independently selected from hydrogen and chloro, and wherein (a) when $R^2$ has formula Ia, $R^3$ is selected from 2-pyridyl and 3-pyridyl and $R^4$ is selected from hydrogen and methyl;

(b) when $R^2$ has formula Ib, $R^3$ is 3-pyridyl, (c) when $R^2$ has formula Ic, $R^3$ is 2-hydroxy-3-pyridyl and $R^4$ is hydrogen.

Preferred compounds include:

R-1-[1-((9S,10S)-2-Chloro-9,10-dihydro-9,10-methanoanthracen-9-ylmethyl)-4 -piperidyl]-1-(3-pyridyl)methanol;

S-1-[1-((9S,10S)-2-Chloro-9,10-dihydro-9,10-methanoanthracen-9-ylmethyl)-4 -piperidyl]-1-(3-pyridyl)methanol;

(R,S)-1-[1-(9RS,10RS)-(2-Chloro-9,10-dihydro-9,10-methananthracen-9-ylmethyl)-4 -piperidyl]-1-(3-pyridyl)methanol 1-((9S,10S)-2-Chloro-9,10-dihydro-9,10-methanoanthracen-9-ylmethyl)-4-(2-hydroxy- 3-pyridylmethyl)piperidine:

1-((9RS,10RS)-2-Chloro-9,10-dihydro-9,10-methanoanthracen-9-ylmethyl)-4-(2-hydroxy-3 -pyridylmethyl)piperidine.

When X is chloro and Y is hydrogen, in general, 9S,10S stereochemistry is preferred. In this case, stereochemistry can be determined by coupling an acid chloride of formula VII (G=chloro) with a chiral compound, such as an oxazolidinone of formula VIII, to yield two diastereomers. Separation and recrystallization of the diastereomers followed by X-ray structure determination provides absolute stereochemistry at the 9 and 10 positions.

A compound of formula I can be made by processes which include processes known in the chemical arts for the production of structurally analogous compounds. Such processes for the manufacture of an amide of formula I as defined above are provided as further features of the invention together with chemical intermediates involved therein, and are illustrated by the following procedures in which the meanings of generic radicals are as given above unless otherwise qualified. Such a process can be effected, generally,:

(a) when R2 has formula Ia, by reducing a corresponding amide of formula II. Suitable reducing agents include lithium aluminum hydride and borane-dimethylsulfide complex; The reaction can be conducted in an appropriate solvent such as tetrahydrofuran and at a temperature of room temperature to 65° C.

(b) when $R^2$ has formula Ia and $R^4$ is hydrogen, by treating a corresponding aldehyde of formula III with a corresponding alkyllithium compound of formula $R^3Li$. The reaction can be conducted in a suitable solvent such as tetrahydrofuran and at a temperature of from about −78° C. to about room temperature.

(c) when $R^2$ has formula Ia and $R^4$ is hydrogen, by treating a corresponding aldehyde of formula III with a magnesium halide (i.e., a Grignard agent) of formula $R^3MgZ$ wherein Z is a halo group, for example chloro or bromo; The reaction can be conducted in a suitable solvent such as tetrahydrofuran and at a temperature of from about −78° C. to about room temperature.

(d) when $R^2$ has formula Ia and $R^4$ is (1–6C)alkyl, by treating a ketone of formula IV with a corresponding alkylmagnesium halide of formula $R^4MgZ$ wherein Z is a halo group, for example chloro or bromo; The reaction can be conducted in a suitable solvent such as tetrahydrofuran and at a temperature of from about −78° C. to about room temperature.

(e) when $R^2$ has formula Ia and $R^4$ is (1–6C)alkyl, by treating a ketone of formula IV with a corresponding alkyllithium compound of formula $R^4Li$; The reaction can be conducted in a suitable solvent such as tetrahydrofuran and at a temperature of from about −78° C. to about room temperature.

(f) when $R^2$ has formula Ib, by oxidizing a corresponding alcohol of formula V. The desired product then corresponds to a ketone of formula IV. Suitable oxidizing agents include the combination of oxalyl chloride and dimethylsulfoxide (DMSO) in the presence of a base such as a trialkylamine (for example triethylamine, $Et_3N$). The reaction can be conducted in an appropriate solvent such as methylene chloride and at a temperature in the range of −78° C. to room temperature.

(g) when $R^2$ has formula Ic, by reducing a corresponding amide of formula VI, with a suitable reducing agent such as lithium aluminum hydride, boron trifluoride-diethyl ether complex, or borane-dimethylsulfide complex; The reaction can be conducted in an appropriate solvent such as tetrahydrofuran and at a temperature of room temperature to 65° C.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples. In the discussion which follows and the reaction Schemes pertaining thereto, standard chemical abbreviations and acronyms have employed, including: "Ac" for acetyl; "Et" for ethyl; "THF" for tetrahydrofuran; "Bu" for tert-butyl; "RT" for room temperature; "DMSO" for dimethylsulfoxide; "Me" for methyl; and "Ph" for phenyl. The variable "Z" is employed to refer to halo substituents (such as chloro) in Grignard agents.

A common intermediate for making compounds according to the invention is an acid (G is hydroxyl) or acid halide (G is a halo group such as chloro) of formula VII. This intermediate can be made as illustrated in Scheme I (set out, together with other schemes referred to herein, on pages following the Examples and formulae). An anthraquinone of formula 10 can be reduced to the corresponding anthracene of formula 12 using zinc and ammonia. Anthracene 12 can then be converted to the corresponding 9-aldehyde 14 using phosphorus oxytrichloride and N-methylformanilide. Reaction of aldehyde 14 with vinyl acetate (Diels-Alder reaction) affords the bridged compound 16 which can then be oxidized with chromium trioxide (in the presence of sulfuric acid) to the corresponding acid 18. Acid 18 can then be successively treated with thionyl chloride (in, for example, toluene) to make the corresponding 9-acid chloride, followed by sodium azide (in, for example, a mixture of rarer and acetone) to make the corresponding 9-acyl azide, followed by heating (in, for example, toluene) to effect rearrangement to the corresponding isocyanate, followed by treatment with an alkali metal hydroxide (in an alcohol such as ethanol) to cleave the acetyl group to hydroxy and hydrolyze the isocyanate to amino, thereby yielding the 9-amine 20.

Amine 20 can then be treated with an alkali metal (for example, sodium) nitrite (in, for example, acetic acid) to effect a ring contraction and thereby yield the 9-aldehyde of formula 22. Aldehyde 22 can be oxidized with chromium trioxide in the presence of sulfuric acid to yield the corresponding 9-acid of formula 24 (corresponding to the acid of formula VII, G=hydroxyl). The corresponding 9-acid chloride can be obtained by treating acid 24 with thionyl chloride.

It is noted that if a 2,7-dihalo substituted methanoanthracene is desired, it can be prepared (as exemplified in co-pending application D36501, filed on even date herewith and incorporated by reference) starting with an (unresolved) acid 24 which is mono-substituted at the 2-position with a desired halo (e.g., chloro) substituent, although in the discussion which follows it is to be understood that an optically enriched isomer (such as 26) can be employed if a corresponding optically enriched dihalo substituted product is desired. Acid 24 can be reacted with thionyl chloride to make the corresponding 9-acid chloride followed by the addition of a lower over alcohol (such as methanol or ethanol) to afford a lover 9-alkyl ester. The 2-halo ester can then be nitrated at the 7- position by reaction with a suitable nitrating agent such as a combination of trifluoroacetic anhydride and ammonium nitrate under an inert gas (e.g, nitrogen) atmosphere. This reaction will generally produce a mixture of 2-halo-6-nitro and 2-halo-7-nitro positional isomers which can be separated by conventional separation techniques such as recrystallization or flash chromatography over silica gel. The 2-halo-7-nitro isomer can be reduced to the corresponding 7-amino-2-halo compound by a suitable reducing agent such as stannous chloride, and the 7-amino-2-halide thus obtained can be converted to the corresponding 2,7-dihalo alkyl ester by reaction with a diazotizing agent such as tert-butyl nitrite followed by treatment with a cupric halide such as cupric chloride or cupric bromide. The ester can then be cleaved with a suitable base (such as an alkali metal hydroxide) to afford the corresponding 2,7-dihalo substituted acid.

As indicated by the R,S notation in Scheme I, acid 24 is racemic. Resolution of racemic acid 24 can be accomplished by fractional crystallization of diastereomeric salts, formed by addition of a chiral amine such as (+)-pseudoephedrine, from a suitable solvent such as ethanol to yield optically enriched acid 26. Treatment of 26 with thionyl chloride yields a correspondingly optically enriched acid chloride. Optically enriched intermediates can be employed in chiral syntheses to make optically enriched compounds according to the invention.

An amide of formula II wherein $R^2$ has formula Ia and $R^4$ is hydrogen can be made, as illustrated in Scheme IIa, by treating a compound of formula 44 with an acid halide of formula VII (i.e., wherein G is a halo group such as chloro).

A compound of formula 44 can be made as also illustrated in Scheme IIa. An alkyl ester of formula 30 (the ethyl ester being shown for purposes of illustration) can be reduced to the corresponding alcohol 32 by refluxing with lithium aluminum hydride in a solvent such as THF. A protective group (such as a tert-butylcarbamoyl group, $^t$BuOCO) can then be reacted onto the piperidino nitrogen by reacting alcohol 32 with an acid anhydride such as di-tert-butyl dicarbonate to make the corresponding protected alcohol of formula 34. Protected alcohol 34 can then be oxidized/ dehydrogenated to the corresponding aldehyde 36 with oxalyl chloride and DMSO in the presence of a base such as a trialkylamine (for example triethylamine), in an appropriate solvent such as methylene chloride and at a temperature in the range of −78° C. to room temperature. (Alternatively, aldehyde 36 can be made by treating protected alcohol 34 with an oxidizing agent such as pyridinium chlorochromate in an appropriate solvent such as methylene chloride and at a temperature in the range of 0° C. to room temperature.) Aldehyde 36 can be reacted with a Grignard reagent of formula $R^3MgZ$ or an alkyllithium compound of formula $R^3Li$ in an appropriate solvent such as THF and at a temperature in the range of −78° C. to room temperature, thereby making a (racemic) alcohol of formula 38. Racemic alcohol 38 can be oxidized with oxalyl chloride and DMSO as described above, or by using manganese dioxide in a suitable solvent such as methylene chloride at room temperature, thereby yielding ketone 40. Ketone 40 can be asymmetrically reduced with (+)-β-chlorodiisopinocampheylborane as described by Brown et al, J. Org. Chem., 50, 5446–5448 (1985), in a solvent such as terahydrofuran and at a temperature of −23° C. to room temperature, or with borane-dimethylsulfide complex in the presence of a chiral oxazaborolidine catalyst such as described by Corey et al, J. Am. Chem. Soc., 109, 7925–7926 (1987), to yield the (optically enriched) alcohol of formula 42a (or the optical isomer 42b) and then deprotected by cleaving the tert-butylcarbamoyl group with acid (for example, trifluoroacetic acid) to yield the correspondingly enriched desired compound of formula 44. Using an optically enriched compound of formula 44 affords a correspondingly enriched amide intermediate of formula II and an enriched final compound of formula I.

An alternative preparation of a compound of formula 44 is also illustrated in Scheme IIb. The piperidino nitrogen of acid 50 can be protected with a protective group such as tert-butylcarbamoyl to make the protected acid of formula 52. Protected acid 52 can then be condensed with N,O-dimethylhydroxylamine hydrochloride in the presence of activators such as 4-dimethylaminopyridine (DMAP) and 1-(3-dimethylaminopropyl)-3-ethylcarbodiimide (WSCDI) in an appropriate solvent such as methylene chloride and at a temperature in the range of 0° C. to room temperature to yield the corresponding N-methoxyamide 54. N-methoxyamide 54 can be reacted with a Grignard reagent of formula $R^3MgZ$ or an alkyllithium compound of formula $R^3Li$ in an appropriate solvent such as tetrahydrofuran and at a temperature in the range of −78° C. to room temperature, thereby making a ketone of formula 40. Ketone 40 can be reduced with a reducing agent such as sodium borohydride in an appropriate solvent such as methanol to give (racemic) alcohol 38. The protective tert-butylcarbamoyl group can then be cleaved by treating alcohol 38 with an acid, for example trifluoroacetic acid, thereby yielding the desired product (as a racemate) 44.

As also shown in Scheme IIb, resolution of racemic alcohol 44 can be accomplished by fractional crystallization of diastereomeric salts, formed by addition of a chiral carboxylic acid, such as dibenzoyl-L-tartaric acid, from a suitable solvent such as ethanol to yield optically enriched compound 44a. Reaction of optically enriched compound 44a with an acid chloride of formula VII yields a correspondingly enriched compound of formula I.

An amide of formula II wherein R2 has formula Ia and R4 is (1–6C) alkyl can be made, as illustrated in Scheme IIc, by treating a compound of formula 68 with an acid halide of formula VII (i.e., wherein G is a halo group such as chloro).

A compound of formula 68 can be made as also illustrated in Scheme IIc. The piperidino nitrogen of acid 50 can be protected with a protective group such as benzyloxycarbonyl to make the protected acid of formula 60. Protected acid 60 can then be condensed with N,O-dimethylhydroxylamine hydrochloride in the presence of activators such as 4-dimethylaminopyridine (DMAP) and 1-(3-dimethylaminopropyl)-3-ethylcarbodiimide (WSCDI) in an appropriate solvent such as methylene chloride and at a temperature in the range of 0° C. to room temperature to yield the corresponding N-methoxyamide 62. N-Methoxyamide 62 can be reacted with a Grignard reagent of formula $R^3MgZ$ or an alkyllithium compound of formula $R^3Li$ in an appropriate solvent such as THF and at a temperature in the range of −78° C. to room temperature, thereby making a ketone of formula 64. Ketone 64 can be reacted with a Grignard reagent of formula $R^4MgZ$ or an alkyllithium compound of formula $R^4Li$ in an appropriate solvent such as THF and at a temperature in the range of −78° C. to room temperature, thereby making a (racemic) alcohol of formula 66, and then deprotected by hydrogenation in the presence of a hydrogenation catalyst such as palladium on carbon (Pd-C), at a hydrogen pressure of, for example, 50 psi in a suitable solvent such as ethanol, and at a temperature in the range of room temperature to 50° C. to make the (racemic) alcohol of formula 68.

As also shown in Scheme IIc, resolution of racemic alcohol 68 can be accomplished by fractional crystallization of diastereomeric salts, formed by addition of a chiral carboxylic acid, such as dibenzoyl-L-tartaric acid, from a suitable solvent such as ethanol to yield optically enriched compound 68a. Reaction of optically enriched compound 68a with an acid halide of formula Vll yields a correspondingly enriched amide of formula II and (following reduction) an enriched compound of formula I.

An aldehyde of formula III can be made as illustrated Scheme III. An acid of formula Vll (G=hydroxyl) can be treated thionyl chloride to convert it to the corresponding acid chloride (G=Cl) of formula VII followed by treatment with an alkyl ester 70 (the ethyl ester being shown for illustration) to make the corresponding amide of formula 72. Amide 72 can be treated lithium aluminum hydride at reflux in an appropriate solvent such as THF to effect reduction of the amide carbonyl to a methylene group and of the ester moiety to the corresponding alcohol, thereby yielding a compound of formula 74. Treatment of 74 with oxalyl chloride and DMSO followed by treatment with a base such as a trialkylamine (for example, triethylamine) in an appropriate solvent such as methylene chloride and at a temperature of −78° C. to room temperature yields the desired aldehyde III.

As also shown in Scheme III, to make a compound of formula I wherein $R^2$ has formula 1b (corresponding to a ketone of formula IV), an aldehyde of formula III can first be reacted with an alkyllithium compound of formula $R^3Li$ or a Grignard agent of formula $R^3MgZ$, as previously described, thereby yielding a compound of formula V (corresponding to a compound of the invention having formula I wherein $R^2$ has formula Ia and $R^4$ is hydrogen). The compound of formula V can be oxidized with a combination of oxalyl chloride and dimethylsulfoxide in the presence of a trialkylamine, as previously described, thereby oxidizing the alcohol moiety to oxo to yield the desired ketone of formula IV.

As also shown in Scheme III, a compound of formula I wherein $R^2$ has formula Ia and $R^4$ is (1–6C)alkyl can be made by reacting a ketone of formula IV with a corresponding alkyllithium compound of formula (1–6C)alkylLi or a corresponding alkylmagnesium compound of formula (1–6C)alkylMgZ (Z has the meaning previously noted).

As noted above, an amide having formula VI can be reduced as illustrated an Scheme IV to yield a corresponding compound of formula I wherein $R^2$ has formula Ic. Amide VI can be obtained as also illustrated in Scheme IV and described following.

An alcohol of formula 90 can be treated with an acid anhydride, such as acetic anhydride, in the presence of a base, such as triethylamine, and a catalytic amount of an accelerator, such as 4-dimethylaminopyridine (DMAP), in a suitable solvent such as THF at a temperature in the range 0° C. to room temperature to give the corresponding acetate of formula 92. Acetate 92 can be reduced by the action of a hydrogen transfer agent, such as formic acid or ammonium formate, in the presence of a hydrogenation catalyst, such as palladium on carbon (Pd-C), in a suitable solvent such as methanol and at a temperature in the range of from room temperature to 65° C. to give the protected piperidine derivative 94. Protected piperidine 94 can be deprotected by treatment with an acid, such as trifluoroacetic acid, in a suitable solvent, such as chloroform, at a temperature in the range of 0° C. to room temperature to make the 4-substituted piperidine 96. Treatment of piperidine 96 with an acid chloride of formula VII yields the corresponding amide of formula VI.

It is noted that many of the starting materials for synthetic methods as described above are commercially available and/or widely reported in the scientific literature.

Examples of suitable pharmaceutically acceptable salts are organic acid addition salts formed with acids which form a physiologically acceptable anion, for example, tosylate, methanesulfonate, acetate, tartrate, citrate, succinate, benzoate, ascorbate, α-ketoglutarate, and α-glycerophosphate. Suitable inorganic salts may also be formed such as sulfate, nitrate, and hydrochloride. Pharmaceutically acceptable salts may be obtained using standard procedures yell known in the art, for example by reacting a compound of formula I with a suitable acid affording a physiologically acceptable anion.

When used to treat psychoses, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration. Oral administration is preferred.

The dose of compound of formula I which is administered rill necessarily be varied according to principles yell known in the art taking account of the route of administration, the severity of the psychotic condition, and the size and age of the patient. In general, a compound of formula I will be administered to a warm blooded animal (such as man) so that an effective dose is received, generally a daily dose in the range of about 0.01 to about 40 mg/kg body weight. For example, if the compound is administered intramuscularly, it is administered in the range of about 0.01 to about 10 mg/kg body weight. If it is administered orally, it is administered in the range of about 0.1 to about 40 mg/kg body weight.

It will be apparent to those skilled in the art that a compound of formula I can be co-administered with other therapeutic or prophylactic agents and/or medicaments that are not medically incompatible therewith. Compounds within the scope of the invention do not show any indication of overt toxicity in laboratory test animals at several multiples of the minimum effective dose.

The compounds of Formula I are antagonists of dopamine D-2 receptors, and as such are predicted to be useful as antipsychotic drugs. D-2 antagonism can be shown by standard tests such as antagonism of [$^3$H]-spiperone binding (Test A), and/or antagonism of apomorphine-induced climbing and apomorphine- induced disruption of swimming (Test B).

Test A

The receptor binding assay used to measure affinities of various compounds for the dopamine (DA) D-2 receptor subtype was that described by Saller and Salama in J Pharmacol Exp Ther 236, page 714, 1986.

Specifically, rat striatal membranes were used. Tissue membranes were prepared and washed once in 50 volumes of the appropriate Tris HCl buffer. For the D-2 receptor binding assay, striatal membranes were suspended to a final concentration of 8 mg/ml in 50 mM Tris HCl with 40 nM ketanserin, pH 7.7. Nonspecific binding to D-2 receptors was measured in the presence of 1.0 μM (+)-butaclamol. $IC_{50}$s (drug concentration which produced a 50% displacement) for the displacement of 0.5 nM [$^3$Hi spiperone were determined using at least five concentrations of each drug in triplicate. One-half milliliter of membrane suspension was incubated with the compound of interest or vehicle or nonspecific drug, ligand and appropriate Tris HCl buffer. The final reaction volume totaled 1 ml for each tube and was incubated at 37° C. for 15 min to facilitate binding and ensure equilibrium had been met. A Brandel filtering system equipped with GF/B filters was used to separate bound from free drug. The amount of drug bound to the membranes was assessed using liquid scintillation counting techniques. $IC_{50}$ values were obtained from a least squares regression of a logit-log transformation of the data. Typical values in this test were, for example, 103 nM (nanomolar) for the compound of Example 6, 84 nM for the compound of Example 15, and 15 nM for the compound of Example 21.

Test B

Female Swiss-Webster mice weighing approximately 20 g were deprived of food for approximately 24 h and then dosed orally with various doses of either the vehicle or test agent over a range of doses (N=20 mice per treatment group). Thirty minutes later they were dosed with apomorphine HCl at 1.25 mg/kg, sc, and placed into climbing cages. The climbing cages were 9 cm wide, 15 cm deep and 30 cm high. One wall had 27 horizontal rungs spaced 1 cm apart. Thirteen minutes after apomorphine each mouse was observed continuously for 1 min and the highest and lowest rung reached by its front paws was recorded. The mean of these two scores was used as the score for that mouse. (The highest and lowest scores were 27 and 0, respectively.) Immediately after the 1-min climbing observation period each mouse was placed into a circular swimming tank for 2 min and the number of swims was counted. The height of the tank was 15 cm and the diameter was 28 cm. A circular obstacle measuring 10.5 cm in diameter and having a height of 17 cm was placed into the center of the tank, creating a circular swimming channel 8.75 cm wide. The water level was 5.5 cm and the water was kept at room temperature. Marks were placed on the floor and side of the tank 180 degrees apart. A "swim" was scored each time a mouse swam from one mark to the other. The mice were observed through overhead mirrors and the number of 180 degree swims was recorded for each mouse. Activity in this test was indicated by a decrease in the climbing score accompanied by an increase in the swimming score at a given dose of the test compound. Typical values of minimum effective doses in this test were 10 mg/kg for the compound of Example 6 and 20 mg/kg for each of the compounds of Examples 15 and 21.

In general, compounds were considered active if they provided an $IC_{50}$ value of 500 nM or less in Test A, and/or were active following an oral dose of 40 mg/kg or less in Test B.

The invention will now be illustrated by the following non-limiting examples in which, unless stated otherwise:

(i) temperatures are given in degrees Celsius (C.); operations were carried out at room or ambient temperature, that at a temperature in the range of 18°–25° C.

(ii) evaporation of solvent was carried out using a rotary evaporator under reduced pressure (600–4000 pascals; 4.5–30 mmMg) with a bath temperature of up to 60° C.;

(iii) flash chromatography was carried out on Merck Kieselgel (Art 9385) or Baker Flash silica gel; thin layer chromatography (TLC) was carried out on Analtech 0.25 mm silica gel GHLF plates (Art 21521), obtainable from Analtech, Newark, Del., USA;

(iv) high pressure liquid chromatography (HPLC) for analysis of enantiomeric purity determinations of chiral compounds was carried out on either a 25 cm×4.6 mm Chiralcel¤ OD or a 15 cm×4.6 mm Ultron Ovomucoid column available from JT Baker, Inc.; HPLC analyses for most reactions and final products was carried out on either a 25 cm×4.6 mm Supelcosil¤ LC-8-DB, a 25 cm×4.6 mm Supelcosil¤ LC-18-DB column, available from Supelco, State College, Pa., USA or a 25 cm×4.6 mm Zorbax¤ RX column.

(v) in general, the course of reactions was followed by TLC and/or HPLC and reaction times are given for illustration only;

(vi) melting points are uncorrected and (dec) indicates decomposition; the melting points given are those obtained for the materials prepared as described; polymorphism may result in isolation of materials with different melting points in some preparations;

(vii) all final products were essentially pure by TLC and/or HPLC and had satisfactory nuclear magnetic resonance (NMR) spectra and microanalytical data;

(viii) yields are given for illustration only;

(ix) reduced pressures are given as absolute pressures in pascals (Pa); other pressures are given as gauge pressures in bars;

(x) chemical symbols have their usual meanings; the following abbreviations have also been used: v (volume), w(weight), mp (melting point), L (liters), mL (milliliters), g (grams), mmol (millimoles), mg (milligrams), min (minutes), h (hour); and (xi) solvent ratios are given in volume: volume (v/v) terms.

EXAMPLE 1

R-1-[1-((9S,10S)-2-Chloro-9,10-dihydro-9,10-methanoanthracen-9ylmethyl)-4-piperidyl]-1-(3-pyridyl)methanol.

A solution of a starting crude amide (970 mg, 2.25 mmol) in tetrahydrofuran (30 mL) was treated with boron trifluoride etherate (640 mg, 4.51 mmol) and borane-methyl sulfide (1.13 mL of a 10.0M solution, 11.25 mmol). The resulting mixture was heated to reflux for 16 h, then was quenched by addition of methanol (10 mL) and 1N hydrochloric acid (1 mL). The mixture was heated to reflux for 1 h, then was cooled to room temperature and basified to pH⁻11 by addition of 20% aqueous sodium hydroxide. Evaporation of the mixture afforded a semi-solid residue, which was partitioned between 10% aqueous sodium hydroxide (30 mL) and chloroform (40 mL). The organic extract was washed sequentially with 1N aqueous sodium hydroxide (30 mL) and brine (30 mL). Each aqueous wash was extracted with chloroform (3×30 mL). The organic extracts were combined, dried over potasssium carbonate, filtered and evaporated to leave an off white foam (810 mg). Purification by flash chromatography over silica gel (eluant: 95:5 chloroform/methanol) afforded a white solid (600 mg). A solution of this solid in methanol/ether (1:20, 100 mL) was treated with hydrogen chloride (g) to generate the dihydrochloride salt, which was precipitated from methanol/ diethyl ether (1:20). The salt was dissolved in water (75 mL) and lyophilized to give the title compound (510 mg, 1.02 mmol, 45%) as a white powder mp 220°–225° C. $\alpha_D$ +44.0° (c=0.5, MeOH).

Analysis for $C_{27}H_{27}ClN_2O \cdot 2HCl \cdot 1.1H_2O$: Calculated: C, 61.92; H, 6.00; N, 5.34 Found: C, 61.77; H, 5.80; N, 5.26 $^1$H NMR ($d_6$-DMSO): δ 8.76 (m, 2H, H-C(2"), H-C(6")), 8.32 (d, J=8.0 Hz, 1H, H-C(4")), 7.89 (dd, J=5.6 Hz, 8.0 Hz, 1H, H-C(5")), 7.49 (d, J=1.7 Hz, H-C(1)), 7.33 (m, 3H), 7.00 (m, 3H), 4.63 (d, J=5.1 Hz, CHOH), 4.46 (s, 1H, H-C(]O)), 4.28 (m, 2H, CH$_2$N), 3.45 (m, 2H, ax-H-C(2')), 3.19 (m, 2H, eq-H-C(2')), 2.74 (m, 2H, H-C(11)), 1.91–1.07 (m, 5H, H-C(3), H-C(4)). CIMS: m/z 434 ((M+H+1)$^+$, $^{37}$Cl, 11%), 433 ((M+H)$^+$, $^{37}$Cl, 46%) 432 ((M+H+1)$^+$, $^{35}$Cl, 29%), 431 (M+H)$^+$, $^{35}$Cl, 100%) 413 (19).

The starting crude amide was prepared as follows:

a. R-1-[1-((9S,10S)-2-Chloro-9,10-dihydro-9,10-methanoanthracen-9-ylcarbonyl)-4 -piperidyl]-1-(3-pyridyl)methanol.

A solution of (S,S) chloromethanoanthracene acid (567 mg, 2.09 mmol) in dichloromethane (20 mL) was treated with oxalyl chloride (1.28 g, 10.04 mmol) and N,N-dimethylformamide (10 mg, 0.14 mmol). The resulting solution was warmed to reflux temperature for 30 minutes, then was cooled to room temperature and the excess reagent was evaporated in vacuo. The residue was dissolved in dichloromethane (20 mL), and this solution was added to a stirred, 0° C. solution of piperidin-4-yl-pyridin-3-ylmethanol (390 mg, 2.02 mmol) and triethylamine (937 mg, 9.25 mmol) in dichloromethane (20 mL). The resulting mixture was stirred for 30 minutes at room temperature, then was poured into 1N aqueous sodium hydroxide (20 mL). The organic phase was separated and washed sequentially with 1N aqueous sodium hydroxide (20 mL) and brine (20 mL). The aqueous washes were extracted with dichloromethane (40 mL). The organic extracts were combined, dried over potassium carbonate, filtered and evaporated to leave an off white foam (970 mg). This sample of amide was used directly without purification.

The 2-chloro-9,10-dihydro-9,10-methano-9-anthracenecarboxylic acid was prepared as follows:

b. 2-Chloroanthracene.

A stirred suspension of 2-chloroanthraquinone (1260 g, 5.19 moles) in concentrated ammonium hydroxide (7.5 L) and water (2.5 L) was warmed to 40° C. Zinc dust (845 g, 12.93 moles) was added in one portion, changing the color to deep red. The mixture was stirred for 45 min at 50° C., then cautiously treated with a second portion of zinc dust (845 g). After the addition, the stirred mixture was heated gradually over 3 h to 90° C., then maintained at 90°–95° C. for 2 h (red color dissipated). TLC analysis [silica gel/ hexane:methylene chloride (3:1)] showed complete conversion of the anthraquinone ($R_f$=0.35) to the desired anthracene ($R_f$=0.80). The reaction mixture was stirred overnight as it cooled to room temperature. The cooled mixture was treated with methylene chloride (4 L), stirred for 2 h, then filtered through Celite to remove the excess zinc. The filter cake was washed with methylene chloride (6×1 L). The methylene chloride layer was separated from the aqueous, then treated with 6N hydrochloric acid (3 L) and stirred for 2 h. A first crop of 2-chloroanthracene was collected by filtration and washed with water (4×1 L). Vacuum drying afforded a light yellow crystalline product weighing 804.6 g (mp 220°–221° C.). The methylene chloride portion of the filtrate was concentrated in vacuo to 10% of its original volume. This produced an additional 158.5 g of the desired compound for a total yield of 963.1 g (87.2%). 1H NMR (CDCl3): δ 8.39 (s, 1H), 8.30 (s,1H), 7.96 (s, 4H), 7.49 (s, 2H), 7.36 (d, J=8.7 Hz, 1H).

c. 2-Chloro-9-anthraldehyde.

N-methylformanilide (2.45 kg, 18.12 moles) was treated with phosphorus oxychloride (2.66 kg, 17.35 moles) over a 40 min. period at ambient temperature. The intermediate Vilsmeier complex was stirred for 2 h at room temperature, then treated with 2-chloroanthracene (963 g, 4.53 moles), and o-dichlorobezene (1.0 L). The resulting bright yellow mixture was heated gradually over 1.5 h to 90° C. at which point an exotherm ensued raising the reaction temperature to 115° C. The heat was removed until the exotherm subsided (45 min.), after which time the mixture was heated for 9 h at 90° C., then cooled. TLC analysis [silica gel/ethyl acetate-:hexane (1:4)] showed a small amount of unreacted anthracene ($R_f$=0.90), a small amount of the 3-chloro isomer ($R_f$=0.65), and the 2-chloro isomer ($R_f$=0.58) as the major component. The cooled reaction mixture was poured into ice/water (27 L) precipitating a dark brown tar. The aqueous layer was decanted away from the tar and extracted with methylene chloride (5×2 L). The combined extracts were used to redissolve the tar. The methylene chloride solution was washed with 3N hydrochloric acid (4×5 L), followed by water (2 L), then dried over magnesium sulfate. The extracts were filtered, then pressure-filtered through a bed of silica gel, eluting with methylene chloride until all of the desired compound had passed through. The eluate was concentrated on the rotary evaporator to give a slurry of bright yellow crystals (in o-dichlorobenzene). The crystals were collected by filtration, washed with diethyl ether (2×500 ml), then vacuum dried to afford 619.7 g (56.9%) of the desired 2-chloro-9-anthraldehyde (mp 148°–150° C.). 1H NMR (CDCl3): δ 11.35 (s, 1H), 9.02 (d, J=0.9 Hz, 1H), 8.81 (d, J=8.9 Hz, 1H), 8.56 (s, 1H), 7.98 (m, 1H), 7.90 (d, J=8.9 Hz, 1H), 7.66 (m, 1H), 7.53 (m, 1H), 7.42 (m, 1H).

d. (9RS,10RS,12RS)-12-Acetoxy-2-chloro-9,10-dihydro-9, 10-ethanoanthracene- 9-carboxaldehyde.

A mixture of 2-chloro-9-anthraldehyde, prepared as in Example 1c, (100.0 g, 0.415 moles) and vinyl acetate (400 ml, 374 g, 4.34 moles) was placed in a stainless steel bomb (PARR) and heated at 200° C. (sand bath temp.) for 24 h, then cooled. The reaction mixture was concentrated on the rotary evaporator to remove the excess vinyl acetate, leaving the crude product as a tan crystalline solid. The crude product from several batches, which consumed 670.0 g (2.78 moles) of 2-chloro-9-anthraldehyde, was pooled. Trituration with diethyl ether (1.0 L) gave an off-white crystalline solid which was collected by filtration, washed with diethyl ether (2×300 ml), then vacuum dried to afford 629.0 g (69.1%) of the title compound (mp 145°–153° C.). 1H NMR (CDCl3): δ 10.58,10.64 (2s,1H), 7.63 (m) and 7.76 (d, J=1.5 Hz, 1H), 7.15–7.36 (m, 6H), 5.46 (m, 1H), 4.29 (s, 1H), 2.55 (m, 1H), 1.88, 1.91 (2s, 3H), 1.55 (m, 1H).

Evaporation of the filtrates and washes gave a thick brown oil, which was purified by column chromatography over silica gel eluting with a solvent mixture of methylene chloride:hexane (1:1). The recovered solid was recrystallized from diethyl ether:hexane (1:1 - 400 ml) to afford an additional 175.5 g (19.3%) of the desired compound.

e. (9RS,10RS,12RS)-12-Acetoxy-2-chloro-9,10-dihydro-9, 10-ethanoanthracene-9 -carboxylic acid.

A stirred solution of (9RS,10RS,12RS)-12-acetoxy-2-chloro-9,10-dihydro-9,10-ethanoanthracene-9 -carboxaldehyde (629.0 g, 1.925 moles) dissolved in acetone (8.0 L) was treated with Jones Reagent (1.50 L, ~1.93 molesm, prepared as described in Fieser & Fieser Vol. 1: pp 142) over a period of 1 h at 10°–20° C. After the addition of the Jones Reagent, the reaction mixture was stirred for 4 h at room temperature. TLC analysis [silica gel/methylene chloride] showed complete consumption of the aldehyde ($R_f$=0.73). Isopropanol (100 ml) was added and the reaction mixture stirred for 18 h to quench any excess Jones Reagent, resulting in a white suspension over a green-black sludge (chromium salts). The white supernatant was drawn off, and the sludge washed with acetone (5×500 ml). The acetone washes were combined with the supernatant and concentrated on the rotary evaporator to a final volume of 2 L. The residue was poured into ice/water (10 L) and stirred vigorously for 5 h yielding an off-white solid. The material was collected by filtration, washed with water (3×1 L), then vacuum dried to give 665.3 g (99%) of the title compound, mp 270°–273° C. (dec). 1H NMR (DMSO d-6): δ 13.95 (s, 1H), 7.87–7.79 (m, 1H), 7.45–7.12 (m, 6H), 5.27 (d, J=6.4 Hz, 1H), 4.48 (s, 1H), 2.35 (m, 1H), 1.81, 1.84 (2s, 3H), 1.38 (m, 1H). IR max (KBr): 1690 cm-1, C=O, —COOH; 1740 cm-1, C=O, —C °CH$_3$.

f. (9RS,10RS, 12RS)-12-Acetoxy-2-chloro-9,10 dihydro-9, 10-ethanoanthracene-9-carboxylic acid chloride.

(9RS,10RS,12RS)-12-Acetoxy-2-chloro-9,10-dihydro-9, 10-ethanoanthracene-9-carboxylic acid (665.0 g, 1.94 moles) was suspended in toluene (8.0 L). Thionyl chloride (400 g, 3.36 moles) was added in one portion at room temperature followed by a catalytic amount (2 ml) of N,N-dimethylformamide. The mixture was heated gradually to reflux (80° C.) over 1 h, then maintained at reflux for 8 h, yielding a clear amber solution. The cooled reaction mixture was concentracted on the rotary evaporator under pump vacuum to remove the toluene. The crude acid chloride was isolated as a waxy brown solid (804 g, 115% of theory), and was used as such in the next reaction. A small sample of the material was dried under high vacuum to provide a sample for spectral characterization. 1H NMR (CDCl3): δ 7.87 (m, 1H), 7.18–7.40 (m, 6H), 5.57 (m, 1H), 4.29 (s, 1H), 2.58 (m, 1H), 1.91, 1.94 (2s, 3H), 1.50 (m, 1H). IR max (neat film): 1750 cm-1, C=O, —C °CH$_3$; 1790 cm-1, C=O, —C °Cl.

g. (9RS,10RS, 12RS)-12-Acetoxy-2-chloro-9,10-dihydro-9, 10-ethanoanthracene-9-carboxylic acid azide.

The crude acid chloride prepared in Example 1f (804 g, ~1.94 moles) was dissolved in acetone (8.0 L) and the resulting solution cooled by an ice/methanol bath to −5° C. The stirred mixture was treated with an aqueous solution of sodium azide (380 g, 5.84 moles in 1.0 L of water) added over a period of 30 min.. The resulting tan suspension was stirred for 3 h at 0° C., then allowed to warm to room temperature. The mixture was concentrated on the rotary evaporator at 15°–20° C. using pump vacuum to remove the acetone. The residue was partitioned between water (5 L) and toluene (5 L), stirred for 1 h, then filtered. The two-phase filtrate was separated and the aqueous portion extracted with toluene (5×1 L). The toluene extracts were used to redissolve the filter cake isolated earlier. The combined toluene solutions were washed with brine solution (2 L), then dried over magnesium sulfate. The toluene was filtered, then concentrated to ½ volume on the rotary evaporator at 15°–20° C. under pump vacuum. This gave a toluene solution of the acyl azide (yield assumed to be quantitative), which was used in the next reaction. A small sample of the solution was evaporated under high vacuum to isolate a sample of the acyl azide as an off-white sticky solid for spectral characterization. 1H NMR (CDCl3): δ 7.80 (m, 1H), 7.16–7.33 (m, 6H), 5.39 (m, 1H), 4.27 (t, J=2.6 Hz, 1H), 2.50 (m,1H), 1.89, 1.92 (2s, 3H), 1.47 (m, 1H). IR max (nujol): 1720 cm-1, C=O, —CON3; 1750 cm-1 (C=O, —C °CH3), 2160 cm-1 (—N=N=N).

h. (9RS,10RS,12RS)-12-Acetoxy-2-chloro-9,10-dihydro-9, 10-ethanoanthracene-9-isocyanate.

The toluene solution of the crude acyl azide prepared as in Example 1 g (~713.5 g, ~1,94 moles in ~6.0 L of toluene) was heated gradually over a 30 min period to 65° C. At this point, rapid evolution of nitrogen ensued, accompanied by an exotherm which raised the temperature of the reaction mixture to 95° C. The heating mantle was removed until the exotherm subsided (~30 min.), after which time the reaction was heated at reflux for 3 h, then allowed to cool. The toluene was removed on the rotary evaporator using pump vacuum, isolating the crude isocyanate as a thick amber oil (738.5 g, 112% of theory). This material was used in the next reaction without further purification. A sample of the oil was dried under high vacuum to provide a sample for spectral characterization. 1H NMR (CDCl3): δ 7.54 (m, 2H), 7.15–7.30 (m, 5H), 5.03 (m,1H), 4.26 (t, J=2.6 Hz, 1H), 2.55 (m, 1H), 1.98, 2.00 (2s, 3H), 1.56 (m, 1H). IR max (neat film): 1750 cm-1 (C=O, —C °CH3), 2260 cm-1 (—N=C=O).

i. (9RS,10RS,12RS)-9-Amino-2-chloro-12-hydroxy-9,10-dihydro-9,10-ethanoanthracene.

The crude isocyanate prepared as in Example 1h (738.5 g, ~1.94 moles) was dissolved in absolute ethanol (7.0 L) giving a light amber solution. The stirred solution was treated with 20% aqueous sodium hydroxide solution (800 g, 20.0 moles in 4.0 L of water) added in one portion at room temperature. The reaction mixture turned red-brown immediately upon addition of the base. The mixture was heated at reflux for 8 h, then cooled. TLC analysis {silica gel/methylene chloride] showed complete consumption of the isocyanate ($R_f$=0.80). The reaction mixture was concentrated on the rotary evaporator to remove the ethanol, leaving an aqueous suspension of the product which was extracted with methylene chloride (3×5 L). The combined extracts were washed with water (2 L) and brine solution (1L), then dried over magnesium sulfate. Filtration, followed by removal of the solvent in vacuo, yielded the crude amino alcohol as a sticky yellow-brown solid. Trituration with diethyl ether (1.0 L) afforded the pure title compound as a cream colored powder (445.8 g, 84.5%), mp 164°–167° C. 1H NMR (CDCl3): δ 7.09–7.43 (m, 7H), 4.21 (t, J=2.6 Hz, 1H), 3.77 (m, 1H), 2.35 (m, 1H), 2.25 (brs, 3H), 1.48 (m, 1H).

j. (9RS,10RS)-2-Chloro-9,10-dihydro-9,10-methanoanthracene-9-carboxaldehyde.

(9RS,10RS,12RS)-9-Amino-2-chloro-12-hydroxy-9,10-dihydro-9,10-ethanoanthracene prepared as in Example 1i (445.5 g, 1.64 moles) was dissolved in glacial acetic acid (4.0 L), and the resulting solution cooled to 10° C. A solution of sodium nitrite (340.0 g, 4.93 moles) in water (1.4 L) was added to the reaction mixture over a period of 1.75 h. The temperature of the mixture was maintained at 10° C. during the addition of the nitrite, and for 4 h thereafter. The mixture was then stirred overnight and allowed to warm to room temperature. TLC analysis {silica gel/toluene:ethyl acetate (4:1)] showed complete conversion of the amino alcohol ($R_f$=0.12) to the desired aldehyde ($R_f$=0.80). The reaction mixture was diluted with water (4 L) which caused precipitation of a reddish-brown tar. The aqueous supernatant was decanted away from the tar, diluted with an equal volume of crushed ice, then adjusted to pH=5–6 with solid sodium hydroxide. The resulting aqueous mixture was extracted with ethyl acetate (3×1.5 L). The combined ethyl acetate extracts were used to redissolve the tar, and the resulting solution washed with brine (2×1 L) then dried over magnesium sulfate. Filtration, followed by removal of the solvent in vacuo, gave the crude product as a thick brown oil. Purification of this material by column chromatography over silica gel, eluting with a solvent mixture of methylene chloride:hexane (1:1), afforded a thick yellow oil which crystallized on standing (311.7 g, 74.6%). Trituration with diethyl ether:hexane (1:6 - 700 ml) gave a first crop of pure title compound as an off-white crystalline solid (224.1 g, 53.6%), mp 91°–92° C.

1H NMR (CDCl3): δ 10.39 (s, 1H, CHO), 7.50 (d, J=1.9 Hz, 1H, H-C(1)), 7.39 (m, 1H), 7.31 (m, 1H), 7.20 (d, J=7.8 Hz, 1H), 7.01 (m, 3H), 4.37 (s, 1H, H-C(10)), 2.80 (m, 2H, H-C(11)). Material recovered from the mother liquors and washes was repurified by column chromatography as previously described to give an additional 65.0g (15.5%) of the title compound.

k. (9RS,10RS)-2-Chloro-9,10-dihydro-9,10-methanoanthracene-9-carboxylic acid.

A stirred solution of (9RS,10RS)-2-chloro-9,10-dihydro-9,10-methanoanthracene-9-carboxaldehyde prepared as in Example 1i (290.5 g, 1.14 moles) dissolved in acetone (5.0 L) was cooled to 10° C. and treated with Jones Reagent (950 ml, ~1.19 moles) over a period of 1 h. The reaction mixture was stirred overnight at room temperature, then analyzed by TLC {silica gel/methylene chloride:hexane (1:1)]. Conversion of the aldehyde ($R_f$=0.50) to the desired carboxylic acid ($R_f$=0.0–0.15) was shown to be complete. Isopropanol (150 ml) was added, and the mixture stirred for another 3 h to quench any excess Jones Reagent. The acetone supernatant was decanted away from the green-black sludge that had formed, and the sludge was washed with acetone (2×1 L). The combined acetone solutions were concentrated on the rotary evaporator to a volume of 1.5 L, then poured into ice/water (6 L) with vigorous stirring. A yellow-white gum precipitated and gradually solidified with continued stirring. The solid was collected by filtration, pulverized to a fine off-white powder in a mortar & pestle, then rewashed with cold water (2×1 L). Vacuum drying afforded the title compound as an off-white powder (304.8 g, 98.7%), mp 175°–178° C.

1H NMR (CDCl3): δ 7.59 (d, J=1.9 Hz, 1H, H-C(1)), 7.54 (m, 1H), 7.30 (m, 1H), 7.21 (d, J=7.8 Hz, 1H), 7.02 (m, 3H), 4.35 (s, 1H, H-C(10)), 2.88 (m, 2H, H-C(11)).

l. Optical resolution of 2-Chloro-9,10-dihydro-9,10-methano-9-anthracenecarboxylic acid.

To a solution of racemic 2-chloro-9,10-dihydro-9,10-methano-9-anthracenecarboxylic acid (100 g; 0.37M) in ethyl acetate (1.5 L) and methanol (75 mL) was added solid (1S,2S)-(+)-pseudoephedrine (61.1 g; 0.37M). With efficient agitation the mixture was warmed to reflux, held for 30 minutes and slowly cooled to 25° C. After a minimum of 2 h the slurry was filtered and washed with ethyl acetate to yield enriched diastereomeric salt (88.6 g; 0.20M; 55%; diastereomeric ratio 80:20, as determined by HPLC). The enriched salt was slurried in 3% methanolic ethyl acetate (2.74L), warmed to reflux, held 30 minutes, cooled to 25° C. slowly, held 2 h and then filtered and washed with ethyl acetate to provide further enriched salt (70 g; 0.16M; 79%; diastereomeric ratio 95:5, as determined by HPLC). Treatment of the further enriched salt with 5% methanolic ethyl acetate using the same procedure yielded highly enriched salt (60.0 g; 0.14M; 85%; diastereomeric ratio 99:1, as determined by HPLC). This salt (60 g; 0.14M) was added to water (1L) and the consequent suspension acidified to pH 2–3 with concentrated hydrochloric acid (15 mL) and then extracted with diethyl ether (3×500 mL). The combined organic extracts were washed with brine, dried (MgSO4) and evaporated to an oil. Hexane was added and evaporated to afford enantiomerically enriched acid (36 g; 0.13M; 98% recovery; enantiomeric ratio 99:1, as determined by HPLC) as a white solid. Crystallisation from a mixture of hexane (360 mL) and cyclohexane (720 mL) afforded enantiomerically pure (9S,10S)-2-chloro-9,10-dihydro-9,10-methano-9-anthracene-carboxylic acid as a white solid (30 g, 0.11 mol, 81%) mp 172°–173° C. $\alpha_D$=+101° (c=2.0,CHCl$_3$).

Analysis for $C_{16}H_{11}ClO_2$: Calculated: C, 70.99; H, 4.10 Found: C, 70.81; H, 4.21

1H NMR CDCL$_3$: δ 2.80–2.95 (m, 2H),4.35 (s, 1H),6.90–7.10 (m, 3H),7.22 (d, J=7.76 Hz, 1H), 7.27–7.35 (m, 1H),7.48–7.62 (m, 2H).

HPLC analysis: Column: Ultron Ovomucoid (ES-OVM) 15 cm×6 mm Eluant: 15% acetonitrile/85% aqueous KH2PO4 buffer(10 mM) adjusted to pH 5.5 with 1M potassium hydroxide. Flow: 1 mL/min Wavelength: 230 nm Retention times: (+) enantiomer 15.4 min/(−) enantiomer 19.6 min The starting piperidine component was prepared as follows:

m. 1-(1,1-Dimethylethyloxycarbonyl)-4-piperidine carboxylic acid.

A suspension of di-tert-butyl dicarbonate (12.3 g, 56.3 mmol) and isonipectotic acid (6.61 g, 51.2 mmol) in tetrahydrofuran (150 mL) was heated at reflux for 3 h. The resulting homogeneous solution was cooled to room temperature and the solvent removed to leave a white solid, which was triturated with hexane (50 mL) and isolated by filtration. The product was washed with hexane (4×50 mL) and dried in vacuo. Yield: 11.30 g (49.3 mmol, 96%). 1H NMR CDCL$_3$: δ 4.02 (brd, J=11.2 Hz, 2H, eq-H-C(2)), 2.86 (dd, J=11.2, 11.5 Hz, 2H, ax-H-C(2)), 2.49 (m, 1H, H-C(4)), 1.89 (m, 2H, eq-H-C(3)), 1.64 (m, 2H, ax-H-C(3)), 1.46 (s, 9H, (CH$_3$)$_3$C). CIMS: m/z 230 (43%, (M+H)$^+$ for $C_{11}H_{19}NO_4$), 174 (100), 156 (22), 130 (24).

n. N-Methoxy-N-methyl 1-(1,1-Dimethylethyloxycarbonyl)-4-piperidine carboxamide.

A solution of 1-(1,1-Dimethylethyloxycarbonyl)-4-piperidine carboxylic acid (11.3 g, 49.3 mmol), N,O-dimethylhydroxylamine hydrochloride (5.77 g, 59.1 mmol), 1-(3-dimethylaminopropyl)-3-ethyl carbodiimide hydrochloride (11.33 g, 59.1 mmol), 4-dimethylaminopyridine (602 mg, 4.93 mmol) and triethylamine (14.96 g, 148.0 mmol) in dichloromethane (200 mL) was stirred at room temperature for 18 h. The mixture was concentrated to ca. 25 mL, then was poured into 1M hydrochloric acid (75 mL) and extracted with ethyl acetate (3×75 mL). The organic extracts were washed sequentially with 1H hydrochloric acid (50 mL), 10% (v/v) aqueous sodium carbonate (2×50 mL) and brine (50 mL), combined, dried over Na$_2$SO$_4$, filtered and evaporated to afford the title compound as a clear syrup (12.0 g, 44.1 mmol, 89%). 1H NMR CDCL$_3$: δ 4.2 (brm, 2H, eq-H-C(2)), 3.72 (s, 3H, °CH3), 3.19 (s, 3H, NCH3), 2.8 (brm, 3H, ax-H-C(2), H-C(4)), 1.7 (brm, 4H, H-C(3)), 1.46 (s, 9H, (CH$_3$)$_3$C).

o. 1-(1,1-Dimethylethyloxycarbonyl)-4-(3-pyridinoyl)piperidine.

A solution of n-butyllithium (14.2 mL of a 2.51M solution in hexanes, 35.54 mmol) in tetrahydrofuran (50 mL) was cooled to <–85° C. and treated dropwise with a solution of 3-bromopyridine (5.90 g, 37.31 mmol) in tetrahydrofuran (50 mL). The resulting pale yellow-green solution was stirred at <–85° C. for 15 min, then was treated with a solution of N-methoxy-N-methyl 1-(1,1-dimethylethyloxycarbonyl)-4-piperidine carboxamide (8.80 g, 32.31 mmol) in tetrahydrofuran (50 mL). The reaction mixture was allowed to warm to –20° C. over 1 h, then was cooled to –60° C. and quenched by addition of water (20 mL). The mixture was warmed to 0° C., acidified to pH⁻2 by addition of 3M hydrochloric acid and stirred at 0° C. for 10 min. The mixture was then poured into 10% aqueous sodium hydroxide (50 mL) and extracted with ethyl acetate (3×150 mL). The organic extracts were washed sequentially with 1N aqueous sodium hydroxide (100 mL) and brine 100 mL), combined, dried over Na2SO4, filtered and concentrated to leave a yellow semi solid mass. This mass was triturated with hexane (50 mL) and the solid which formed was removed by filtration. The solid was rinsed with hexane (25 mL) and dried to afford the title ketone (6.62 g, 22.8 mmol, 71%) as off-white needles. From the filtrate, an additional 300 mg (1.03 mmol, 3%) of the ketone was obtained. 1H NMR CDCL$_3$: δ 9.16 (d, J=2.2 Hz, 1H, H-C(2')), 8.79 (dd, J=1.7 Hz, 4.8 Hz, 1H, H-C(6')), 8.23 (ddd, J=1.7, 2.2, 8.0 Hz, 1H, H-C(4')), 7.45 (dd, J=4.8, 8.0 Hz, 1H, H-C(5')), 4.17 (brd, J=11 Hz, 2H, eq-H-C(2)), 3.39 (m, 1H, H-C(4)), 2.92 (dd, J=11.6, 11.6 Hz, 2H, ax-H-C(2)), 1.87 (m, 2H, eq-H-C(3)), 1.71 (m, 2H, ax-H-C(3)), 1.47 (s, 9H, (CH$_3$)$_3$C).

p. (+)-1-(1,1-Dimethylethyloxycarbonyl)piperidin-4-yl-pyridin-3-ylmethanol.

A solution of 1-(1,1-dimethylethyloxycarbonyl)-4-(3pyridinoyl)piperidine (5.0 g, 17.22 mmol) in methanol (75 mL) was cooled to 0° C. and sodium borohydride (1.30 g, 34.44 mmol) was added in four portions. The mixture was stirred at 0° C. for 1 h. The solvent was evaporated and the residue was partitioned between water (25 mL) and ethyl acetate (100 mL, 2×50 mL). The organic extracts were washed sequentially with 1N aqueous sodium hydroxide (25 mL) and brine (25 mL), combined, dried over Na2SO4, filtered and evaporated to afford the title alcohol as a white foam (5.02 g, 17.17 mmol, 99%). 1H NMR: δ 8.45 (brs, 2H, H-C(2'), H-C(6')), 7.85 (brd, J=8.4 Hz, 1H, H-C(4')), 7.28 (dd, J=4.9, 8.4 Hz, 1H, H-C(5')), 4.43 (d, J=7.1 Hz, 1H, CHOH), 4.08 (m, 2H, eq-H-C(2)), 3.28 (exs, 1H, CHOH), 2.62 (m, 2H, ax-H-C(2)), 1.90 (m, 2H, eq-H-C(3)), 1.77 (m, 1H, H-C(4)), 1.43 (s, 9H, (CH$_3$)$_3$C), 1.28 (m, 2H, ax-H-C(3)). CIMS: m/z 293 (87%, (M+H)$^+$ for C$_{16}$H$_{24}$N$_2$O$_3$), 265 (19), 237 (100), 219 (14), 175 (24).

q. (+)-Piperidin-4-yl-pyridin-3-ylmethanol.

Trifluoroacetic acid (100 mL) was cooled to 0° C. and added to a flask containing 1-(1,1-dimethylethyl-oxycarbonyl)piperidin-4-yl-pyridin-3-ylmethanol (20.4 g, 69.77 mmol). Vigorous gas evolution was observed. The mixture was stirred at 0° C. until judged complete by TLC. The excess trifluoroacetic acid was removed in vacuo, and the resulting residue was dissolved in water (50 mL). The aqueous solution was cooled to 0° C. and basified to pH⁻12 by addition of sodium hydroxide pellets. The product was isolated by extraction of the aqueous solution with dichloromethane (10×100 mL). The dichloromethane was evaporated to leave the title compound as an off white solid (12.06 g, 62.73 mmol, 90%). 1H NMR(d$_6$-DMSO): δ 8.45 (m, 2H, H-C(2'), H-C(6')), 7.66 (brd, J=7.8 Hz, 1H, H-C(4')), 7.34 (dd, J=4.8, 7.8 Hz, 1H, H-C(3')), 4.29 (d, J=6.7 Hz, 1H, CHOH), 2.67 (m, 2H, eq-H-C(2)), 2.27 (m, 2H, ax-H-C(2)), 1.70 (br, 1H, NH), 1.52 (m, 1H, H-C(4)), 1.10–1.00 (m, 4H, H-C(3)).

r. Optical Resolution of R-1-(4-piperidyl)-1-(3-pyridyl)methanol.

To a solution of racemic piperidin-4-yl-pyridin-3-ylmethanol (20.64 g, 107.5 mmol) in absolute ethanol (475 mL) was added a solution of (–)-2,3-dibenzoyl-L-tartaric acid (38.49 g, 107.5 mmol) in absolute ethanol (400 mL). The resulting mixture was warmed to reflux temperature, held at this temperature for 10 min, then allowed to cool to room temperature. The crystalline material which formed was isolated by filtration to afford a sample of enriched diastereomeric salt (37.5 g, 68.18 mmol). This enriched salt was recrystallized four times from ethanol (2.5 L, 2.4 L, 2.1 L, 1.4 L) to provide the pure diastereomeric salt (15.73 g, 28.57 mmol, 27%). The above pure diastereomeric salt (15.73 g, 28.57 mmol) was dissolved in 10% aqueous sodium hydroxide (50 mL), the solution was diluted with saturated brine (25 mL) and extracted with chloroform (12×100 mL). The combined extracts were dried (K$_2$CO$_3$), filtered and evaporated to afford the enantiomerically pure amine as a white solid. Recrystallization from toluene (75 mL) afforded an analytical sample (4.75 g, 24.71 mmol, 90%), mp 118°–119.5° C. α$_D$=+27.3° (c=1.47, MeOH). Enantiomeric excess as determined by HPLC on chiral stationary phase: >99.5%.

Analysis for C$_{11}$H$_{16}$N$_2$O: Calculated: C, 68.72; H, 8.39; N, 14.57 Found: C, 68.50; H, 8.11; N, 14.49

1H NMR d$_6$-DMSO: δ 8.46 (d, J=2.0 Hz, 1H, H-C(2')), 8.43 (dd, J=1.7, 4.8 Hz, 1H, H-C(6')), 7.66 (ddd, J=1.7, 2.0, 7.8 Hz, 1H, H-C(4')), 7.34 (dd, J=4.8, 7.8 Hz, 1H, H-C(5')), 4.28 (d, J=6.8 Hz, 1H, CHOH), 2.87 (brdd, J=12.0, 21.4 Hz, 2H, eq-H-C(2)), 2.32 (ddd, J=2.5, 12.0, 24.4 Hz, ax-H-C(2)), 1.70 (brd, J=12.0 Hz, 1H, NH), 1.53 (m, 1H, H-C(4)), 1.15–1.01 (m, 4H, H-C(3)) CIMS: m/z 221 ((M+H+C2H4)$^+$, 19%), 194 ((M+H+1)$^+$, 14%), 193 ((M+H)$^+$, 100), 175 ((M+H–H$_2$O)$^+$, 25).

HPLC analysis: Column: Chiralcel OD Eluant: 90% hexane/ 10% ethanol Flow: 0.8 mL/min Wavelength: 215 nm Retention times: (+) enantiomer 20.1 min/(–) enantiomer: 18.5 min The mother liquors from the crystallizations were combined and concentrated to ca. 1 L. The white crystalline solid which formed was isolated by filtration to afford an additional quantity (18.7 g, 33.96 mmol) of salt which was found to be a 1:1 mixture of diastereomers. This material was recrystallized five times from ethanol (900 mL, 600 mL, 550 mL, 500 mL, 450 mL) to afford pure diastereomeric salt (4.62 g, 8.39 mmol, 8%). Generation of the free base by dissolution of the salt in 10% aqueous sodium hydroxide (15 mL), extraction into chloroform (12×50 mL), evaporation and recrystallization from toluene (20 mL) afforded additional enantiomerically pure amine (1.46 g, 7.59 mmol, 91%), mp 119°–122° C. Enantiomeric excess as determined by HPLC on chiral stationary phase: 99%

EXAMPLE 2

R-1-[1-((9R,10R)-2-Chloro-9,10-dihydro-9,10-methanoanthracen-9-ylmethyl)-4-piperidyl]-1-(3-pyridyl)methanol Using a procedure similar to that described in Example 1 except using the (9R,10R) enantiomer of the chloromethanoanthracene carboxylic acid, prepared as described below, and the (1R) enantiomer of the piperidine alcohol, the hydrochloride salt of the title compound was obtained as a white powder (48%), mp 194°–197° C. $\alpha_D=-18.2°$ (c=1.21, methanol)

Analysis for $C_{27}H_{27}ClN_2O\cdot2.0HCl\cdot1.5H_2O$: Calculated: C, 61.08; H, 6.07; N, 5.27 Found: C, 61.02; B, 5.69; N, 5.21 1H NMR (d$_6$-DMSO+TFA-d): δ 8.92 (s, 2H, H-C(2"), H-C(6")), 8.61 (d, J=7.8 Hz, 1H, B-C(4")), 8.12 (dd, J=6.4, 7.8 Hz, 1H, H-C(5")), 7.48 (s, 1H, H-C(1)), 7.32 (m, 3H), 7.01 (m, 3H), 4.77 (d, J=4.4 Hz, 1H, CHOH), 4.48 (s, 1H, H-C(10)), 4.34 (qAB, JAB=14.4 Hz, 2H, CH$_2$N), 3.56 (m, 2H, eq-H-C(2')), 3.22 (m, 2H, ax-H-C(2')), 2.73 (s, 2H, H-C(11)), 2.05–1.71 (m, 5H, H-C(3'), H-C(4')). CIMS: m/z 434 1((M+H+1)$^+$, $^{37}$Cl, 11%), 433 ((M+H)$^+$, $^{37}$Cl, 38%), 432 ((M+H+1)$^+$, $^{35}$Cl, 36%), 431 (M+H)$^+$, $^{35}$Cl, 100%), 430 (19), 429 (13), 413 (23).

The (9R,10R) 2-Chloro-9,10-dihydro-9,10-methanoanthracene-9-carboxylic acid was resolved as follows:

a. Using a procedure similar to that described in Example 11, except using (1R,2R)-(−)-pseudoephedrine as the resolving agent, (9R,10R)-(−)-2-chloromethanoanthracene-9-carboxylic acid was obtained. mp 169°–170°C. $\alpha_D$=100.8 (c=2.0,CHCl$_3$)

Analysis for $C_{16}H_{11}ClO_2$: Calculated: C, 70.99; H, 4.10 Found: C, 70.75; H, 4.18
$^1$H NMR (CDCl$_3$): δ 2.80–2.95 (m, 2H),4.36 (s, 1H), 6.90–7.12 (m, 3H),7.23 (d, J=7.75 Hz, 1H),7.27–7.36 (m, 1H),7.48–7.64 (m, 2H).

EXAMPLE 3

S-1-[1-((9S,10S)-2-Chloro-9,10-dihydro-9,10-methanoanthracen-9-ylmethyl)-4-piperidyl]-1-(3-pyridyl)methanol.

Using a procedure similar to that described in Example 1 except using the (1S) enantiomer of the piperidine alcohol, prepared as described below, and the (9S,10S) enantiomer of the chloromethanoanthracene carboxylic acid, the hydrochloride salt of the title compound was obtained as a white powder (66%), mp 220°–227° C. $\alpha_D$=+17.6° (c=0.51, methanol).

Analysis for $C_{27}H_{27}ClN_2O\cdot2HCl\cdot0.9H_2O$: Calculated: C, 62.14; H, 5.96; N, 5.38 Found: C, 62.14; H, 5.73; N, 5.52 1H NMR (d$_6$-DMSO): δ 8.78 (brs, 2H, H-C(2"), H-C(6")), 8.33 (d, J=8.0 Hz, 1H, H-C(4")), 7.90 (dd, J=5.6, 8.0 Hz, 1H, H-C(5")), 7.50 (d, J=1.5 Hz, 1H, H-C(1)), 7.30 (m, 3H), 6.99 (m, 3H), 4.63 (d, J=5.2 Hz, 1H, CHOH), 4.46 (s, 1H, H-C(10)), 4.27 (m, 2H, CH$_2$N), 3.47 (m, 2H, ax-H-C(2')), 3.19 (m, 2H, eq-H-C(2')), 2.75 (brs, 2H, H-C(11)), 1.96–1.54 (m, 5H, H-C(3'), H-C(4')). CIMS: m/z 434 ((M+H+1)$^+$, $^{37}$Cl, 10%), 433 ((M+H)$^+$, $^{37}$Cl, 35%), 432 ((M+H+1)$^+$, $^{35}$Cl, 34%), 431 (M+H)$^+$, $^{35}$Cl, 100%), 413 (26).

a. Optical Resolution of S-1-(4-piperidyl)-1-(3-pyridyl)methanol.

The combined mother liquors from the preparation of R-(4-piperidyl)-1-(3-pyridyl)methanol, as described in Example 1r, were evaporated to leave a white solid (36 g). This solid was dissolved in 10% aqueous sodium hydroxide (200 mL), placed in a continuous extraction apparatus, and extracted with dichloromethane (1.8 L) over 22 h. The dichloromethane solution was evaporated to leave a yellow semi-solid, which was suspended in hot toluene (300 mL) and filtered. The solids were suspended in chloroform (100 mL) and filtered. The combined filtrates were evaporated to leave a pale yellow foam (9.55 g, 49.67 mmol), which was found to be a 75:25 mixture of S:R enantiomeric alcohols of approximately 80% purity. This solid was dissolved in ethanol (220 mL) and added to a solution of dibenzoyl-D-tartaric acid (17.78 g, 49.67 mmol) in ethanol (185 mL). The mixture was heated to reflux for 10 min, then was cooled to room temperature, which deposited a white crystalline solid. The crystalline salt was isolated by filtration, washed with fresh ethanol (25 mL) and dried to afford diastereoremically enriched salt (83:17 S:R amine, 20.51 g, 37.25 mmol). This salt was recrystallized three times from ethanol (1.2 L, 1.0 L, 0.95 L) to obtain the diastereomerically pure salt (10.26 g, 18.65 mmol, 34%). The salt was dissolved in 10% aqueous sodium hydroxide (40 mL) and saturated brine (20 mL) and the free base extracted into chloroform (12×50 mL). The chloroform extracts were combined, dried (K$_2$CO$_3$), filtered and evaporated to leave an off white solid (3.26 g). This was recrystallized from toluene (40 mL) to obtain enantiomerically pure S-1-(4-piperidyl)-1-(3-pyridyl)methanol (2.93 g, 15.23 mmol, 32%) as a white solid, mp 117.5°–119° C. $\alpha_D$=−24.90(c=1.89, MeOH). Enantiomeric excess as determined by HPLC on chiral stationary phase: >99.5%

Analysis for $C_{11}H_{16}N_2O$: Calculated: C, 68.72; H, 8.39; N, 14.57 Found: C, 68.78; H, 8.46; N, 14.51
1H NMR (d$_6$-DMSO): δ 8.44 (m, 2H, H-C(2'), H-C(6')), 7.66 (d, J=7.8 Hz, 1H, H-C(4')), 7.34 (dd, J=4.8, 7.8 Hz, 1H, H-C(3')), 4.28 (d, J=6.7 Hz, 1H, CHOH), 2.87 (brdd, J=11.8, 21.0 Hz, 2H, eq-H-C(2)), 2.32 (ddd, J=2.1, 12.2, 24.2 Hz, 2H, ax-H-C(2)), 1.70 (d, J=12.5 Hz, 1H, NH), 1.54 (m, 1H, H-C(4)), 1.07 (m, 4H, H-C(3)). CIMS: m/z 194 ((M+H+1)$^+$, 14%), 193 ((M+H)$^+$, 100), 175 (23).

HPLC analysis: Column: Chiralcel OD Eluant: 90% hexane/10% ethanol Flow: 0.8 mL/min Wavelength: 215 nm Retention times: (+) enantiomer 20.1 min/(−) enantiomer: 18.5 min

EXAMPLE 4

S-1-[1-((9R,10R)-2-Chloro-9,10-dihydro-9,10-methanoanthracen-9ylmeth-yl)-4-piperidyl]-1-(3-pyridyl)methanol Using a procedure similar to that described in Example 1 except using the (1S) enantiomer of the piperidine alcohol, and the (9R,10R) enantiomer of the chloromethanoanthracene carboxylic acid, the hydrochloride salt of the title compound was obtained as a white powder (51%), mp 220°–225° C. $\alpha_D$=−44.0°(c=0.5, MeOH)

Analysis for $C_{27}H_{27}ClN_2O\cdot2HCl$: Calculated: C, 64.35; H, 5.80; N, 5.55 Found: C, 64.50; H, 5.95; N, 5.30
$^1$H NMR (d$_6$-DMSO): δ 8.68 (brs, 2H, B-C(2"), H-C(6")), 8.16 (d, J=8.2 Hz, 1H, H-C(4")), 7.75 (dd, J=5.6, 8.2 Hz, 1H, H-C(5")), 7.49 (s, 1H, H-C(1)), 7.32 (m, 3H), 6.99 (m, 3H), 4.57 (d, J=5.5 Hz, 1H, CHOH), 4.46 (s, 1H, H-C(10)), 4.25 (m, 2H, CH$_2$N), 3.41 (m, 2H, ax-H-C(2')), 3.18 (m, 2H, eq-H-C(2')), 2.74 (brs, 2H, H-C(11)), 1.96–1.54 (m, 5H, H-C(3'), H-C(4')). CIMS: m/z 434 ((M+H+1)$^+$, $^{37}$Cl, 12%), 433 ((M+H)$^+$, $^{37}$Cl, 37%), 432 ((M+H+1)$^+$, $^{35}$Cl, 28%) 431 (M+H)$^+$, $^{35}$Cl, 100%), 413 (37).

EXAMPLE 5

(R,S)-1-[1-((9RS,10RS)-2-Chloro-9,10-dihydro-9,10-methanoanthracen-9-ylmethyl)-4-piperidyl]-1-(3-pyridyl)methanol.

A solution of n-butyllithium (2.24 mL of a 2.29M solution in hexane, 5.15 mmol) in tetrahydrofuran (15 mL) was cooled to <−80° C. and treated dropwise with a solution of 3-bromopyridine (813 mg, 5.15 mmol) in tetrahydrofuran (5 mL). The resulting yellow-green solution was stirred at <–80° C. for 30 min, then was treated with a solution of chloromethanoanthracene piperidine aldehyde (1.45 g, 4.12 mmol) in tetrahydrofuran (10 mL). The mixture was stirred at –60° C. for 1 h, then was poured into 10% aqueous sodium hydroxide (50 mL) and extracted with chloroform (3×75 mL). The organic extracts were washed sequentially with 10% aqueous sodium hydroxide (50 mL) and brine (50 mL), combined, dried ($K_2CO_3$), filtered and evaporated To leave an amber foam (1.9 g). Purification of this material by flash chromatography over silica gel (eluant: 3% methanol/ chloroform, 0.1% NH4OH) afforded the title compound (1.46 g) as a white foam. Treatment of this material with ethereal hydrogen chloride afforded white solids, which were reprecipitated from methanol/ether (1:30, 150 mL) to yield the dihydrochloride salt, which was dissolved in water (150 mL) and the solution lyophilized to give the title compound (1.29 g, 2.56 mmol, 62%) as a white powder, mp 219°–225° C. (dec).

Analysis calculated for $C_{27}H_{27}ClN_2O.2HCl.1.4H_2O$: Calculated: C, 61.29; H, 6.06; N, 5.29 Found: C, 61.07; H, 5.74; N, 5.24

$^1H$ NMR ($d_6$-DMSO+TFA-d): δ 8.92 (m, 2H, H-C(2"), H-C(6")), 8.62 (d, J=8.2 Hz, 1H, H-C(4")), 8.13 (dd, J=6.0, 8.0 Hz, 1H, H-C(5")), 7.50 (m, 1H, H-C(1)), 7.34 (m, 3H), 7.02 (m, 3H), 4.79 (m, 1H, CHOH), 4.47 (s, 1H, H-C(10)), 4.36 (m, 2H, CH2N), 3.56 (m, 2H, ax-H-C(2')), 3.24 (m, 2H, eq-H-C(2')), 2.74 (m, 2H, H-C(11)), ].96–1.66 (m, 5H, H-C(3'), H-C(4')). CIMS: m/z 434 ((M+H+1)$^+$, $^{37}$Cl, 11%), 433 ((M+H)$^+$, $^{37}$Cl, 37%), 432 ((M+H+1)$^+$, $^{35}$Cl, 31%), 431 ((M+H)$^+$, $^{35}$Cl, 100%), 413 (21).

The starting piperidine aldehyde was prepared as follows:

a. 1-((9RS,10RS)-2-Chloro-9,10-dihydro-9,10-methanoanthracen-9-ylmethyl)-4 -formylpiperidine.

A solution of oxalyl chloride (4.51 g, 35.6 mmol) in dichloromethane (100 mL) was cooled to <–60° C. and was treated dropwise with dimethylsulfoxide (2.92 g, 37.4 mmol). The resulting solution was stirred at –65° C. for 15 min, then was treated dropwise with a solution of1-((9RS, 10RS)-2-chloro-9,10-dihydro-9,10-methanoanthracen-9-ylmethyl)-4 -piperidinemethanol (8.40 g, 23.7 mmol) in dichloromethane (30 mL). The reaction mixture was stirred at –65° C. for 1 h, then was treated with triethylamine (7.20 g, 71.2 mmol) and allowed to warm to room temperature. The mixture was then poured into 10% aqueous sodium hydroxide (100 mL) and was extracted with chloroform (3×150 mL). The organic extracts were washed sequentially with 1N aqueous sodium hydroxide (100 mL) and brine (100 mL), combined, dried ($K_2CO_3$), filtered and evaporated to leave the title compound as an amber foam (8.12 g, 23.1 mmol, 97%). 1H NMR (d6-DMSO): 9.57 (s, 1H, CHO), 7.25 (m, 4H), 6.94 (m, 3H), 4.33 (s, 1H, H-C(10)), 3.34 (m, 2H, CH2N), 2.87 (m, 2H, eq-H-C(2')), 2.50 (s, 2H, H-C(11)), 2.29 (m, 3H, ax-H-C(2'), H-C(4')), 1.75 (m, 2H, eq-H-C(3')), 1.46 (m, 2H, ax-H-C(3')).

b. 1-((9RS,10RS)-2-Chloro-9,10-dihydro-9,10-methanoanthracen-9-ylmethyl)-4-piperidinemethanol.

A suspension of lithium aluminum hydride (4.53 g, 119.5 mmol) in tetrahydrofuran (175 mL) was heated to reflux temperature and was treated dropwise with a solution of ethyl 1-((9RS,10RS)-2-chloro-9,10-dihydro-9,10 -methanoanthracen-9-ylcarbonyl)-4-piperidine carboxylate (9.83 g, 23.9 mmol) in tetrahydrofuran (75 mL) at a rate sufficient to maintain reflux. Upon complete addition, the mixture was stirred for 1 h at reflux, then was cooled to 0° C. and quenched by sequential addition of water (4.5 mL), 10% aqueous sodium hydroxide (4.5 mL) and water (13.5 mL). The resulting milky suspension was treated with Celite, warmed to room temperature and stirred for 15 min. The solids were removed by filtration through Celite, the filter cake was washed with tetrahydrofuran/methanol (20:1, 2×200 mL), and the filtrate was evaporated. Trituration of the solid obtained with ethyl acetate/hexane (1:1, 50 mL) and evaporation of solvent afforded the title compound as a white solid (8.40 g, 23.7 mmol, 99%). 1H NMR (d6-DMSO): δ 7.24 (m, 4H), 6.93 (m, 4H), 4.39 (brs, 1H, CH20H), 4.30 (s, 1H, H-C(10)), 3.36–3.21 (m, 4H, CH20H, CH2N), 2.96 (m, 2H, eq-H-C(2')), 2.46 (s, 2H, H-C(11)), 2.15 (m, 2H, ax-H-C(2')), 1.60 (m, 2H, eq-H-C(3')), 1.35 (m, 1m, H-C(4')), 1.10 (m, 2H, ax-H-C(3')).

c. Ethyl 1-((9RS,10RS)-2-chloro-9,10-dihydro-9,10-methanoanthracen-9-ylcarbonyl)-4 -piperidine carboxylate.

A suspension of (9RS,10RS)-2-chloro-9,10-dihydro-9, 10-methano-9-anthracenecarboxylic acid (7.50 g, 27.7 mmol), prepared as described in Example 1j, in toluene (75 mL) was treated with thionyl chloride (4.12 g, 34.6 mmol) and N,N-dimethylformamide (2 drops). The mixture was heated to reflux for 3 h, then was cooled to room temperature and treated with ethyl isonipecotate (10.88 g, 69.25 mmol). The resulting thick slurry was stirred at room temperature for 16 h, then was poured into 1N hydrochloric acid (100 mL) and extracted with ethyl acetate (3×100 mL). The organic extracts were washed sequentially with 1N hydrochloric acid (100 mL), 10% aqueous sodium bicarbonate (100 mL) and brine (100 ml), combined, dried (MgSO4), filtered and evaporated to leave an amber oil which solidified on standing. The crystalline product was triturated with hexane (300 mL) and ether (25 mL), isolated by filtration, washed with hexane/ether (10:1, 50 mL) and air dried to afford the title compound (9.83 g, 23.9 mmol, 87%) as a white solid. 1H NMR ($d_6$-DMSO): δ 7.5 (br, 1H, H-C(1)), 7.35 (m, 3H), 7.01 (m, 3H), 4.5 (br, 1H), 4.43 (s, 1H, H-C(10)), 4.08 (q, J=7.0 Hz, 2H, CH2CH3), 3.6 (br, 1H), 3.2–2.55 (brm, 6H), 2.05–1.45 (brm, 5H), 1.19 (t, J=7.0 Hz, 3H, CH2CH3).

EXAMPLE 6

1-[1-(9,10-Dihydro-9,10-methanoanthracen-9-ylmethyl) -4-piperidyl]-1-(3 -pyridyl)methanol.

By a procedure similar to that described in Example 5, except using the piperidine aldehyde prepared as described below, the hydrochloride salt of the title compound was obtained as a white powder (55%), mp 235°–238° C.

Analysis for $C_{27}H_{28}N_2O$. 2.0HCl.1.4H$_2$O: Calculated: C, 65.55; H, 6.68; N, 5.66 Found: C, 65.44; H, 6.56; N, 5.55
$^1H$ NMR ($d_6$-DMSO+TFA-d): δ 8.92 (m, 2H, H-C(2"), H-C(6")), 8.60 (d, J=8.3 Hz, 1H, H-C(4")), 8.13 (dd, J=5.9, 8.3 Hz, 1H, H-C(5")), 7.32 (m, 4H), 7.00 (m, 4H), 4.78 (d, J=4.8 Hz, 1H, CHOH), 4.45 (s, 1H, H-C(10)), 4.30 (s, 2H, CH$_2$N), 3.58 (m, 2H, ax-H-C(2')), 3.25 (m, 2H, eq-H-C(2')), 2.71 (s, 2H, H-C(11)), 2.0–1.65 (m, 5H, H-C(3'), H-C(4')). CIMS: m/z 398 ((M+H+1)$^+$, 30%), 397 ((M+H)$^+$, 100), 379 (15).

The starting piperidine aldehyde was prepared as follows:
a. 1-(9,10-Dihydro-9,10-methanoanthracen-9-ylmethyl)-4-formylpiperidine.

A solution of oxalyl chloride (3.86 g, 30.4 mmol) in dichloromethane (100 mL) was cooled to –60° C. and treated dropwise with dimethylsulfoxide (2.49 g, 31.89 mmol), resulting in vigorous gas evolution. The resulting mixture was stirred at –60° C. for 15 min, then was treated dropwise with a solution of 1-(9,10-dihydro-9,10-methanoanthracen-9-ylmethyl)4 -piperidinemethanol (6.47 g, 20.25 mmol) in dichloromethane (30 mL). This mixture was stirred at −60° C. for 1 h, then was treated with triethylamine (6.15 g, 60.75 mmol). The reaction was allowed to warm to room temperature, then was poured into 10% aqueous sodium hydroxide (50 mL) and extracted with chloroform (3×75 mL). The organic extracts were washed sequentially with 1N aqueous sodium hydroxide (50 mL) and brine (50 mL), combined, dried ($K_2CO_3$), filtered and evaporated to leave a tan solid. Trituration with hexane (50 mL) followed by filtration gave the title compound (5.09 g, 16.05 mmol, 79%) as a tan solid. 1H NMR (d6-DMSO): δ 9.57 (s, 1H, CHO), 7.28 (m, 2H), 7.17 (m, 2H), 6.91 (m, 4H), 4.30 (s, 1H, H-C(10)), 3.34 (s, 2H, CH2N), 2.86 (m, 2H, eq-H-C(2')), 2.45 (s, 2H, H-C(11)), 2.29 (m, 3H, ax-H-C(2'), H-C(4')), 1.76 (m, 2H, eq-H-C(3')), 1.45 (m, 2H, ax-H-C(3')).

b. 1-(9,10-Dihydro-9,10-methanoanthracen-9-ylmethyl)4-piperidinemethanol.

A solution of ethyl 1-(9,10-dihydro-9,10-methanoanthracen-9-ylcarbonyl)-4-piperidine carboxylate (33.0g, 88.4 mmol) in tetrahydrofuran (50 mL) was added dropwise to a suspension of lithium aluminum hydride (4.70 g, 123.8 mmol) in tetrahydrofuran (70 mL) held at reflux temperature. Upon complete addition, the mixture was held at reflux for 2 h, then was cooled to 0° C. and treated sequentially with 10% aqueous sodium hydroxide (4.7 mL), water (4.7 mL) and 10% aqueous sodium hydroxide (14.1 mL). The resulting white slurry was stirred for 30 minutes, treated with diatomaceous earth (25 g) and filtered through a pad of diatomaceous earth. The filter cake was washed with tetrahydrofuran/methanol (20:1, 2×200 mL). The filtrate was evaporated to give the title compound as a tan solid (23.5 g, 77.0 mmol, 87%) 1H NMR (d6-DMSO): δ 7.25 (m, 2H), 7.18 (m, 2H), 4.38 (t, J=5.2 Hz, 1H, CH2OH), 4.29 (s, 1H, H-C(10)), 3.32 (s, 2H, CH2N), 3.21 (m, 2H, CH2OH), 2.97 (d, 3-11.2 Hz, 2H, eq-H-C(2')), 2.44 (s, 2H, H-C(11), 2.14 (dd, J=11.2, 11.2 Hz, ax-H-C(2')), 1.58 (d, J=11.0 Hz, eq-H-C(3')), 1.34 (m, 1H, H-C(4')), 1.10 (ddd, J=3.5, 11.0, 11.2 Hz, 2H, ax-H-C(3')).

c. Ethyl 1-(9,10-dihydro-9,10-methanoanthracen-9-ylcarbonyl)-4-piperidine carboxylate.

A solution of 9,10-dihydro-9,10-methano-9-anthracenecarboxylic acid (21.8 g, 92.4 mmol) in toluene (160 mL) was treated with thionyl chloride (11.7 g, 99 mmol) and N,N-dimethylformamide (0.1 g). The resulting solution was heated to reflux temperature for 2 h, then was cooled to room temperature. The mixture was then treated dropwise with a solution of ethyl isonipecotate (31.1 g, 198 mmol) in toluene (20 mL), using an ice/water bath to keep the reaction temperature <35° C. Upon complete addition, the mixture was stirred for 1 h at room temperature, then was washed sequentially with 10% hydrochloric acid (40 mL), water (40 mL), 1N aqueous sodium hydroxide (40 mL), water (40 mL) and brine (40 mL). The aqueous washes were extracted with toluene (100 mL). The organic extracts were combined, dried (MgSO4), filtered and concentrated to afford the title compound (33.0 g, 85.2 mmol, 92%) as an off-white solid. 1H NMR (d6-DMSO): δ 7.33–7.14 (m, 4H), 6.99 (m, 4H), 4.54 (br, 1H), 4.38 (s, 1H, H-C(10)), 4.09 (q, J=6.5 Hz, 2H, CH2CH3), 3.8 (br, 1H), 3.0–2.5 (br, 6H), 2.05–1.45 (br, 5H), 1.19 (t, J=6.5 Hz, 3H, CH2CH3).

EXAMPLE 7

(R,S)-1-[1-(9,10-Dihydro-9,10-methanoanthracen-9-ylmethyl)-4-piperidyl]-1-(2-pyridyl)methanol.

By a procedure similar to that described in Example 5, except using 2-bromopyridine in the lithiation procedure, and the piperidine aldehyde prepared as described in Example 6a, the hydrochloride salt of the title compound was obtained as a white powder (41%), mp 211°–214° C.

Analysis for $C_{27}H_{28}N_2O.2.0HCl.1.25H_2O$: Calculated: C, 65.92; H, 6.66; N, 5.69 Found: C, 66.00; H, 6.63; N, 5.57 1H NMR (d6-DMSO+TFA-d): δ 8.85 (d, J=4.9 Hz, 1H, H-C(6")), 8.65 (m, 1H, H-C(3"), 8.13–8.02 (m, 2H, H-C(4"), H-C(5")), 7.34 (m, 4H), 6.99 (m, 4H), 5.02 (brs, 1H, CHOH), 4.45 (s, 1H, H-C(10)), 4.34 (s, 2H, CH2N), 3.55 (m, 2H, ax-H-C(2')), 3.25 (m, 2H, eq-H-C(2')), 2.71 (s, 2H, H-C(11)), 2.25–1.50 (m, 5H, H-C(3'), H-C(4')). CIMS: m/z 398 ((M+H+1)+, 27%) 397 ((M+H)+, 100), 379 (3).

EXAMPLE 8

(R,S)-1-[1-((9RS,10RS)-2-Chloro-9,10-dihydro-9,10-methanoanthracen-9-ylmethyl)-4-piperidyl]-1-(2-pyridyl)methanol.

By a procedure similar to that described in Example 5, except using 2-bromopyridine in the lithiation procedure, and the piperidine aldehyde prepared as described in Example 5a, the hydrochloride salt of the title compound was obtained as a white powder (53%), mp 230°–234° C.

Analysis for $C_{27}H_{27}ClN_2O.2.0HCl0.8H_2O$: Calculated: C, 62.57; H, 5.95; N, 5.40 Found: C, 62.48; H, 6.03; N, 5.25 $^1$H NMR (d6-DMSO+TFA-d): δ 8.85 (d, J=5.8 Hz, 1H, H-C(6")), 8.63 (m, 1H, H-C(3"), 8.12 (d, J=7.9 Hz, H-C(4"), 8.02 (dd, J=5.8, 7.9 Hz, H-C(5")), 7. 49 (d, J=1.5 Hz, 1H, H-C(2)), 7.32 (m, 3H), 7.03 (m, 3H), 5.03 (brs, 1H, CHOH), 4.47 (s, 1H, H-C(10)), 4.35 ($q_{AB}$, $J_{AB}$=12.1 Hz, 2H, CH2N), 3.57 (m, 2H, ax-H-C(2')), 3.22 (m, 2H, eq-H-C(2')), 2.74 (s, 2H, H-C(11)), 2.2–1.5 (m, 5H, H-C(3'), H-C(4')). CIMS: m/z 434 ((M+H+1)+, $^{37}$Cl, 5%), 433 ((M+H)+, $^{37\ Cl}$, 20%) 432 ((M+H+1)+, $^{35}$Cl, 17%), 431 (M+H)+, $^{35}$Cl, 61%)

EXAMPLE 9

(R,S)-1-[1-(9,10-Dihydro-9,10-methanoanthracen-9-ylmethyl)-4-piperidyl]-1-(4 -isoquinolyl)methanol.

By a procedure similar to that described in Example 5, except using 4-bromoisoquinoline in the lithiation procedure, and the piperidine aldehyde prepared as described in Example 6a, the hydrochloride salt of the title compound was obtained as a white powder (30%), mp 215°–220° C.

Analysis for $C_{31}H_{30}N_2O.2.0HCl.1.0H_2O$: Calculated: C, 69.27; H, 6.38; N, 5.21 Found: C, 69.45; H, 6.34; N, 5.25 $^1$H NMR (d6-DMSO+TFA-d): δ 9.92 (s, 1H, H-C(2")), 8.71–8.58 (m, 3H, H-C(1"), H-C(5"), H-C(8")), 8.28 (dd, J=7.7, 7.8 Hz, 1H, H-C(6")), 8.08 (dd, J=7.7, 7.8 Hz, 1H, H-C(7")), 7.32 (m, 4H), 6.99 (m, 4H), 5.41 (d, J=3.0 Hz, 1H, CHOH), 4.45 (s, 1H, H-C(10)), 4.29 (s, 2H, CH2N), 3.55 (m, 2H, ax-H-C(2')), 3.25 (m, 2H, eq-H-C(2')), 2.70 (s, 2H, H-C(11)), 2.32–1.61 (m, 5H, H-C(3'), H-C(4')). CIMS: m/z 448 ((M+H+1)+, 35%), 447 ((M+H)+, 100), 446 (16), 429 (16).

EXAMPLE 10

(R,S)-1-[1-(9,10-Dihydro-9,10-methanoanthracen-9-ylmethyl)-4-piperidyl]-1-(3-quinolyl)methanol.

By a procedure similar to that described in Example 5, except using 3-bromoquinoline in the lithiation procedure, and the piperidine aldehyde prepared as described in Example 6a, the hydrochloride salt of the title compound was obtained as a white powder (57%), mp 195°–205° C.

Analysis for $C_{31}H_{30}N_2O.2.0HCl.1.5H_2O$: Calculated: C, 68.12; H, 6.45; N, 5.13 Found: C, 68.24; H, 6.18; N, 4.99
$^1H$ NMR ($d_6$-DMSO +TFA-d): δ 9.38 (d, J=1.8 Hz, 1H, H-C(2")), 9.20 (s, 1H, H-C(4")), 8.43 (d, J=8.0 Hz, H-C(5")), 8.38 (d, J=8.6 Hz, H-C(8"), 8.17 (m, 1H, H-C(6")), 8.00 (m, H-C(7")), 7.34 (m, 4H), 6.98 (m, 4H), 4.93 (d, J=4.8 Hz, 1H, CHOH), 4.45 (s, 1H, H-C(10)), 4.35 (s, 2H, CH$_2$N), 3.59 (m, 2H, ax-H-C(2')), 3.25 (m, 2H, eq-H-C(2')), 2.70 (s, 2H, H-C(11)), 2.2–1.6 (m, 5H, H-C(3'), H-C(4')). CIMS: m/z 448 ((M+H+1)$^+$, 30%), 447 ((M+H)$^+$, 81), 446 (9), 429 (15) 130 (100).

EXAMPLE 11

(R,S)-1-[1-(9,10-Dihydro-9,10-methanoanthracen-9-ylmethyl)-4piperidyl]-1-(3-methoxyphenyl)methanol.

By a procedure similar to that described in Example 5, except using 3-bromoanisole in the lithiation procedure, and the piperidine aldehyde prepared as described in Example 6a, the hydrochloride salt of the title compound was obtained as a white powder (77%), mp 180°–184° C.

Analysis for $C_{29}H_{31}NO_2.1.0HCl..0.5H_2O$: Calculated: C, 73.95; H, 7.06; N, 2.97 Found: C, 73.69; H, 7.26; N, 2.86
$^1H$ NMR ($d_6$-DMSO+TFA-d): δ 7.32 (m, 5H), 6.98 (m, 4H), 6.83 (m, 3H), 4.44 (s, 1H, H-C(10)), 4.34 (d, J=5.0 Hz, 1H, CHOH), 4.29 (s, 2H, CH$_2$N), 3.75 (s, 3H, OCH$_3$), 3.55 (m, 2H, ax-H-C(2')), 3.22 (m, 2H, eq-H-C(2')), 2.70 (s, 2H, H-C(11)), 1.87–1.50 (m, 5H, H-C(3'), H-C(4')) CIMS: m/z 427 ((M+H+1)$^+$, 23%), 426 (M+H)$^+$, 100) 408 (21).

EXAMPLE 12

(R,S)-1-{1-(9,10-Dihydro-9,10-methanoanthracen-9-ylmethyl)-4-piperidyl]-1-(4-methoxyphenyl)methanol.

By a procedure similar to that described in Example 5, except using 4-bromoanisole in the lithiation procedure, and the piperidine aldehyde prepared as described in Example 6a, the hydrochloride salt of the title compound was obtained as a white powder (33%), mp 109°–115° C.

Analysis for $C_{29}H_{31}NO_2.1.0C6H807.1.25H_2O$: Calculated: C, 63.69; H, 6.37; N, 2.03 Found: C, 63.69; H, 6.14; N, 2.05
$^1H$ NMR ($d_6$-DMSO+TFA-d): δ 7.27 (m, 6H), 6.93 (m, 6H), 4.44 (s, 1H, H-C(10)), 4.32 (d, J=5.5 Hz, 1H, CHOH), 4.29 (s, 2H, CH$_2$N), 3.73 (s, 3H, OCH$_3$), 3.57 (m, 2H, ax-H-C(2')), 3.22 (m, 2H, eq-H-C(2')), 2.73 (qAB, J$_{AB}$=15.4 Hz, 4H, citrate), 2.65 (s, 2H, H-C(11)), 1.85–1.50 (m, 5H, H-C(3'), H-C(4')). CIMS: m/z 427 ((M+H+1)$^+$, 27%), 426 (M+H)$^+$, 100), 408 (57).

EXAMPLE 13

(R,S)-1-[1-(9,10-Dihydro-9,10-methanoanthracen-9-ylmethyl)-4-piperidyl]-1-(1-naphthyl)methanol.

By a procedure similar to that described in Example 5, except using 1-bromonaphthalene in the lithiation procedure, and the piperidine aldehyde prepared as described in Example 6a, the hydrochloride salt of the title compound was obtained as a white powder (64%), mp 185°–190° C.

Analysis for $C_{32}H_{31}NO.1.0HCl.0.7H_2O$: Calculated: C, 77.69; H, 6.80; N, 2.83 Found: C, 77.59; H, 6.71; N, 2.80
$^1H$ NMR ($d_6$-DMSO+TFA-d): δ 8.20 (d, J=7.8 Hz, 1H), 7.95 (d, J=7.2 Hz, 1H), 7.48 (d, J=8.0 Hz, 1H), 7.56 (m, 4H), 7.33 (m, 4H), 6.98 (m, 4H), 5.24 (d, J=4.4 Hz, 1H, CHOH), 4.44 (s, 1H, H-C(10)), 4.26 (s, 2H, CH$_2$N), 3.56 (m, 2H, ax-H-C(2')), 3.19 (m, 2H, eq-H-C(2')), 2.68 (s, H, H-C(11)), 1.9–1.5 (m, 5H, H-C(3'), H-C(4')). CIMS: m/z 447 ((M+H+1)$^+$, 38%), 446 ((M+H)$^+$, 100), 445 (10), 428 (33).

EXAMPLE 14

(R,S)-1-[1-(9,10-Dihydro-9,10-methanoanthracen-9-ylmethyl)-4-piperidyl]-1-(3,4-dichlorophenyl)methanol.

By a procedure similar to that described in Example 5, except using 1-bromo-3,4-dichlorobenzene in the lithiation procedure, and the piperidine aldehyde prepared as described in Example 6a, the hydrochloride salt of the title compound was obtained as a white powder (33%), mp 187°–193° C.

Analysis for $C_{28}H_{27}Cl_2NO.1.0HCl.0.6H_2O$: Calculated: C, 65.72; H, 5.75; N, 2.73 Found: C, 65.64; H, 5.58; N, 2.66
$^1H$ NMR ($d_6$-DMSO+TFA-d): δ 7.60 (d, J=8.2 Hz, 1H, M-C(6")), 7.55 (d, J=1.8 Hz, 1H, H-C(2")), 7.32 (m, 5H), 6.98 (m, 4H), 4.47 (d, J=5.2 Hz, 1H, CHOH), 4.44 (s, 1H, H-C(10)), 4.30 (s, 2H, CH$_2$N), 3.58 (m, 2H, ax-H-C(2')), 3.21 (m, 2H, eq-H-C(2')), 2.67 (s, 2H, H-C(11)), 1.9–1.5 (m, 5H, H-C(3'), H-C(4')) CIMS: m/z 468 ((M+H)$^+$, $^{37}Cl^{37}Cl$, 12%), 467 ((M+H+1)$^+$, $^{37}Cl^{35}Cl$, 19%), 466 ((M+H)$^+$, $^{37}Cl^{35}Cl$, 62%), 465 ((M+H+1)$^+$, $^{35}Cl^{35}Cl$, 40%), 466 ((M+H)$^+$, $^{35}Cl^{35}Cl$, 100) 463 (24), 462 (19), 448 (20), 447 (10), 446 (35).

EXAMPLE 15

(R,S)-1-[1-((9RS,10RS)-2-Chloro-9,10-dihydro-9,10-methanoanthracen-9ylmethyl)-4-piperidyl]-1-(3-methoxyphenyl)methanol.

By a procedure similar to that described in Example 5, except using 3-bromoanisole in the lithiation procedure, and the piperidine aldehyde prepared as described in Example 5a, the citrate salt of the title compound was obtained as a white powder (21%), mp 132° C.

Analysis for $C_{29}H_{30}ClNO_2.2C_6H_8O_7.0.2H_2O$: Calculated: C, 62.29; H, 5.78; N, 1.99 Found: C, 62.15; H, 5.71; N, 2.0
$^1H$ NMR ($d_6$-DMSO+TFA-d): δ 7.45 (d, J=1.5 Hz, H-C(1)), 7.29 (m, 4H), 6.92 (m, 6H), 4.46 (s, 1H, H-C(10)), 4.38 (d, J=5.1 Hz, 1H, CHOH), 4.31 (q$_{AB}$, J$_{AB}$=14.1Hz, 2H, CH$_2$N), 3.75 (s, 3H, OCH$_3$), 3.58 (m, 2H, ax-H-C(2')), 3.19 (m, 2H, eq-H-C(2')), 2.75 (q$_{AB}$, J$_{AB}$=15.3 Hz, 4H, citrate), 2.69 (s, 2H, H-C(11)), 1.82–1.62 (m, 5H, H-C(3'), M-C(4')). CIMS: m/z 462 ((M+H)$^+$, $^{37}$Cl, 37%), 461 ((M+H+1)$^+$, $^{35}$Cl, 38%) 460 ((M+H)$^+$, $^{35}$Cl, 100) 459 (21), 444 (13), 442 (38).

EXAMPLE 16

(R,S)-1-[1-((9RS,10RS)-2-Chloro-9,10-dihydro-9,10-methanoanthracen-9-ylmethyl)-4-piperidyl]-1-(3-methoxyphenyl)methanol.

By a procedure similar to that described in Example 15, the hydrochloride salt of the title compound was obtained as a white powder (59%), mp 165°–170° C.

Analysis for $C_{29}H_{30}ClNO_2.1.0HCl.0.25H_2O$: Calculated: C, 69.53; H, 6.34; N, 2.80 Found: C, 69.54; H, 6.31; N, 2.72
$^1H$ NMR ($d_6$-DMSO+TFA-d): δ 7.46 (d, J=1.6 Hz, H-C(1)), 7.29 (m, 4H), 6.92 (m, 6H), 4.46 (s, 1H, H-C(10)), 4.38 (d, J=5.0 Hz, 1H, CHOH), 4.32 (q$_{AB}$, J$_{AB}$=14.4 Hz, 2H, CH$_2$N), 3.76 (s, 3H, OCH$_3$), 3.57 (m, 2H, ax-H-C(2')), 3.21 (m, 2H, eq-H-C(2')), 2.71 (q$_{AB}$, J$_{AB}$=8.5 Hz, 2H, H-C(11)), 1.96–1.54 (m, 5H, H-C(3'), H-C(4')). CIMS: m/z 462 ((M+H)$^+$, $^{37}$Cl, 35%), 461 ((M+H+1)$^+$, $^{35}$Cl, 37%) 460 ((M+H)$^+$, $^{35}$Cl, 100), 459 (25), 444 (11), 442 (42).

EXAMPLE 17

(R,S)-1-[1-(9,10-Dihydro-9,10-methanoanthracen-9-ylmethyl)-4piperidyl]-1-(4-methylphenyl)methanol.

By a procedure similar to that described in Example 5, except using 4-bromotoluene in the lithiation procedure, and the piperidine aldehyde prepared as described in Example 6a, the hydrochloride salt of the title compound was obtained as a white powder (24%), mp 180°–182° C.

Analysis for C$_{29}$H$_{31}$NO.1.0HCl.1.2H$_2$O: Calculated: C, 74.48; H, 7.41; N, 2.99 Found: C, 74.44; H, 7.14; N, 2.99
$^1$H NMR (d$_6$-DMSO+TFA-d): δ 7.32 (m, 4H), 7.16 (m, 4H), 6.98 (m, 4H), 4.43 (s, 1H, H-C(10)), 4.36 (d, J=5.0 Hz, 1H, CHOH), 3.58 (m, 2H, ax-H-C(2')), 3.22 (m, 2H, eq-H-C(2')), 2.67 (s, 2H, H-C(11)), 2.28 (s, 3H, CH3), 1.9–1.5 (m, 5H, H-C(3'), H-C(4')). CIMS: m/z 411 ((M+H+1)$^+$, 30%), 410 ((M+H)$^+$, 100), 409 (31), 408 (20), 393 (14), 392 (50).

EXAMPLE 18

(R,S)-1-[1-(9,10-Dihydro-9,10-methanoanthracen-9-ylmethyl)-4piperidyl]-1-(2-methoxyphenyl)methanol By a procedure similar to that described in Example 5, except using 2-bromoanisole in the lithiation procedure, and the piperidine aldehyde prepared as described in Example 6a, the citrate salt of the title compound was obtained as a white powder (33%), mp 115°–120 ° C.

Analysis for C$_{29}$H$_{31}$NO$_2$.1.3C$_6$H$_8$O$_7$.0.6H$_2$O: Calculated: C, 64.41; H, 6.25; N, 2.04 Found: C, 64.42; H, 6.06; N, 2.10
$^1$H NMR (d$_6$-DMSO+TFA-d): δ 7.32 (m, 6H), 6.97 (m, 6H), 4.80 (d, J=5.0 Hz, 1H, CHOH), 4.44 (s, 1H, H-C(10)), 4.29 (s, 2H, CH2N), 3.78 (s, 3H, OCH3), 3.60 (m, 2H, ax-H-C(2')), 3.18 (m, 2H, eq-H-C(2')), 2.75 (q$_{AB}$, J$_{AB}$=15.4 Hz, 4H, citrate), 2.68 (s, 2H, H-C(11)), 1.9–1.5 (m, 5H, H-C(3'), H-C(4')). CIMS: m/z 427 ((M+H+1)$^+$, 34%) 426 ((M+H)$^+$, 100), 425 (22), 424 (10), 409 (15), 408 (46).

EXAMPLE 19

(R,S)-1-[1-(9,10-Dihydro-9,10-methanoanthracen-9-ylmethyl)-4-piperidyl]-1-(2,5-dimethoxyphenyl)methanol.

By a procedure similar to that described in Example 5, except using 1-bromo-2,5-dimethoxybenzene in the lithiation procedure, and the piperidine aldehyde prepared as described in Example 6a, the citrate salt of the title compound was obtained as a white powder (34%), mp 135°–137° C.

Analysis for C$_{30}$H$_{33}$NO$_3$.1.0C$_6$H$_8$O$_7$.1.2H$_2$O: Calculated: C, 64.60; H, 6.53; N, 2.09 Found: C, 64.39; H, 6.18; N, 2.13
$^1$H NMR (d$_6$-DMSO+TFA-d): δ 7.32 (m, 4H), 6.90 (m, 7H), 4.76 (d, J=4.0 Hz, 1H, CHOH), 4.44 (s, 1H, H-C(10)), 4.29 (s, 2H, CH2N), 3.73 (s, 3H, OCH3), 3.70 (s, 3H, OCH3), 3.55 (m, 2H, ax-H-C(2')), 3.20 (m, 2H, eq-H-C(2')), 2.70 (q$_{AB}$, J$_{AB}$=15.4 Hz, 4H, citrate), 2.68 (s, 2H, H-C(11)), 1.9–1.5 (m, 5H, H-C(3'), H-C(4')). CIMS: m/z 457 ((M+H+1)$^+$, 39%), 456 ((M+H)$^+$, 100) 455 (13) 439 (17), 438 (46), 113 (31).

EXAMPLE 20

(R,S)-1-[1-(9,10-Dihydro-9,10-methanoanthracen-9-ylmethyl)-4-piperidyl]-1-(2,4-imethoxyphenyl)methanol By a procedure similar to that described in Example 5, except using 1-bromo-2,4-dimethoxybenzene in the lithiation procedure, and the piperidine aldehyde prepared as described in Example 6a, the citrate salt of the title compound was obtained as a white powder (22%), mp 145°–150° C.

Analysis for C$_{38}$H$_{38}$N$_2$O$_3$.1.0HCl.1.2H$_2$O: Calculated: C, 64.60; H, 6.53; N, 2.09 Found: C, 64.65; H, 6.31; N, 2.10
$^1$H NMR (d$_6$-DMSO+TFA-d): δ 7.31 (m, 5H), 7.00 (m, 4H), 6.54 (m, 2H), 4.72 (d, J=4.3 Hz, 1H, CHOH), 4.44 (s, 1H, H-C(10)), 4.29 (s, 2H, CH2N), 3.76 (s, 6H, 2x OCH$_3$), 3.58 (m, 2H, ax-H-C(2')), 3.38 (m, 2H, eq-H-C(2')), 2.75 (q$_{AB}$, J$_{AB}$=15.4 Hz, 4H, citrate), 2.68 (s, 2H, H-C(11)), 1.9–1.5 (m, 5H, H-C(3'), H-C(4')). CIMS: m/z 456 ((M+H)$^+$, 12%) 439 (15), 438 (58), 113 (100).

EXAMPLE 21

(R,S)-1-[1-((9RS,10RS)-2-Chloro-9,10-dihydro-9,10-methanoanthracen-9-ylmethyl)-4-piperidyl]-1-(4-methoxyphenyl)methanol By a procedure similar to that described in Example 5, except using 4-bromoanisole in the lithiation procedure, and the piperidine aldehyde prepared as described in Example 5a, the citrate salt of the title compound was obtained as a white powder (48%), mp 119°–122° C.

Analysis for C$_{29}$H$_{30}$ClNO$_2$.C$_6$H$_8$O$_7$.0.4H$_2$O: Calculated: C, 63.75; H, 5.93; N, 2.12 Found: C, 63.74; M, 6.19; N, 1.85
$^1$H NMR (d$_6$-DMSO+TFA-d): δ 7.46 (s, 1H, H-C(1)), 7.32 (m, 3H), 7.23 (d, J=8.1 Hz, 2H), 7.03 (m, 3H), 6.91 (d, J=8.1 Hz, 2H), 4.47 (s, 1H, H-C(10)), 4.34 (brs, 1H, CHOH), 4.32 (q$_{AB}$, J$_{AB}$=13.9 Hz, 2H, CH$_2$N), 3.75 (s, 3H, OCH$_3$), 3.58 (m, 2H, ax-H-C(2')), 3.21 (m, 2H, eq-H-C(2')), 2.79 (q$_{AB}$, J$_{AB}$=14.5 Hz, 4H, citrate), 2.71 (q$_{AB}$, J$_{AB}$=8.9 Hz, 2H, H-C(11)), 1.87–1.59 (m, 5H, H-C(3'), H-C(4')). CIMS: m/z 462 ((M+H)$^+$, $^{37}$Cl, 17%) 461 ((M+H+1)$^+$, $^{35}$Cl, 17%), 462 ((M+H)$^+$, $^{35}$Cl, 53%), 442 (37), 189 (42), 175 (65), 143 (100), 113 (74).

EXAMPLE 22

(R,S)-1-[1-(9,10-Dihydro-9,10-methanoanthracen-9-ylmethyl)-4-piperidyl]-1-(3-methylphenyl)methanol By a procedure similar to that described in Example 5, except using 3-bromotoluene in the lithiation procedure, and the piperidine aldehyde prepared as described in Example 6a, the hydrochloride salt of the title compound was obtained as a white powder (26%), mp 180°–185° C.

Analysis for C$_{29}$H$_{31}$NO.1.0HCl.0.35H$_2$O: Calculated: C, 77.00; H, 7.28; N, 3.09 Found: C, 77.02; H, 7.27; N, 3.06
$^1$H NMR (d$_6$-DMSO+TFA-d): δ 7.32 (m, 4H), 7.13 (m, 4H), 6.98 (m, 4H), 4.43 (s, 1H, H-C(10)), 4.34 (d, J=5.1 Hz, 1H, CHOH), 4.29 (s, 2H, CH2N), 3.57 (m, 2H, ax-H-C(2')), 3.22 (m, 2H, eq-H-C(2')), 2.68 (s, 2H, H-C(11)), 2.30 (s, 3H, CH3), 1.84–1.65 (m, 5H, H-C(3'), H-C(4')). CIMS: m/z 411 ((M+H+1)$^+$, 31%), 410 ((M+H)$^+$, 100), 409 (24), 408 (17), 392 (32).

EXAMPLE 23

(R,S)-1-[1-((9RS, 10RS)
-2-Chloro-9,10-dihydro-9,10-methanoanthracen-9-
ylmethyl)-4-piperidyl]-1-(3-methylphenyl)methanol By a procedure similar to that described in Example 5, except using 3-bromotoluene in the lithiation procedure, and the piperidine aldehyde prepared as described in Example 5a, the hydrochloride salt of the title compound was obtained as a white powder (30%), mp 273°–277° C.

Analysis for $C_{29}H_{30}ClNO.1.0HCl.0.25H_2O$: Calculated: C, 71.82; H, 6.55; N, 2.89 Found: C, 71.86; H, 6.48; N, 2.80
$^1$H NMR ($d_6$-DMSO+TFA-d): δ 7.47 (s, 1H, H-C(1')), 7.33 (m, 3H), 7.23 (m, 1H), 7.06 (m, 6H), 4.47 (s, 1H, H-C(10)), 4.36 (m, 3H, CHOH, CH2N), 3.59 (m, 2H, ax-H-C(2')), 3.22 (m, 2H, eq-H-C(2')), 2.72 (s, 2H, H-C(11)), 2.34–1.66 (m, 5H, H-C(3'), H-C(4')). CIMS: m/z 447 ((M+H+1)$^+$, $^{37}$Cl, 12%) 446 ((M+H)$^+$, $^{37}$Cl, 39), 445 ((M+H+1)$^{30}$, $^{35}$Cl, 32) 444 ((M+H)$^+$, $^{35}$Cl, 100) 428 (17) 426 (48).

EXAMPLE 24

(R,S)-1-[1-(9,10-Dihydro-9,10-methanoanthracen-9-
ylmethyl)-4-piperidyl]-1-(1
-methylimidazol-2-yl)methanol A solution of n-butyllithium (1.81 mL of a 2.3M solution in hexanes, 4.16 mmol) in tetrahydrofuran (10 mL) was cooled to −65° C. and treated dropwise with 1-methylimidazole (310 mg, 3.78 mmol). The reaction mixture was allowed to warm to −20° C. and was stirred for 15 min. Following cooling to −65° C., a solution of piperidine aldehyde (600 mg, 1.89 mmol), prepared as described in Example 6a, in tetrahydrofuran (4 mL). The mixture was stirred at −65° C. for 1 h, then was poured into water (20 mL) and extracted with chloroform (3×50 mL). The organic extracts were washed sequentially with 10% aqueous sodium hydroxide (20 mL) and brine (20 mL), combined, dried ($K_2CO_3$), filtered and evaporated to leave an amber oil (920 mg). Purification by flash chromatography over silica gel (eluant: 960:40:1 chloroform/methanol/ammonium hydroxide) gave the title compound as a white powder (490 mg, 1.23 mmol, 63%). A solution of the free base in ether (25 mL) was treated with hydrogen chloride (g) to generate the hydrochloride salt as a white powder, mp 208°–215° C.

Analysis for $C_{26}H_{29}N_3O.2.0HCl.2.2H_2O$: Calculated: C, 60.98; H, 6.97; N, 8.21 Found: C, 60.81; H, 6.78; N, 8.23
$^1$H NMR ($d_6$-DMSO+TFA-d): δ 7.70 (s, 1H, H-C(4")), 7.64 (s, 1H, H-C(5")), 7.35 (m, 4H), 7.00 (m, 4H), 4.99 (d, J=5.6 Hz, 1H, CHOH), 4.46 (s, 1H, H-C(10)), 4.37 (s, 2H, CH2N), 3.91 (s, 3H, NCH$_3$), 3.60 (m, 2H, ax-H-C(2')), 3.31 (m, 2H, eq-H-C(2')), 2.75 (s, 2H, H-C(11)), 2.2–1.5 (m, 5H, H-C(3'), H-C(4')) CIMS: m/z 401 ((M+H+1)$^+$, 26%) 400 ((M+H)$^+$, 100%), 83 (37).

EXAMPLE 25

(R,S)-1-[1-(9,10-Dihydro-9,10-methanoanthracen-9-
ylmethyl)-4piperidyl]-1-(1
-methylbenzimidazol-2-yl)methanol.

By a procedure similar to that described in Example 24, except using 1-methylbenzimidazole in the lithiation step, and the piperidine aldehyde prepared as in Example 6a, the hydrochloride salt of the title compound was obtained as a white powder (47%), mp 222°–228° C.

Analysis for $C_{30}H_{31}N_3O.2.0HCl.1.0H_2$: Calculated: C, 66.66; H, 6.53; N, 7.77 Found: C, 66.84; H, 6.55; N, 7.33
$^1$H NMR ($d_6$-DMSO+TFA-d): δ 8.00 (m, 1H, H-C(4")), 7.81 (m, 1H, H-C(7")), 7.61 (m, 2H, H-C(5"), H-C(6")), 7.35 (m, 4H), 6.98 (m, 4H), 5.31 (d, J=4.5 Hz, 1H, CHOH), 4.45 (s, 1H, H-C(10)), 4.36 (s, 2H, CH2N), 4.11 (s, 3H, NCH$_3$), 3.56 (m, 2H, ax-H-C(2')), 3.30 (m, 2H, eq-H-C(2')), 2.73 (s, 2H, H-C(11)), 2.2–1.5 (m, 5H, H-C(3'), H-C(4')). CIMS: m/z 451 ((M+H+1)$^+$, 33%) 450 ((M+H)$^+$, 100%) 449 (17), 133 (12).

EXAMPLE 26

(R,S)-1-[1-(9,10-Dihydro-9,10-methanoanthracen-9-
ylmethyl)-4-piperidyl]-1-(1
-methyl-2-phenylimidazol-5-yl)methanol.

By a procedure similar to that described in Example 24, except using 1-methyl-5-phenylimidazole in the lithiation step, and the piperidine aldehyde prepared as in Example 6a, the hydrochloride salt of the title compound was obtained as a white powder (46%), mp 225°–229° C.

Analysis for $C_{32}H_{33}N_3O.2.0HCl.0.75H_2O$: Calculated: C, 68.38; H, 6,55; N, 7.48 Found: C, 68.45; H, 6.51; N, 7,42
$^1$H NMR ($d_6$-DMSO+TFA-d): δ 7.90 (s, 1H, H-C(4"), 7.84–7.70 (m, 5H, $C_6H_5$),, 7.37 (m, 4H), 7.01 (m, 4H), 4.62 (d, J=6.6 Hz, 1H, CHOH), 4.48 (s, 1H, H-C(10)), 4.41 (s, 2H, CH2N), 3.88 (s, 3H, NCH$_3$), 3.66 (m, 2H, ax-H-C(2')), 3.35 (m, 2H, eq-H-C(2')), 2.77 (s, 2H, H-C(11)), 2.2–1.5 (m, 5H, H-C(3'), H-C(4')). CIMS: m/z 477 ((M+H+1)$^+$, 14%), 476 ((M+H)$^+$, 41%) 459 (35) 458 (100) 457 (19), 320 (10), 231 (10) 203 (14).

EXAMPLE 27

(R,S)-1-[1-(9,10-Dihydro-9,10-methanoanthracen-9-
ylmethyl)-4-piperidyl]-1-(2-thiazolyl)methanol.

By a procedure similar to that described in Example 5, except using 2-bromothiazole in the lithiation step, and the piperidine aldehyde prepared as in Example 6a, the hydrochloride salt of the title compound was obtained as a white powder (50%), mp 192°–195° C.

Analysis for $C_{25}H_{26}N_2OS.1.0HCl.1.0H_2O$: Calculated: C, 65.70; H, 6.40; N, 6.13 Found: C, 65.48; H, 6.38; N, 5.98
$^1$H NMR ($d_6$-DMSO+TFA-d): δ 7.86 (d, J=3.3 Hz, 1H, H-C(4")), 7.71 (d, J=3.3 Hz, 1H, H-C(5")), 7.33 (m, 4H), 7.00 (m, 4H), 4.84 (d, J=4.5 Hz, 1H, CHOH), 4.45 (s, 1H, H-C(10)), 4.33 (s, 2H, CH2N), 3.61 (m, 2H, ax-H-C(2')), 3.32 (m, 2H, eq-H-C(2')), 2.71 (s, 2H, H-C(11)), 2.16–1.67 (m, 5H, H-C(3'), H-C(4')). CIMS: m/z 404 ((M+H+1)$^+$, 32%), 403 ((M+H)$^+$, 100%), 402(19), 401 (15), 385 (18).

EXAMPLE 28

(R,S)-1-[1-(9,10-Dihydro-9,10-methanoanthracen-9-
ylmethyl)-4-piperidyl]-1-(5-thiazolyl)methanol.

A solution of n-butyllithium (1.18 mL of a 2.3M solution in hexanes, 2.70 mmol) in tetrahydrofuran (10 mL) was cooled to <−70° C. and treated dropwise with a solution of 2-trimethylsilylthiazole (446 mg, 2.84 mmol) in tetrahydrofuran (2 mL). The resulting milky suspension was stirred at −70° C. for 0.5 h, then was treated with a solution of the piperidine aldehyde (600 mg, 1.89 mmol), prepared as described in Example 6a, in tetrahydrofuran (5 mL). The mixture was stirred at −70° C. for 0.5 h, then was warmed to room temperature and poured into 10% aqueous sodium hydroxide (25 mL). The aqueous mixture was extracted with ethyl acetate (3×50 mL). The organic extracts were washed sequentially with 10% aqueous sodium hydroxide (50 mL) and brine (25 mL), combined, dried ($K_2CO_3$), filtered and evaporated to afford (R,S)-1-[1-(9,10-Dihydro-9,10-methanoanthracen-9-ylmethyl)-4-piperidyl]-1-(2 -trimethylsilyl-5-thiazolyl)methanol as a dark foam (980 mg). The crude product was dissolved in methanol (50 mL) at 0° C., and the solution was treated with 1N hydrochloric acid (50 mL). The mixture was stirred at 0° C. for 2 h, then was concentrated to ca. 25 mL and poured into 10% aqueous sodium hydroxide (50 mL). The aqueous solution was extracted with chloroform (3×50 mL). The organic extracts were washed with brine (50 mL), combined, dried ($K_2CO_3$), filtered and evaporated to leave an amber foam (0.86 g). Purification by flash chromatography (eluant: 975:25:1 chloroform/methanol/ammonium hydroxide) afforded a white solid. A solution of this solid in diethyl ether (50 mL) was treated with hydrogen chloride (g) to afford the hydrochloride salt of the title compound (296 mg, 0.67 mmol, 36%) as a tan powder, mp 178°–183° C.

Analysis for $C_{25}H_{26}N_2OS1.0HCl.1.0H_2O$: Calculated: C, 65.70; H, 6.40; N, 6.13 Found: C, 65.60; H, 6.27; N, 5.90 $^1H$ NMR ($d_6$-DMSO+TFA-d): δ 9.53 (s, 1H, M-C(2")), 8.05 (s, 1H, H-C(4")), 7.35 (m, 4H), 7.00 (m, 4H), 4.85 (d, J=5.2 Hz, 1H, CHOH), 4.45 (s, 1H, H-C(10)), 4.34 (s, 2H, CH2N), 3.58 (m, 2H, ax-H-C(2')), 3.28 (m, 2H, eq-R-C(2')), 2.71 (s, 2H, H-C(11)), 1.92–1.65 (m, 5H, H-C(3'), H-C(4')). CIMS: m/z 404 ((M+H+1)$^+$, 30%), 403 ((M+H)$^+$, 100%), 402(22), 401 (12), 385 (20).

EXAMPLE 29

(R,S)-1-[1-(9,10-Dihydro-9,10-methanoanthracen-9-ylmethyl)-4-piperidyl]-1-(2 -N,N-dimethylaminomethylphenyl)methanol.

By a procedure similar to that described in Example 24, except using N,N-dimethylbenzylamine in the lithiation step, and the piperidine aldehyde prepared as in Example 6a, the hydrochloride salt of the title compound was obtained as a white powder (9%), mp 190°–195° C.

Analysis for $C_{31}H_{36}N_2O.2.8HCl.3.0H_2O$: Calculated: C, 61.16; H, 7.41; N, 4.60 Found: C, 61.11; H, 7.39; N, 4.78 $^1H$ NMR ($d_6$-DMSO+TFA-d): δ 7.46 (m, 8H), 6.99 (m, 4H), 4.69 (d, J=6.4 Hz, 1H, CHOH), 4.43 (s, 1H, H-C(10)), 3.55 (m, 2H, ax-H-C(2')), 3.22 (m, 2H, eq-H-C(2')), 2.85 (s, 3H, NCH3), 2.74 (s, 3H, NCH3), 2.72 (s, 2H, H-C(11)), 1.90 (m, 4H, H-C(3')), 1.47 (m, 1H, H-C(4')). CIMS: m/z 454 ((M+H+1)$^+$, 29%) 453 ((M+H)$^+$, 100) 435 (17) 407 (14).

EXAMPLE 30

(R,S)-1-[1-(9,10-Dihydro-9,10-methanoanthracen-9-ylmethyl)-4-piperidyl]-1-(2 -N,N-dimethylsulfamoylphenyl)methanol.

By a procedure similar to that described in Example 24, except using N,N-dimethylbenzenesulfonamide in the lithiation step, and the piperidine aldehyde prepared as in Example 6a, the hydrochloride salt of the title compound was obtained as a white powder (26%), mp 180°–185° C.

Analysis for $C_{30}H_{3}4N_2O_3S.1.0HCl.0.6H_2O$: Calculated: C, 65.52; H, 6.63; N, 5.09 Found: C, 65.50; H, 6.39; N, 4.93 $^1H$ NMR ($d_6$-DMSO+TFA-d): δ 7.75 (m, 3H), 7.50 (m, 1H), 7.32 (m, 4H), 6.98 (m, 4H), 5.26 (d, J=3.8 Hz, 1R, CHOH), 4.45 (s, 1H, H-C(10)), 4.30 (s, 2H, CH2N), 3.58 (m, 2H, ax-H-C(2')), 3.20 (m, 2H, q-H-C(2')), 2.73 (s, 6H, N(CH3)2), 2.70 (s, 2H, H-C(11)), 1.90 (m, H, H-C(3')), 1.39 (m, 1H, H-C(4')). CIMS: m/z 505 ((M+H+2)$^+$, 10%), 504 ((M+H+1)$^+$, 32) 503 ((M+H)$^+$, 100) 485 (26).

EXAMPLE 31

(R,S)-1-[1-(9,10-Dihydro-9,10-methanoanthracen-9-ylmethyl)-4-piperidyl]-1-(2 -(N,N-dimethylsulfamoyl)-3-methoxyphenyl)methanol.

By a procedure similar to that described in Example 24, except using N,N-dimethyl-2-methoxybenzenesulfonamide in the lithiation step, and the piperidine aldehyde prepared as in Example a, the hydrochloride salt of the title compound was obtained as a white powder (15%), mp 175°–180° C.

Analysis for $C_{31}H_{36}N_2O_4S.1.0HCl.0.5H_2O$: Calculated: C, 64.40; H, 6.62; N, 4.85 Found: C, 64.25; H, 6.75; N, 4.4 $^1H$ NMR ($d_6$-DMSO+TFA-d): δ 7.56 (dd, J=8.1, 8.1 Hz, H-C(5"), 7.40 (m, 1H), 7.34 (m, 4H), 7.13 (d, J=8.1 Hz, H-C(4")), 6.97 (m, 4H), 5.64 (s, 1H, CHOH), 4.44 (s, 1H, H-C(10)), 4.29 (s, 2H, CH2N), 3.90 (s, 3H, OCH3), 3.59 (m, 2H, ax-H-C(2')), 3.21 (m, 2H, .Q-H-C(2')), 2.78 (m, 6H, N(CH3)2), 2.71 (s, 2H, H-C(11)), 2.20–1.59 (m, 5H, H-C(3'), H-C(4')). CIMS: m/z 535 ((M+H+2)$^+$, 11%) 534 ((M+H+1)$^+$, 33), 533 ((M+H)$^+$, 100) 515 (12).

EXAMPLE 32

(R,S)-1-{1-((9RS, 10RS)-2-Chloro-9,10-dihydro-9,10-methanoanthracen-9-ylmethyl)-4 -piperidyl]-1-(2-(N,N-dimethylsulfamoyl)-5-methoxyphenyl)methanol.

By a procedure similar to that described in Example 24, except using N,N-dimethyl-4-methoxybenzenesulfonamide in the lithiation step, and the piperidine aldehyde prepared as in Example 5a, the hydrochloride salt of the title compound was obtained as a white powder (45%), mp 201°–206° C.

Analysis for $C_{31}H_{35}ClN_2O_4S.1.0HCl.0.5H_2O$: Calculated: C, 60.78; H, 6.09; N, 4.57 Found: C, 60.92; H, 6.19; N, 4.05 $^1H$ NMR ($d_6$-DMSO+TFA-d): δ 7.75 (d, J=8.9 Hz, 1H, H-C(3")), 7.47 (s, 1H, H-C(1)), 7.31 (m, 4H), 7.03 (m, 4H), 5.21 (d, J=3.0 Hz, CHOH), 4.47 (s, 1H, H-C(10)), 4.31 ($q_{AB}$, $J_{AB}$=14.5 Hz, 2H, CH2N), 3.67 (s, 3H, OCH3), 3.58 (m, 2H, ax-H-C(2')), 3.25 (m, 2H, eq-H-C(2')), 2.73 (m, 2H, H-C(11)), 2.66 (s, 6H, N(CH3)2), 1.95–1.48 (m, 5H, H-C(3'), H-C(4')). CIMS: m/z 570 ((M+H+1)$^{+37}$Cl, 11%), 569 ((M+H)$^+$, $^{37}$Cl, 37%) 568 ((M+H+1)$^+$, $^{35}$Cl, 32) 567 ((M+H)$^+$, $^{35}$Cl, 100) 549 (18).

EXAMPLE 33

(R,S)-1-[1-(9,10-Dihydro-9,10-methanoanthracen-9-ylmethyl)-4-piperidyl]-1-(2 -(N,N-dimethylsulfamoyl)-5-methoxyphenyl)methanol.

By a procedure similar to that described in Example 24, except using N,N-dimethyl-4-methoxybenzenesulfonamide in the lithiation step, and the piperidine aldehyde prepared as in Example 6a, the hydrochloride salt of the title compound was obtained as a white powder (26%), mp 185°–190° C.

Analysis for $C_{31}H_{36}N_2O_4S.1.0HCl.0.5H_2O$: Calculated: C, 64.40; H, 6.62; N, 4.85 Found: C, 64.22; H, 6.43; N, 4.70 $^1H$ NMR ($d_6$-DMSO+TFA-d): δ 7.73 (d, J=8.9 Hz, 1H, H-C(3")), 7.33 (m, 4H), 7.27 (d, J=2.7 Hz, 1H, H-C(6")), 7.05 (dd, J=2.7, 8.9 Hz, 1H, H-C(4")), 6.98 (m, 4H), 5.19 (d, J=4.1 Hz, 1H, CHOH), 4.45 (s, 1H, H-C(10)), 4.30 (s, 2H, CH$_2$N), 3.88 (s, 3H, OCH$_3$), 3.59 (m, 2H, ax-H-C(2')), 3.21 (m, 2H, eq-H-C(2')), 2.71 (s, 2H, H-C(11)), 2.67 (s, 6H, N(CH$_3$)$_2$), 1.95–1.48 (m, 5H, H-C(3'), H-C(4')). CIMS: m/z 534 ((M+H+1)$^+$, 25%), 533 ((M+H)$^+$, 100) 515 (17).

EXAMPLE 34

(R,S)-1-[1-(9,10-Dihydro-9,10-methanoanthracen-9-ylmethyl)-4-piperidyl]-1-(2-(N,N-dimethylsulfamoyl)-3,6-dimethoxyphenyl)methanol.

By a procedure similar to that described in Example 24, except using N,N-dimethyl-2,5-dimethoxybenzenesulfonamide in the lithiation step, and the piperidine aldehyde prepared as in Example 6a, the hydrochloride salt of the title compound was obtained as a white powder (18%), mp 201°–204° C.

Analysis for C$_{32}$H$_{38}$N$_2$O$_5$S.1.0HCl.0.75H$_2$O; Calculated: C, 62.73; H, 6.66; N, 4.57 Found: C, 63.02; H, 6.55; N, 4.49
$^1$H NMR (d$_6$-DMSO+TFA-d): δ 7.36 (m, 5H), 7.17 (d, J=9.2 Hz, 1H, H-C(4')), 6.99 (m, 4H), 5.57 (d, J=10.3 Hz, 1H, CHOH), 4.45 (s, 1H, H-C(10)), 4.32 (s, 2H, CH$_2$N), 3.67 (s, 3H, OCH$_3$), 3.65 (s, 3H, OCH$_3$), 3.59 (m, 2H, ax-H-C(2')), 3.20 (m, 2H, eq-H-C(2')), 2.73 (s, 2H, H-C(11)), 2.61 (s, 6H, N(CH$_3$)$_2$), 2.47–1.10 (m, 5H, H-C(3'), H-C(4')). CIMS: m/z 564 ((M+H+1)$^+$, 23%), 563 ((M+H)$^+$, 100), 545 (46).

EXAMPLE 35

(R,S)-1-[1-(9,10-Dihydro-9,10-methanoanthracen-9-ylmethyl)-4-piperidyl]-1-(2-(N,N-dimethylsulfamoyl)-5,6-dimethoxyphenyl)methanol.

By a procedure similar to that described in Example 24, except using N,N-dimethyl-3,4-dimethoxybenzenesulfonamide in the lithiation step, and the piperidine aldehyde prepared as in Example 6a, the hydrochloride salt of the title compound was obtained as a white powder (24%), mp 189°–195° C.

Analysis for C$_{32}$H$_{38}$N$_2$O$_5$S.1.0HCl.0.25H$_2$O; Calculated: C, 63.67; H, 6.59; N, 4.64 Found: C, 63.64; H, 6.56; N, 4.53
$^1$M NMR (d$_6$-DMSO+TFA-d): δ 7.57 (d, J=8.9 Hz, 1H, M-C(4")), 7.33 (m, 4H), 7.07 (d, J=8.9 Hz, 1H, H-C(3")), 6.99 (m, 4H), 5.09 (d, J=8.3 Hz, 1H, CHOH), 4.44 (s, 1H, H-C(10)), 4.32 (s, 2H, CH$_2$N), 3.91 (s, 3H, OCH$_3$), 3.88 (s, 3H, OCH$_3$), 3.65 (m, 1H, ax-H-C(2')), 3.53 (m, ax-H-C(2')), 3.25 (m, 2H, eq-H-C(2')), 2.73 (s, 6H, N(CH$_3$)$_2$), 2.70 (s, 2H, H-C(11)), 2.5–1.1 (m, 5H, H-C(3'), H-C(4')). CIMS: m/z 564 ((M+H+1)$^+$, 25%) 563 ((M+H)$^+$, 100), 545 (44).

EXAMPLE 36

(R,S)-1-[1-((9RS, 10RS)-2-Chloro-9,10-dihydro-9,10-methanoanthracen-9-ylmethyl)-4-piperidyl]-1-(2-N,N-dimethylsulfamoyl-3,6-dimethoxyphenyl)methanol.

By a procedure similar to that described in Example 24, except using N,N-dimethyl-2,5-dimethoxybenzenesulfonamide in the lithiation step, and the piperidine aldehyde prepared as in Example 5a, the hydrochloride salt of the title compound was obtained as a white powder (26%), mp 195°–200° C.

Analysis for C$_{32}$H$_{37}$C$_1$N$_2$O$_5$S.1.0HCl.0.75H$_2$O: Calculated: C, 59.39; H, 6.15; N, 4.33 Found: C, 59.34; H, 6.39; N, 4.07
$^1$H NMR (d$_6$-DMSO+TFA-d): δ 7.32 (m, 4H), 7.17 (d, J:9.2 Hz, 1H, H-C(4")), 7.01 (m, 3H), 5.56 (d, J=9.2 Hz, 1H, CHOH), 4.47 (s, 1H, H-C(10)), 4.32 (m, 2H, CH$_2$N), 3.87 (s, 3H, OCH$_3$), 3.85 (s, 3H, OCH$_3$), 3.60 (m, 1H, ax-H-C(2')), 3.51 (m, 1H, ax-H-C(2')), 3.28 (m, 1H, eq-H-C(2')), 3.15 (m, 1H, eq-H-C(2')), 2.80 (s, 6H, N(CH$_3$)$_2$), 2.73 (m, 2H, H-C(11)), 2.47–1.10 (m, 5H, H-C(3'), H-C(4')). CIMS: m/z 600 ((M+H+1)$^+$, $^{37}$Cl, 16) 599 ((M+H)$^+$, $^{37}$Cl, 43), 598 ((M+H+1 )$^+$, $^{35}$Cl, 34) 597 ((M+H)$^+$, $^{35}$Cl, 100) 581 (19) 580 (14), 579 (31).

EXAMPLE 37

(R,S)-1-[1-((9RS, 10RS)-2-Chloro-9,10-dihydro-9,10-methanoanthracen-9-ylmethyl)-4-piperidyl]-1-(2-N,N-dimethylsulfamoyl-5,6-dimethoxyphenyl)methanol.

By a procedure similar to that described in Example 24, except using N,N-dimethyl-3,4-dimethoxybenzenesulfonamide in the lithiation step, and the piperidine aldehyde prepared as in Example 5a, the hydrochloride salt of the title compound was obtained as a white powder (21%), mp 205°–208° C.

Analysis for C$_{32}$H$_{37}$ClN$_2$O$_5$S.1.0HCl-0.75H$_2$O: Calculated: C, 59.39; M, 6.15; N, 4.33 Found: C, 59.66; H, 5.98; N, 4.19
$^1$H NMR (d$_6$-DMSO+TFA-d): δ 7.59 (d, J=4.1 Hz, 1H, H-C(3")), 7.53, 7.36 (2s, 1H, H-C(1)), 7.33 (m, 3H), 7.19 (d, J=4.1 Hz, 1H, H-C(4")), 7.03 (m, 3H), 5.09 (d, J=4.1 Hz, 1H, CHOH), 4.48 (s, 1H, H-C(10)), 4.32 (m, 2H, CH$_2$N), 3.92 (s, 3H, OCH$_3$), 3.67 (s, 3H, OCH$_3$), 3.55 (m, 2H, ax-H-C(2')), 3.21 (m, 2H, eq-H-C(2')), 2.72 (s, 2H, H-C(11)), 2.71 (s, 6H, N(CH3)2), 2.40–1.10 (m, 5H, H-C(3'), H-C(4')). CIMS: m/z 600 ((M+H+1)$^+$, $^{37}$Cl, 13%) 599 ((M+H)$^+$, $^{37}$Cl, 40), 598 ((M+H+1)$^+$, $^{35}$Cl, 37), 597 ((M+H)$^+$, $^{35}$Cl, 100) 581 (16) 579 (42).

EXAMPLE 38

(R,S)-1-[1-((9RS, 10RS)-2-Chloro-9,10-dihydro-9,10-methanoanthracen-9-ylmethyl)-4-piperidyl]-1-(2-N,N-dimethylsulfamoylphenyl)methanol.

By a procedure similar to that described in Example 24, except using N,N-dimethylbenzenesulfonamide in the lithiation step, and the piperidine aldehyde prepared as in Example 5a, the hydrochloride sal of the title compound was obtained as a white powder (31%), mp 208°–212° C.

Analysis for C$_{30}$H$_{33}$ClN$_2$O$_3$.1.0HCl.0.5H$_2$O; Calculated: C, 61.85; H, 6.05; N, 4.80 Found: C, 62.05; H, 5.92; N, 4.77
$^1$H NMR (d$_6$-DMSO+TFA-d): δ 7.79 (m, 2H), 7.69 (d, J=4.6 Hz, 1H, H-C(3"), 6.51 (d, J=8.1 Hz, 1H, H-C(6")), 7.45 (s, 1H, H-C(1)), 7.31 (m, 3H), 7.01 (m, 3H), 5.23 (s, 1H, CHOH), 4.46 (s, 1H, H-C(10)), 4.40 (q$_{AB}$, J$_{AB}$=14.2 Hz, 2H, CH$_2$N), 3.56 (m, 2H, ax-H-C(2')), 3.18 (m, 2H, eq-H-C(2')), 2.77 (s, 2H, H-C(11)), 2.72 (s, 6H N(CH$_3$)$_2$), 1.85–1.43 (m, 5H, H-C(3'), H-C(4')) CIMS: m/z 539 ((M+H)$^+$, $^{37}$Cl, 32%), 538 ((M+H+1)$^+$, $^{35}$Cl, 537 ((M+H)$^+$, $^{35}$Cl, 87), 519 (23), 354 (100).

EXAMPLE 39

(R,S)-1-[1-((9RS, 10RS)-2-Chloro-9,10-dihydro-9,10-methanoanthracen-9-ylmethyl)-4-piperidyl]-1-(2-N-methylsulfamoylphenyl)methanol.

By a procedure similar to that described In Example 24, except using N-methylbenzenesulfonamide in the lithiation step, and the piperidine aldehyde prepared as in Example 5a, the hydrochloride salt of the title compound was obtained as a white powder (31%), mp 217°–220° C.

Analysis for $C_{29}H_{31}ClN_2O_3 \cdot 1.0HCl \cdot 9.5H_2O$: Calculated: C, 61.26; H, 5.85; N, 4.93 Found: C, 61.19; H, 5.81; N, 4.82
$^1$H NMR (d$_6$-DMSO+TFA-d): δ 7.82 (m, 2H), 7.66 (m, 1H), 7.47 (m, 2H), 7.34 (m, 3H), 7.02 (m, 3H), 5.34 (d, J=3.6 Hz, 1H, CHOH), 4.47 (s, 1H, H-C(10)), 4.32 (q$_{AB}$, J$_{AB}$=14.2 Hz, 2H, CH$_2$N), 3.60 (m, 2H, ax-H-C(2')), 3.20 (m, 2H, eq-H-C(2')), 2.73 (s, 2H, H-C(11)), 2.51 (s, 3H, NHCH3), 1.95–1.45 (m, 5H, H-C(3'), H-C(4')). CIMS: m/z 526 ((H+H+1)$^+$, $^{37}$Cl, 11%) 525 ((M+H)$^+$, $^{37}$Cl, 39) 524 ((M+H+1)$^+$, $^{35}$Cl, 34) 523 ((M+H)$^+$, $^{35}$Cl, 100) 507 (22), 505 (45).

EXAMPLE 40

(R,S)-1-[1-(9,10-Dihydro-9,10-methanoanthracen-9-ylmethyl)-4piperidyl]-1-phenylmethanol.

A solution of the piperidine aldehyde (700 mg, 2.21 mmol), prepared as in Example 6a, in dry tetrahydrofuran (25 mL) was cooled to −10° C. and treated dropwise with a solution of phenylmagnesium chloride in tetrahydrofuran (1.65 mL of a 2.0M solution, 3.31 mmol). The resulting mixture was stirred at −10° C. for 3 h, then was quenched by careful addition of water (5 mL). The mixture was then poured into water (50 mL) and extracted with chloroform (3×50 mL). The organic extracts were washed sequentially with 1N aqueous sodium hydroxide (25 mL) and brine (25 mL), combined, dried over K$_2$CO$_3$, filtered and concentrated to leave an off white foam (0.98 g). Purification by flash chromatography (eluant: 3:1 hexane/acetone) afforded the desired alcohol (0.52 g) as an ivory solid. Treatment of this material with ethereal hydrogen chloride afforded white solids, which were reprecipitated from methanol/ether (1:30, 150 mL) to yield the hydrochloride salt (510 mg, 1.18 mmol, 53%) as a white solid, mp 178°–182° C.

Analysis for $C_{28}H_{29}NO \cdot 1.0HCl \cdot 0.25H_2O$: Calculated: C, 77.04; H, 7.04; N, 3.20 Found: C, 77.08; H, 6.96; N, 3.24
$^1$H NMR (d$_6$-DMSO+TFA-d): δ 7.32 (m, 9H), 7.00 (m, 4H), 4.44 (s, 1H, H-C(10)), 4.40 (d, J=5.2 Hz, 1H, CHOH), 4.31 (s, 2H, CH$_2$N), 3.59 (m, 2H, ax-H-C(2')), 3.22 (m, 2H, eq-H-C(2')), 2.68 (s, 2H, H-C(11)), 1.84–1.50 (m 5H, H-C(3'), H-C(4')) CIMS: m/z 397 ((M+H+1)$^+$, 31%) 396 ((M+H)$^+$, 100) 395 (11), 394 (11), 378 (32).

EXAMPLE 41

(R,S)-1-[1-((9RS, 10RS)-2-Chloro-9,10-dihydro-9,10-methanoanthracen-9-ylmethyl)-4-piperidyl]-1-phenylmethanol.

By a procedure similar to that described in Example 40, except using the piperidine aldehyde prepared as described in Example 5a, the hydrochloride salt of the title compound was obtained as a white powder (53%), mp 195°–197° C.

Analysis for $C_{28}H_{28}ClNO \cdot 1.0Cl \cdot 1.00H_2O$: Calculated: C, 69.41; H, 6.44; N, 2.89 Found: C, 69.45; H, 6.41; N, 2.71
$^1$H NMR (d$_6$-DMSO+TFA-d): δ 7.48 (s, 1H, H-C(1)), 7.34 (m, 8H), 7.02 (m, 3H), 4.46 (s, 1H, H-C(10)), 4.39 (d, J=5.2 Hz, 1H, CHOH), 4.32 (q$_{AB}$, J$_{AB}$=14.3 Hz, 2H, CH$_2$N), 3.57 (m, 2H, ax-H-C(2')), 3.21 (m, 2H, eq-H-C(2')), 2.71 (s, 2H, H-C(11)), 2.0–1.5 (m, 5H, H-C(3'), H-C(4')). CIMS: m/z 432 ((M+H)$^+$, $^{37}$Cl, 30%), 431 ((M+H+1)$^+$, $^{35}$Cl, 8%) 430 ((M+H)$^+$, $^{35}$Cl, 100), 428 (13), 412 (25).

EXAMPLE 42

(R,S)-1-[1-((9RS, 10RS)-2-Chloro-9,10-dihydro-9,10-methanoanthracen-9-ylmethyl)-4-piperidyl]-1-(4-chlorophenyl)methanol.

By a procedure similar to that described in Example 40, except using 4-chlorophenylmagnesium bromide and the piperidine aldehyde prepared as described in Example 5a, the hydrochloride salt of the title compound was obtained as a white powder (44%), mp 203°–213° C.

Analysis for $C_{28}H_{27}Cl_2NO \cdot 1.0HCl \cdot 0.8H_2O$: Calculated: C, 65.26; H, 5.78; N, 2.71 Found: C, 65.11; H, 5.85; N, 2.64
$^1$H NMR (d$_6$-DMSO+TFA-d): δ 7.46 (s, 1H, H-C(1)), 7.37 (m, 7H), 7.02 (m, 3H), 4.46 (s, 1H, H-C(10)), 4.44 (d, J=5.2 Hz, 1H, CHOH), 4.31 (q$_{AB}$, J$_{AB}$=14.2 Hz, 2H, CH$_2$N), 3.56 (m, 2H, ax-H-C(2')), 3.20 (m, 2H, eq-H-C(2')), 2.69 (s, 2H, H-C(11)), 2.0–1.5 (m, 5H, H-C(3'), H-C(4')). CIMS: m/z 467 ((M+H+1)$^+$, 35C137Cl, 15%), 466 ((M+H)$^+$, $^{35}$Cl$^{37}$Cl, 44%), 465 ((M+H+1)$^+$, $^{35}$Cl$^{35}$Cl, 35%), 464 ((M+H)$^+$, $^{35}$Cl$^{35}$Cl, 100), 448 (18), 446 (32).

EXAMPLE 43

(R,S)-1-[1-(9,10-Dihydro-9,10-methanoanthracen-9-ylmethyl)-4-piperidy]-1-(4-chlorophenyl)methanol.

By a procedure similar to that described in Example 40, except using 4-chlorophenylmagnesium bromide and the piperidine aldehyde prepared as described in Example 6a, the hydrochloride salt of the title compound was obtained as a white powder (38%), mp 193°–197° C.

Analysis for $C_{28}H_{28}ClNO \cdot 1.0HCl \cdot 1.0H_2O$: Calculated: C, 69.41; H, 6.44; N, 2.89 Found: C, 69.51; H, 6.27; N, 2.77
$^1$H NMR (d$_6$-DMSO+TFA-d): δ 7.36 (m, 8H), 7.00 (m, 4H), 4.44 (s, 1H, H-C(10)), 4.43 (d, J=5.2 Hz, 1H, CHOH), 4.30 (s, 2H, CH2N), 3.56 (m, 2H, ax-H-C(2')), 3.22 (m, 2H, eq-H-C(2')), 2.66 (s, 2H, H-C(11)), 1.9–1.5 (m, 5H, H-C(3'), H-C(4')) CIMS: m/z 432 ((M+H)$^+$, $^{37}$Cl, 38%), 431 ((M+H+1)$^+$, $^{35}$Cl, 38%), 430 ((M+H)$^+$, $^{35}$Cl, 100), 429 (21), 428 (16), 412 (38).

EXAMPLE 44

(R,S)-1-[1-(9,10-Dihydro-9,10-methanoanthracen-9-ylmethyl)-4-piperidyl-1-(4-fluorophenyl)methanol.

By a procedure similar to that described in Example 40, except using 4-fluorophenylmagnesium bromide and the piperidine aldehyde prepared as described in Example 6a, the hydrochloride salt of the title compound was obtained as a white powder (36%), mp 200°–201° C.

Analysis for $C_{28}H_{28}FNO \cdot 0.6H_2O$: Calculated: C, 79.25; H, 6.93; N, 3.30 Found: C, 79.08; H, 6.63; N, 3.28
$^1$H NMR (d$_6$-DMSO+TFA-d): δ 7.34 (m, 6H), 7.15 (m, 2H, H-C(3")), 6.99 (m, 4H), 4.44 (s, 1H, H-C(10)), 4.41 (d, J=5.4 Hz, 1H, CHOH), 4.32 (s, 2H, CH$_2$N), 3.59 (m, 2H, ax-H-C(2')), 3.22 (m, 2H, eq-H-C(2')), 2.68 (s, 2H, H-C(11)), 1.9–1.5 (m, 5H, H-C(3'), H-C(4')). CIMS: m/z 415 ((M+H+

1)+, 32%) 414 ((M+H)+, 100) 413 (18), 412 (15), 396 (34).

EXAMPLE 45

1-((9RS,10RS)-2-Chloro-9,10-dihydro-9,10-methanoanthracen-9-ylmethyl)-4-(3-pyridoyl)piperidine A solution of (R,S)-1-[1-((9RS,10RS)-2-chloro-9,10-dihydro-9,10-methanoanthracen-9 -ylmethyl)-4-piperidyl]-1-(3pyridyl)methanol (1.00 g, 2.32 mmol), prepared as described in Example 5a, in dichloromethane (50 mL) was treated with manganese (IV) oxide (2.01 g, 23.2 mmol). The heterogeneous mixture was stirred vigorously for 16 h at room temperature. An additional quantity (1.00 E, 11.6 mmol) of manganese (IV) oxide was added, and the mixture was stirred for an additional 72 h. The solids were removed by filtration through Celite and were washed with dichloromethane (3×25 mL). The filtrate was evaporated to leave a pale yellow foam (700 mg). This was purified by flash chromatography (eluant: 1% methanol, 0.1% ammonium hydroxide, chloroform) to give a pale yellow foam (538 mg). The hydrochloride salt was prepared in methanol (10 mL) and was precipitated from ether (300 mL) to afford the title compound (281 mg, 0.61 mmol, 26%) as a white powder, mp 220°–225° C.

Analysis for $C_{27}H_{25}ClN_2O \cdot 1.0HCl \cdot 1.0H_2O$: Calculated: C, 67.08; H, 5.84 l N, 5.79 Found: C, 66.94; H, 5.60; N, 5.74
$^1$H NMR ($d_6$-DMSO+TFA-d): δ 9.50 (d, J=1.9 Hz, 1H, H-C(2'')), 9.12 (dd, J=1.4, 5.6 Hz, 1H, H-C(6'')), 8.96 (ddd, J=1.4, 1.9, 8.2 Hz, 1H, H-C(4'')), 8.14 (dd, J=5.6, 8.2 Hz, 1H, H-C(5'')), 7.52 (d, J=1.8 Hz, 1H, H-C(1)), 7.35 (m, 3H), 7.01 (m, 3H), 4.51 (s, 1H, H-C(10)), 4.49 ($q_{AB}$, $J_{AB}$=14.5 Hz, 2H, CH$_2$N), 3.83 (m, 1H, H-C(4')), 3.72 (m, 2H, eq-H-C(2')), 3.48 (m, 2H, ax-H-C(2')), 2.77 (brs, 2H, H-C(11)), 2.15–1.75 (m, 4H, H-C(3')). CIMS: m/z 431 ((M+H)+, $^{37}$Cl, 45%), 430 ((M+H+1)+, $^{35}$Cl, 21), 429 ((M+H)+, $^{35}$Cl, 100).

EXAMPLE 46

(R,S)-1-[1-((9S, 10S)-2-Chloro-9,10-dihydro-9,10-methanoanthracen-9-ylmethyl)-4-piperidyl]-1-(3-pyridyl)ethanol.

A solution of the amide (R,S)-1-[1-((9S,10S)-2-chloro-9,10-dihydro-9,10-methanoanthracen-9 -ylcarbonyl)-4-piperidyl]-1-(3-pyridyl)ethanol (1.20 g, 2.61 mmol) in tetrahydrofuran (30 mL) was treated seqentially with boron trifluoride etherate (390 mg, 2.74 mmol) and borane-methyl sulfide (0.58 mL of a 10.0M solution, 5.75 mmol). The mixture was heated to reflux for 22 h, then was cooled to room temperature and quenched by addition of methanol (10 mL) and 10% hydrochoric acid (5 mL). The mixture was then heated to reflux for 3 h. After cooling to room temperature, the mixture was poured into 10% aqueous sodium hydroxide (25 mL) and extracted with chloroform (3×35 mL). The organic extracts were washed with 1N aqueous sodium hydroxide (25 mL) and brine (25 mL), combined, dried ($K_2CO_3$), filtered and evaporated to leave an off white foam (1.24 g). Purification by flash chromatography over silica gel (eluant 2:1 hexane/acetone) afforded the title compound (620 mg, 1.29 mmol, 53%) as a white powder mp 108°–111° C.

Analysis for $C_{28}H_{29}ClN_2O \cdot 0.3H_2O$: Calculated: C, 74.67; H, 6.62; N, 6.22 Found: C, 74.50; H, 6.95; N, 5.94
$^1$H NMR ($d_6$-DMSO+TFA-d): δ 8.93 (m, 2H, H-C(2''), H-C(6'')), 8.67 (d, J=8.4 Hz, 1H, H-C(4'')), 8.13 (dd, J=5.7, 8.4 Hz, 1H, H-C(5'')), 7.47 (m, 1H, H-C(1)), 7.33 (m, 3H), 7.01 (m, 3H), 4.48 (s, 1H, H-C(10)), 4.36 ($q_{AB}$, $J_{AB}$=14.5 Hz, 2H, CH$_2$N), 3.68, 3.51 (2d, J=11.0 Hz, 2H, eq-H-C(2')), 3.18 (m, 2H, ax-H-C(2')), 2.70 ($q_{AB}$, $J_{AB}$=8.4 Hz, 2H, H-C(11)), 2.00–1.33 (m, 5H, H-C(3+), H-C(4')), 1.59 (s, 3H, CH$_3$).
CIMS: m/z 447 ((M+H)+, $^{37}$Cl, 100), 427 (16).

The starting amide was prepared as follows:
a. (R,S)-1-[1-((9S,10S)-2-Chloro-9,10-dihydro-9,10-methanoanthracen-9-ylcarbonyl)-4 -piperidyl]-1-(3-pyridyl)ethanol.

A solution of (9S,10S)-2-chloro-9,10-dihydro-9,10-methano-9-anthracenecarboxylic acid, prepared as in Example 11 (709 mg, 2.62 mmol) in dichloromethane (25 mL) was treated with oxalyl chloride (365 mg, 2.88 mmol) and N,N-dimethylformamide (10 mg, 0.14 mmol). The resulting solution was warmed to reflux temperature for 2 h, then was cooled to room temperature and the excess reagent was evaporated in vacuo. The residue was dissolved in tetrahydrofuran (20 mL), cooled to 0° C. and treated with 4-(1-methyl-1-(3-pyridyl)piperidine methanol (540 mg, 2.62 mmol) and triethylamine (291 mg, 2.88 mmol). The resulting mixture was stirred for 16 h at room temperature, then was poured into 1 N aqueous sodium hydroxide (20 mL) and extracted with ethyl acetate (3×50 mL) The organic phase was separated and washed sequentially with 1N aqueous sodium hydroxide (25 mL) and brine (25 mL), combined, dried over potassium carbonate, filtered and evaporated to leave an ivory solid (1.20 g, 2.61 mmol, 99%) This sample of amide was used directly without purification.

The piperidine derivative was prepared as follows:
b. 1-(Benzyloxycarbonyl)-4-piperidine carboxylic acid.

A solution of isonipecotic acid (5.0 g, 38.72 mmol) in 10% aqueous sodium carbonate (100 mL) was cooled to 0° C. and treated with benzyl chloroformate (7.93 g, 46.75 mmol). The resulting biphasic mixture was allowed to warm to room temperature over 2 h, at which time it became homogeneous. The mixture was washed with ether (2×50 mL), then was acidified to pH-2 by addition of concentrated hydrochloric acid. The aqueous solution was extracted with ether (2×100 mL). The organic extracts were washed with brine (50 mL), combined, dried ($Na_2SO_4$), filtered and evaporated to afford the product as a clear oil which slowly crystallized on standing (9.64 g, 36.6 mmol, 95%).
$^1$H NMR (CDCl$_3$): δ 7.36 (m, 5H, C6H5), 5.13 (s, 2H, PhCH2), 4.10 (brd, J=12.6 Hz, 2H, eq-H-C(2)), 2.96 (brdd, J=11.2, 12.6 Hz, 2H, ax-H-C(2)), 2.52 (m, 1H, H-C(4)), 1.93 (brd, J=10.8 Hz, 2H, eq-H-C(3)) 1.70 (m 2H ax-H-C(3)). CIMS: m/z 264 ((M+H)+, 22%), 220 (15), 167 (20), 149 (19), 91 (100).

c. N-Methoxy-N-methyl 1-(Benzyloxycarbonyl)piperidine carboxamide.

A solution of 1-(benzyloxycarbonyl)-4-piperidine carboxylic acid (2.0 g, 7.60 mmol), N,O-dimethylhydroxylamine hydrochloride (890 mg, 9.11 mmol), 1-(3-dimethylaminopropyl)-3-ethylcarbodiimide hydrochloride (1.75 g, 9.11 mmol), 4-dimethylaminopyridine (93 mg, 0.76 mmol) and triethylamine (2.31 g, 22.8 mmol) in dichloromethane (50 mL) was stirred at room temperature for 22 h. The mixture was then poured into 2N hydrochloric acid (50 mL) and extracted with ethyl acetate (3×100 mL). The organic extracts were washed sequentially with 2N hydrochloric acid (50 mL), 10% aqueous sodium bicarbonate (50 mL) and brine (50 mL), combined, dried (Na2SO4), filtered and evaporated to afford the amide as a clear syrup (1.97 g, 6.43 mmol, 85%).
$^1$ NMR (CDCl$_3$): δ 7.35 (m, 5H, C$_6$H$_5$), 5.13 (s, 2H, PhCH$_2$), 4.25 (br, 2H), 3.71 (s, 3H, OCH$_3$), 3.19 (s, 3H, NCH$_3$), 2.86

(br, 3H), 1.71 (br, 4H).

d. 1-(Benzyloxycarbonyl)-4-(3-pyridoyl)piperidine:

A solution of n-butyllithium (3.06 mL of a 2.5M solution in hexane, 7.63 mmol) in tetrahydrofuran (25 mL) was cooled to <–80° C. and treated dropwise with a solution of 3-bromopyridine (1.27 g, 8.01 mmol) in tetrahydrofuran (10 mL). The resulting pale yellow solution was stirred at <–80° C. for 15 minutes, then was treated with a solution of N-methoxy-N-methyl 1-(benzyloxycarbonyl) piperidine carboxamide (1.95 g, 6.36 mmol) in tetrahydrofuran (10 mL). The reaction was allowed to warm to –60° C. over 30 minutes, then was quenched by addition of water (20 mL) and extracted with ethyl acetate (3×75 mL). The organic extracts were washed sequentially with 1N aqueous sodium hydroxide (50 mL) and brine (50 mL), combined, dried ($K_2CO_3$), filtered and evaporated to leave an amber oil (2.07 g). Purification by flash chromatography over silica gel (eluant: 2:1 hexane/acetone) afforded the title ketone (1.30 g, 4.01 mmol, 63%) as an off white foam.

$^1$H NMR (CDCl$_3$): δ 9.14 (d, J=2.1 Hz, 1H, H-C(2')), 8.78 (dd, J=1.6, 4.8 Hz, 1H, H-C(6')), 8.20 (ddd, J=1.6, 2.1, 8.0 Hz, 1H, H-C(4')), 7.43 (dd, J=4.8, 8.0 Hz, 1H, H-C(5')), 7.34 (m, 5H, C$_6$H$_5$), 5.14 (s, 2H, PhCH$_2$), 4.24 (brd, J=11.4 Hz, 2H, eq-H-C(2)), 3.38 (m, 1H, H-C(4)), 3.00 (dd, J=11.4, 11.5 Hz, 2H, ax-H-C(2)), 1.95–1.60 (m, 4H, H-C(3) ).

e. (R,S)-1-(1-Benzyloxycarbonylpiperidin-4-yl)-1-(3-pyridyl)ethanol.

A solution of 1-(benzyloxycarbonyl)-4-(3-pyridoyl)piperidine (1.28 g, 3.95 mmol) in tetrahydrofuran (20 mL) was cooled to –65° C. and treated dropwise with methyllithium (2.96 mL of a 1.4M solution in diethyl ether, 4.15 mmol). The resulting mixture was stirred and warmed to room temperature over 2 h. The mixture was quenched by addition of rarer (10 mL), then was poured into 10% aqueous sodium hydroxide (5 mL) and extracted with ethyl acetate (3×50 mL). The organic extracts were washed sequentially with 10% aqueous sodium hydroxide (20 mL) and brine (20 mL), combined, dried (Na2S04), filtered and evaporated to leave a yellow foam. Purification by flash chromatography (eluant: 2:1→1:1 hexane/acetone) afforded the title alcohol (1.02 g, 3.00 mmol, 76%) as a white foam.

$^1$H NMR (CDCl$_3$): δ 8.60 (d, J=1.9 Hz, 1H, H-C(2')), 8.44 (dd, J=1.5, 4.8 Hz, 1H, H-C(6')), 7.74 (ddd, J=1.5, 1.9, 8.0 Hz, 1H, H-C(4')), 7.33 (m, 5H, C$_6$H$_5$), 7.25 (dd, J=4.8, 8.0 Hz, 1H, H-C(5')), 5.08 (s, 2H, PhCH$_2$), 4.25 (br, 2H, eq-H-C(2)), 3.0–2.6 (br, 3H), 1.71 (m 2H), 1.57 (s, 3H, CH$_3$), 1.26 (m, 2H).

f. (R,S)-1-(4-Piperidyl)-1-(3-pyridyl)ethanol.

A solution of (R,S)-1-(1-benzyloxycarbonylpiperidin-4-yl)-1-(3-pyridyl)ethanol (1.02 g, 3.00 mmol) in ethanol (15 mL) was added to a suspension of 10% palladium on carbon (110 mg) in ethanol (5 mL). The mixture was placed under an atmosphere of hydrogen (50 psi) and shaken for 4 h. The catalyst was then removed by filtration through Celite and the filter cake was washed with ethanol (3×25 mL). The filtrate was evaporated to leave a clear oil. Trituration with diethyl ether (20 mL) induced crystallization of the oil, which upon evaporation of the ether afforded the title compound (600 mg, 2.91 mmol, 97%) as a white powder mp 127°–130° C.

$^1$H NMR (d$_6$-DMSO): δ 8.59 (s, 1H, H-C(2')), 8.40 (d, J=4.7 Hz, 1H, H-C(6')), 7.74 (brd, J=7.8 Hz, 1H, H-C(4')), 7.31 (dd, J=4.7, 7.8 Hz, 1H, H-C(5')), 2.89 (brdd, J=13.7, 13.7 Hz, 2H, eq-H-C(2)), 2.32 (ddd, J=11.2, 11.2, 13.7 Hz, 2H, ax-H-C(2)), 1.55 (m, 1H, H-C(4)), 1.44 (s, 3H, CH$_3$), 1.28–0.98 (m, 4H, H-C(3)). CIMS: m/z 208 ((M+H+1)$^+$, 15%), 207 ((M+H)$^+$, 100), 189 (31).

EXAMPLE 47

(R,S)-1-[1-(9,10-Dihydro-9,10-methanoanthracen-9-ylmethyl)-4-piperidyl]-1-[5-hydroxymethyl-3-pyridyl]methanol.

To a cooled solution (–72° C.) of n-butyllithium (2.0M in hexane, 1.56 mL, 3.12 mmol) in tetrahydrofuran (25 mL) under nitrogen was added bromomesitylene (0.89 g, 2.92 mmol). The metal-halogen exchange reaction was stirred for 1 h over which time a white precipitate forms. At the end of this period, 3-bromo-5-(tertbutyldimethylsiloxymethyl)pyridine (0.89 g, 2.97 mmol) was added and stirred for 1 h. 1-(9,10-Dihydro-9,10-methanoanthracen-9-ylmethyl)-4-formylpiperidine (0.79 g, 2.40 mmol), prepared as in Example 6a, was added as a tetrahydrofuran solution (3 mL) and the reaction was allowed to warm to room temperature. After stirring for 2.5 h, the reaction was quenched with the addition of water (100 mL) and extracted with ethyl acetate (200 mL). The organic phase was washed with water (2×100 mL), dried (Na2SO4), filtered, and reduced to an oil. To a solution of this oil in tetrahydrofuran (10 mL) under nitrogen was added tetrabutylammonium fluoride (0.75 mL, 2.88 mmol, 2 eq). The solution was stirred for 3 h, diluted with water (100 mL) and extracted with ethyl acetate (2×100 mL). The combined organic extracts were dried over anhydrous sodium sulfate, filtered, and reduced to an oil. The residue was triturated with hot methylene chloride to yield 0.74 g (74%) of the title compound as a white solid. No additional purification was required. TLC analysis (R$_f$ 0.12, 5% methanol in ether).

$^1$H NMR (CDCl$_3$): δ 8.49 (s, 1H), 8.42 (s, 1H), 7.67 (s, 1H), 7.23 (m, 2H), 7.11 (m, 2H), 6.91 (m, 4H), 4.74 (s, 2H), 4.44 (d, J=7.4 Hz, 1H), 4.24 (s, 1H), 3.36 (s, 2H), 3.07 (m, 2H), 2.56 (s, 2H), 2.16 (m, 2H), 1.89 (m 1H) 1.35 (m, 4H) CIMS: m/z 427 ((M+H)$^+$, 100%) 409 (44).

The free base was dissolved in methylene chloride and treated with two equivalents of citric acid. The salt was precipitated with the addition of diethyl ether, filtered, rinsed with fresh ether, and dried in vacuo (room temperature, 10 pascal, 18 h) to afford the citrate of the title compound as a white solid, mp 190°–194° C. (dec).

Analysis for $C_{28}H_{30}N_2O_2.2C_6H_8O_7.0.3H_2O$ Calculated: C, 58.86; B, 5.751 N, 3.43 Found: C, 58.83; B, 5.841 N, 3.40 The starting silyloxypyridine derivative was prepared as follows:

a. 3-Bromo-5-(tertbutyldimethylsiloxymethyl)pyridine.

To a methylene chloride solution (20 mL) of 3-bromo-5-(hydroxymethyl)pyridine hydrochloride (1.00 g, 4.48 mmol) under nitrogen was added triethylamine (2.50 mL, 17.9 mmol) and t-butyldimethylsilyl chloride (0.75 g, 5.0 mmol). The resulting solution was heated to reflux for 18 h, cooled to room temperature and diluted with diethyl ether (200 mL). The organic phase was washed with 2.5N NaO H (1×100 mL), water (3×100 mL) and saturated brine (1×100 mL). The ether solution was dried (MgSO4), filtered, and reduced to an colorless oil. The procedure resulted in 1.10 g (81%) of the title compound. The product required no additional purification. TLC analysis (R$_f$ 0.19, ethyl acetate) CIMS: m/z 304 ((M+H)$^+$, 81Br, 96%), 302 ((M+H)$^+$, 79Br, 100).

b. 3-Bromo-5-(hydroxymethyl)pyridine.

To a toluene suspension (100 mL) of 5-bromonicotinic acid (15.00 g, 74.3 mmol) was added thionyl chloride (6.00 mL, 81.7 mmol). The suspension was heated to reflux monitoring gas evolution with a mineral oil bubbler. After 60 min the system became homogeneous and achieved a steady state condition with respect to gas evolution. The reaction was cooled to room temperature. Excess thionyl chloride and the solvent were removed in vacuo to yield solid acid chloride hydrochloride salt. In a separate flask sodium borohydride (9.10 g, 241 mmol) was added to absolute ethanol (200 mL) and cooled to −10° C. under nitrogen. The acid chloride was added in portions over 20 min maintaining the reaction temperature under 0° C. at all times. After the addition was complete, the reaction was warmed to room temperature and stirred for 1 h. Water (200 mL) was added and the aqueous phase extracted with diethyl ether (2×200 mL). The combined organic extracts were washed with water (100 mL), dried ($K_2CO_3$), and filtered. The product was precipitated as its hydrochloride salt by treating the solution with ethereal HCl. The solid was dried in vacuo (room temperature, 16 pascal, 7 h). to afford the hydrochloride salt of the title compound (10.04 g, 44.5 mmol, 60%). CIMS: m/z 190 ((M+H)$^+$, 81Br, 99%), 188 ((M+1)$^+$, 79Br, 100), 172 (24), 170 (25).

EXAMPLE 48

(R,S)-1-[1-((9RS,10RS)-2-Chloro-9,10-dihydro-9,10-methanoanthracen-9-ylmethyl)-4 -piperidyl]-1-[2-methoxy-3-pyridyl]methanol.

To a cooled solution (−72° C.) of t-butyllithium (1.7M, 4.60 mL, 7.89 mmol) in tetrahydrofuran (25 mL) under nitrogen was added bromomesitylene (0.55 mL, 3.60 mmol). The metal-halogen exchange reaction was stirred for 1 h at which time 2-methoxypyridine (0.50 mL, 3.80 mM, 1.4 eq) was added dropwise. The deprotonation was warmed to room temperature and stirred for 2 h prior to recooling to −72° C. 1-(9,10-Dihydro-9,10-methanoanthracen-9-ylmethyl)-4-formylpiperidine (1.00 g, 2.85 mmol), prepared as in Example 5a, was added as a tetrahydrofuran solution (10 mL). After completion of the addition, the reaction was warmed to room temperature and stirred for 18 h. Excess reagent was quenched with water (100 mL) and the aqueous phase extracted with ethyl acetate (2×100 mL). Combined organic extracts were dried ($Na_2SO_4$), filtered, and reduced to an oil. The crude reaction mixture was purified by flash chromatography over silica gel (100 mL, eluent: 30% ethyl acetate in hexane) to yield 0.530 g (40%) of the title compound. TLC analysis confirmed the purity of the product ($R_f$ 0.20, 30% ethyl acetate in hexane).
$^1$H NMR (CDCl$_3$): δ 8.06 (d, J=4.1 Hz, 1H), 7.51 (d, J=6.0 Hz, 1H), 7.23 (m, 1H), 7.12 (m, 3H), 6.91 (m, 4H), 4.56 (s, 1H), 4.27 (s, 1H), 3.96 (s, 3H), 3.48 (s, 2H), 3.29 (m, 2H), 3.77 (s, 2H), 2.46 (m, 2H), 1.87 (m, 3H), 1.36 (m 2H) CIMS: m/z 461 ((M+H)$^+$, 100%) 443 (39).

The free base was dissolved in methylene chloride and treated with one equivalent of citric acid. The salt was precipitated with the addition of ether, filtered, rinsed with fresh ether, and dried in vacuo (room temperature, 10 pascal, 18 h). The procedure yielded a white solid, mp 130–133 C.
Analysis for $C_{28}H_{29}ClN_2O_2 \cdot C_6H_8O_7 \cdot 1.8H_2O$ Calculated: C, 59.57; H, 5.97; N, 4.09 Found: C, 59.83; H, 5.76; N, 3.75.

EXAMPLE 49

(R,S)-1-[1-(9,10-Dihydro-9,10-methanoanthracen-9-ylmethyl)-4-piperidyl]-1-[2 -methoxy-3-pyridyl]methanol.

Using a procedure similar to that described in Example 48, except starting with 1-(9,10-dihydro-9,10-methanoanthracen-9-yl-methyl)-4-formylpiperidine, prepared as described in Example 6a, the hydrochloride salt of the title compound was obtained (19%), as a white solid, mp 95°–100° C. (dec). free base:
$^1$H NMR (CDCl$_3$): δ 8.05 (dd, J=1.8, 4.9 Hz, 1H), 7.50 (dd, J=1.9, 7.2 Hz, 1H), 7.21 (m, 2H), 7.13 (m, 2H), 6.91 (m, 5H), 4.46 (d, J=8.0 Hz, 1H), 4.24 (s, 1H), 3.96 (s, 3H), 3.35 (s, 2H), 3.00 (m, 2H), 2.57 (d, J=1.3 Hz, 2H), 2.13 (m, 2H), 1.87 (m, 1H), 1.70 (m, 2H), 1.37 (m, 2H). CIMS: m/z 427 ((M+1)$^+$, 100%), 409 (29).
Analysis for $C_{28}H_{30}N_2O_2 \cdot C_6H_8O_7 \cdot H_2O$ Calculated: C, 64.14; H, 6.33; N, 4.40 Found: C, 64.38; H, 6.32; N, 4.25.

EXAMPLE 50

(R*)-1-[1-((9S,10S)-2-Chloro-9,10-dihydro-9,10-methanoanthracen-9-ylmethyl)-4-piperidyl]-1-(3-pyridyl)ethanol.

A solution of the amide (R*)-1-[1-((9S,10S)-2-chloro-9,10dihydro-9,10-methanoanthracen-9 -ylcarbonyl)-4-piperidyl]-1-(3-pyridyl)ethanol (1.95 g, 4.25 mmol) in tetrahydrofuran (40 mL) was treated seqentially with boron trifluoride etherate (633 mg, 4.46 mmol) and borane-methyl sulfide (1.28 mL of a 10.0H solution, 12.75 mmol). The mixture was heated to reflux for 22 h. The reaction was then quenched by addition of methanol (10 mL) and 10% hydrochoric acid (5 mL). The mixture was then heated to reflux for 1 h. After cooling to room temperature, sodium hydroxide (s, 1.0 g) was added. After all of the solid had dissolved, the mixture was poured into 10% aqueous sodium hydroxide (25 mL) and extracted with chloroform (3×75 mL). The organic extracts were washed with 1N aqueous sodium hydroxide (25 mL) and brine (25 mL), combined, dried ($K_2CO_3$), filtered and evaporated to leave an off white foam (2.07 g). Purification by flash chromatography over silica gel (eluant 2:1 hexane/acetone) afforded the title compound (900 mg, 2.01 mmol, 47%) as a white powder, mp 193°–194° C. $α_D$=+63.2° (c= 0.98, CHCl3).

Analysis for $C_{28}H_{29}ClN_2O$: Calculated: C, 75.57; H, 6.56; N, 6.29 Found: C, 75.21; H, 6.91; N, 6.18
$^1$H NMR (d$_6$-DMSO+TFA-d): δ 8.93 (m, 2H, H-C(2"), H-C(6")), 8.67 (dd, J=1.5, 6.9 Hz, 1H, H-C(4")), 8.13 (dd, J=5.7, 8.1 Hz, 1H, H-C(5")), 7.46 (d, J=1.8 Hz, 1H, H-C(1)), 7.33 (m, 3H), 7.03 (m, 3H), 4.47 (s, 1H, H-C(10)), 4.35 (q$_{AB}$, J$_{AB}$=14.3 Hz, 2H, CH$_2$N), 3.66, 3.52 (2d, J=11.4 Hz, 2H, eq-H-C(2')), 3.17 (m, 2H, ax-H-C(2')), 2.69 (brs, 2H, H-C(11)), 1.96 (d, J=11.0 Hz, 2H, eq-M-C(3')), 1.70 (m, 1H, H-C(4')), 1.58 (s, 3H, CH3), 1.35 (m, 2H, ax-H-C(3')). CIMS: m/z 447 ((M=H)$^+$, 37Cl, 33%), 446 ((M+H+1)$^+$, $^{35}$Cl, 27) 445 ((M+H)$^+$, $^{35}$Cl, 100 ), 427 (14).

The starting amide was prepared as follows:
a. (R*)-1-[1-((9RS, 10RS)-2-Chloro-9,10-dihydro-9,10-methanoanthracen-9-ylcarbonyl)- 4-piperidyl]-1-(3-pyridyl)ethanol.

A solution of (9S,10S)-2-chloro-9,10-dihydro-9,10-methano-9-anthracenecarboxylic acid, prepared as in Example 11 (1.25 g, 4.61 mmol) in dichloromethane (20 mL) was treated with oxalyl chloride (731 mg, 5.76 mmol) and N,N-dimethylformamide (10 mg, 0.14 mmol). The resulting solution was warmed to reflux temperature for 2 h, then was cooled to room temperature and the excess reagent was evaporated in vacuo. The residue was dissolved in tetrahydrofuran (10 mL) and added dropwise to a solution of (R*)-1-(4-piperidyl)-1-(3-pyridyl)ethanol (950 mg, 4.61 mmol) and triethylamine (582 mg, 5.76 mmol) in tetrahydrofuran (15 mL) and dichloromethane (25 mL). The resulting mixture was stirred for 3 h at room temperature, then was poured into 1N aqueous sodium hydroxide (25 mL) and extracted with chloroform (3×100 mL) The organic extracts were washed sequentially with 1N aqueous sodium hydroxide (50 mL) and brine (50 mL), combined, dried over sodium sulfate, filtered and evaporated to leave a dark tan foam. Purification by flash chromatography (eluant: 1:1 hexane/acetone) afforded the title amide as an off white foam (2.00 g, 4.36 mmol, 95%). CIMS: m/z 461 ((M+H)$^+$, 37Cl, 33%), 460 ((M+H+1)$^+$, 35Cl, 28), 459 ((M+H)$^+$, 35Cl, 100)

The piperidine derivative was prepared as follows:

b. Optical Resolution of (R,S)-1-(4-piperidyl)-1-(3-pyridyl)ethanol.

A solution of (R,S)-1-(4-piperidyl)-1-(3-pyridyl)ethanol, prepared as in Example 46f, (3.72 g, 18.03 mmol) in ethanol (75 mL) was added to a solution of dibenzoyl-L-tartaric acid (6.46 g, 18.03 mmol) in ethanol (75 mL). The mixture was heated to reflux for 10 minutes, then was cooled to room temperature. The white crystalline solid which deposited upon cooling was removed by filtration and washed with ethanol (10 mL). This enriched diastereomeric salt was recrystallized twice from ethanol (325 mL, 275 mL) to afford the pure diastereomeric salt (3.55 g, 6.29 mmol, 35%). The pure diastereomeric salt was dissolved in 10% aqueous sodium hydroxide (12 mL) and saturated brine (6 mL), and was extracted with chloroform (12×25 mL). The organic extracts were combined, dried over sodium sulfate, filtered and evaporated to leave the free base as a white solid (1.23 g, 5.96 mmol). Recrystalliztion from toluene (40 mL) afforded the enantiomerically pure title compound (1.09 g, 5.28 mmol, 29% overall) as white needles, mp 161°–164° C. $\alpha_D$=+18.2° (c=3.07, MeOH). Enantiomeric excess as determined by HPLC on chiral stationary phase: 98.5%

Analysis for $C_{12}H_{18}N_2O$: Calculated: C, 69.87; H, 8.79; N, 13.58 Found: C, 69.99; M, 8.69; N, 13.41.

$^1$H NMR (d$_6$-DMSO): δ 8.59 (s, 1H, H-C(2')), 8.40 (d, J=4.8 Hz, 1H, H-C(6')), 7.75 (d, J=6.7 Hz, 1H, H-C(4')), 7.31 (dd, J=4.8, 6.7 Hz, 1H, H-C(5')), 4.99 (br, 1H, CHOH), 2.87 (m, 2H, eq-H-C(2)), 2.28 (m, 2H, ax-H-C(2)), 1.52 (m, 1H, H-C(4)), 1.44 (s, 3H, CH$_3$), 1.28–0.98 (m, 4H, H-C(3)). CIMS: m/z 208 ((M+H+1)$^+$, 19%), 207 ((M+H)$^+$, 100), 189 (43). HPLC analysis: Column: Chiralcel OD Eluant: 90% hexane/10% ethanol Flow: 1.0 mL/min Wavelength: 215 nm Retention times: (+) enantiomer 15.3 min/(−) enantiomer: 13.0 min.

EXAMPLE 51

(S*)-1-[1-((9S, 10S)-2-Chloro-9,10-dihydro-9,10-methanoanthracen-9-ylmethyl)-4-piperidyl]-1-(3-pyridyl)ethanol.

Using a procedure similar to that described in Example 50, except using (S*)-1-(4-piperidyl)-1-(3-pyridyl)ethanol in the amide formation step, the title compound was obtained as a white solid, mp The piperidine derivative was resolved as follows:

a. Optical Resolution of (R,S)-1-(4-piperidyl)-1-(3-pyridyl)ethanol, S* enantiomer.

The mother liquors obtained from recrystallizations to obtain the R* enantiomer, as described in Example 50b, were combined and the solvent evaporated to leave an off white foam (7.6 g). This solid was dissolved in 10% aqueous sodium hydroxide (20 mL) and saturated aqueous sodium chloride (10 mL). The free base was extracted into chloroform (12×50 mL). The combined chloroform extract was dried over sodium sulfate, filtered and evaporated to leave an off white solid (2.87 g). This was dissolved in absolute ethanol (58 mL) and added to a solution of dibenzoyl-D-tartaric acid (4.98 g, 13.9 mmol) in absolute ethanol (58 mL). The mixture was heated to reflux temperature, held for 10 min, then was cooled to room tempertaure. The crystalline salt was isolated by filtration, washed with ethanol and dried to afford the diastereomerically enriched salt (4.7 g). The salt was recrystallized trice from absolute ethanol (100 mL, 100 mL) to afford the pure diastereomeric salt (3.08 g, 5.46 mmol, 39%). The pure diastereomeric salt was dissolved in 10% aqueous sodium hydroxide (10 mL) and saturated brine (5 mL), and was extracted with chloroform (12×25 mL). The organic extracts were combined, dried over sodium sulfate, filtered and evaporated to leave the free base as a white solid (1.06 g, 5.15 mmol). Recrystalliztion from toluene (30 mL) afforded the enantiomerically pure title compound (860 mg, 4.17 mmol, 30% overall) as white needles, mp 161°–164° C. $\alpha_D$=−16.6° (c=2.05, MeOH). Enantiomeric excess as determined by HPLC on chiral stationary phase as described in Example 50b: >98%.

Analysis for $C_{12}H_{18}N_2O$: Calculated: C, 69.87; H, 8.79; N, 13.58 Found: C, 69.80; H, 9.09; N, 13.83

$^1$H NMR (d$_6$-DMSO): δ 8.59 (d, J=2.2 Hz, 1H, H-C(2')), 8.40 (dd, J=1.4, 4.8 Hz, 1H, H-C(6')), 7.75 (d, J=6.7 Hz, 1H, H-C(4')), 7.31 (dd, J=4.8, 6.7 Hz, 1H, H-C(5')), 4.97 (br, 1H, CHOH), 2.87 (m, 2H, eq-H-C(2)), 2.28 (m, 2H, ax-H-C(2)), 1.52 (m, 1H, H-C(4)), 1.44 (s, 3H, CH$_3$), 1.28–0.98 (m, 4H, H-C(3)). CIMS: m/z 208 ((M+H+1)$^+$, 14%) 207 ((M+H)$^+$, 100), 189 (38).

EXAMPLE 5

1-[1-(9,10-Dihydro-9,10-methanoanthracen-9-ylmethyl)-4-piperidyl]-1-(3-pyridyl)methanol.

A solution of 1-[1-(9,10-dihydro-9,10-methanoanthracen-9-ylmethyl)-4-piperidyl]-1-(3 -pyridyl)methanol, prepared as in Example 6, (292 g, 0.59 mmol) in tetrahydrofuran (12 mL) was treated with acetic anhydride (241 mg, 2.36 mmol), triethylamine (299 mg, 2.95 mmol), and 4-dimethylaminopyridine (7 mg, 0.06 mmol). The resulting mixture was stirred at room temperature for 24 h, then was partitioned between 10% aqueous sodium hydroxide and dichloromethane. The organic extract was separated and the aqueous was extractedwith dichloromethane (2X). The dichloromethane extracts were combined, dried over magnesium sulfate, filtered and concentrated on a rotary evaporator. The crude residue was crystallized from aqueous methanol (3 mL, 75%) to give the title compound as a white foamy solid (182 mg, 0.41 mmol, 70%), mp 127°–130° C.

Analysis for $C_{29}H_{30}N_2O_2$: Calculated: C, 79.40; H, 6.89; N, 6.39 Found: C, 79.41; H, 6.93; N, 6.29

$^1$H-NMR (d$_6$-DMSO): δ 8.50–8.48 (m, 2H), 7.72–7.70 (d, J=7.9 Hz, 1H),7.39–7.35 (dd, J=4.8 Hz, J=7.8 Hz, 1H), 7.26–7.24(m, 2H), 7.16–7.13 (m, 2H),6.94–6.86 (m, 4H), 5.48–5.45 (d, J=7.7 Hz, 1H), 4.29(s, 1H), 3.34–3.31(m, 2H), 3.03–2.93 (m, 2H), 2.42 (s, 2H), 2.13–2.04 (m, 5H), 1.73–1.68 (m, 2H), 1.23–1.16 (m, 3H). CIMS: m/z 440 ((M+H+1)$^+$, 24%), 439 ((M+H)$^+$, 100%), 438 (15%), 437 (11%) 380 (29%), 379 (98%).

EXAMPLE 53

1-(9,10-Dihydro-9,10-methanoanthracen-9-ylmethyl)-4-(3-pyridylmethyl)piperidine.

A solution of 1-[1-(9,10-dihydro-9,10-methanoanthracen-9-ylmethyl)-4-piperidyl]-1-(3 -pyridyl)methanol acetate, prepared as in Example 53, (175 mg, 0.40 mmol), ammonium formate (175 mg, 2.78 mmol), and 10% palladium on carbon (175 mg) were heated to reflux in methanol (6 mL) under nitrogen (g) for 8 h. Additional ammonium formate (175 mg, 2.78 mmol) was added and heating was continued for an additional 8 h. The suspension was filtered through celite and the solids were washed thoroughly with methanol and ethyl acetate. Concentration of the filtrate left an off white foam. Flash chromatography on silica using 3% methanol/dichloromethane gave the title compound as a colorless glass (100 mg, 0.26 mmol, 66%). This was dissolved in methanolic hydrogen chloride and concentrated from methanol (3×100 mL) to give the hydrochloride salt, mp 183°–185° C.

Analysis for $C_{27}H_{28}N_2.2.0HCl.0.8H_2O$: Calculated: C, 69.30; H, 6.81; N, 5.98 Found: C, 69.37; H, 6.63; N, 5.80
$^1$H-NMR ($d_6$-DMSO): δ 10.16(br s, 1H), 8.76–8.71(m, 2H), 8.26 (d, J=7.7 Hz, 1H), 7.85(dd, J=5.5 Hz, J=7.7 Hz, 1H), 7.41–7.30(m, 4H), 7.00–6.92(m, 4H), 4.44(s, 1H), 4.29(m, 2H), 3.50–3.46(m, 2H), 3.21(br m, 2H), 3.00–2.70(m, 4H), 1.83–1.70(m, 5H). CIMS: m/z 382 ((M+H+1)$^+$, 14%), 381 ((M+H)$^+$, 100%).

EXAMPLE 54

1-((9RS,10RS)-2-Chloro-9,10-dihydro-9,10-methanoanthracen-9-ylmethyl)-4-(3-pyridylmethyl)piperidine.

A solution of the amide (375 mg, 0.87 mmol) in tetrahydrofuran (10 mL) was treated with boron trifluoride etherate (135 mg, 0.96 mmol) and borane-tetrahydrofuran (3.32 mL of a 1.0M solution, 3.32 mmol). The resulting solution was heated to reflux for 0 h. The mixture was concentrated on a rotary evaporator to give a colorless residue. This residue was dissolved in methanol (5 mL) and concentrated hydrochloric acid (3 mL, 12N) was added. This solution was refluxed for 3 h and cooled to room temperature. Sodium hydroxide (1.5 g) was added with cooling and the mixture stirred for 1h. The mixture was partitioned between water (25 mL) and chloroform (50 mL). The organic extract was washed sequentially with aqueous sodium hydroxide (25 mL, 2.5N) and brine (25 mL). The organic extracts were combined, dried over sodium sulfate, filtered and evaporated to leave a colorless oil (800 mg). Flash chromatography on silica gel (eluant: 15% acetone/hexanes) afforded a clear oil (419 mg). This oil was treated with ethereal hydrogen chloride to give a white precipitate which was collected and washed with ether to give the hydrochloride salt of the title compound (194 mg, 0.43 mmol, 49%) as a white powder mp 204°–206° C.

Analysis for $C_{27}H_{27}ClN2.9HCl$: Calculated: C, 72.40; M, 6.28; N, 6.26 Found: C, 72.56; M, 6.35; N, 6.23
$^1$H-NMR ($d_6$-DMSO): δ 9.90 (br s, 0.5H, exchangable), 8.41 (s, 2H), 7.61 (m, 1H), 7.50–7.30 (m, 5H), 6.99 (br s, 3H), 4.46–4.00 (br m, 3H), 3.50–3.15 (br m, 4H), 2.75–2.50 (br m, 4H), 2.00–1.65 (br m, 5H) CIMS: m/z 418 ((M+H+1)$^+$, $^{37}$Cl, 13%), 417 ((M+H)$^+$, $^{37}$Cl, 40%) 416 ((M+H+1)$^+$, $^{35}$Cl, 33%), 415 (M+H)$^+$, $^{35}$Cl, 100%), 414 ( 18%), 413 (11%), 189 (14%).
The starting amide was prepared as follows:
a. 1-[(9RS,10RS)-2-Chloro-9,10-dihydro-9,10-methanoanthracen-9-ylcarbonyl)-4-(3-pyridylmethyl)piperidine.

A solution of 2-chloromethanoanthracene acid, prepared as in Example 1k, (540 mg, 2.00 mmol) in toluene (15 mL) was treated with thionyl chloride (298 mg, 2.50 mmol) and N,N-dimethylformamide (one drop). The resulting solution was heated to reflux for 2 h, then was cooled to room temperature and the excess reagent was evaporated in vacuo. The residue was dissolved in tetrahydrofuran (8 mL) and this solution was added to a stirred solution of 4-(3-pyridylmethyl)piperidine (300 mg, 1.70 mmol) in tetrahydrofuran (7 mL). A precipitate formed and the suspension was stirred for 16 h. Triethylamine (202 mg, 2.00 mmol) was added and the mixture was concentrated on a rotary evaporator. The resulting residue was partitioned between brine and dichloromethane. The dichloromethane extract was separated and the brine solution (pH>8) was reextracted two more times with dichloromethane. The dichloromethane extracts were combined, dried over sodium sulfate, filtered and concentrated on a rotary evaporator. Flash chromatography on silica gel (eluant: 30% acetone/hexanes) gave the title amide as a white foam (400 mg, 0.93 mmol, 55%).
$^1$H-NMR ($d_6$-DMSO): δ 8.42 (s, 2H), 7.64–7.60 (m, 2H), 7.45–7.30 (m, 4H), 7.02–6.99 (m, 3H), 4.66–4.61 (br m, 1H), 4.42(s, 1H), 3.69 (br m, 1H), 3.00–2.60 (m, 4H), 2.59–2.57 (m, 2H), 2.00–1.45 (m, 3H), 1.30–1.00 (m, 2H) CIMS: m/z 432 ((M+H+1)$^+$, $^{37}$Cl, 12%) 431 ((M+H)$^+$, $^{37}$Cl, 40%), 430 ((M+H+1)$^+$, 35Cl, 34%), 429 ((M+H)$^+$, $^{35}$Cl, 100%).
The piperidine derivative was prepared as follows:
b. 4-Piperidylmethanol.

A solution of ethyl isonipecotate (10.2 g, 64.6 mmol) in tetrahydrofuran (100 mL) was added dropwise to a suspension of lithium aluminum hydride (2.5 g, 65.9 mmol) in tetrahydrofuran held at reflux temperature. The resulting mixture was heated at reflux for 2 h, then was cooled to room temperature and stirred for 20 h. The mixture was cooled to 0° C. and quenched by sequential addition of water (2.5 mL), 10% aqueous sodium hydroxide (2.5 mL) and water (7.5 mL), then was stirred until a granular white precipitate formed. The mixture was then filtered through Celite, the solids washed with ethyl acetate (3×50 mL), and the filtrate concentrated to leave an oil. Trituration with petroleum ether (35–60) afforded the title compound as a white solid (7.26 g, 63.0 mmol, 97%).
c. 1-(1,1-Dimethylethyloxycarbonyl)-4-hydroxymethylpiperidine.

A solution of 4-hydroxymethylpiperidine (7.26 g, 63.0 mmol) in tetrahydrofuran (150 mL) was treated with di-tert-butyldicarbonate (20.62 g, 94.5 mmol). Vigorous evolution of carbon dioxide was observed, and the reaction was cooled in an ice water bath to keep the internal temperature below 30° C. The reaction mixture was stirred at room temperature for 4 h, then the solvent was evaporated. The residue was partitioned between water (100 mL) and diethyl ether (200 mL). The organic extract was separated and washed sequentially with 1N hydrochloric acid (2×100 mL), 10% aqueous sodium bicarbonate (100 mL) and brine (100 mL). Each aqueous wash was extracted with fresh diethyl ether (100 mL). The combined ether extract was dried over sodium sulfate, filtered and evaporated to have a clear oil which slowly crystallized. The solid product was triturated with hexane (100 mL), filtered and dried to afford a white solid (10.16 g, 47.2 mmol, 75%).
$^1$H NMR (CDCl$_3$): δ 4.11 (ddd, J=2.3, 2.5, 13.4 Hz, 2H, eq-H-C(2)), 3.48 (d, J=6.2 Hz, 2H, CH2OH), 2.70 (ddd, J=2.5, 13.0, 13.4 Hz, 2H, ax-H-C(2)), 2.44 (s, 1H, OH), 1.74–1.62 (m, 3H, eq-H-C(3), H-C(4)), 1.45 (s, 9H, (CH3)3C), 1.14 (m, 2H, ax-H-C(3)).
d. 1-(1,1-Dimethylethyloxycarbonyl)-4-formylpiperidine.

A solution of 1-(1,1-dimethylethyloxycarbonyl)-4-hydroxymethylpiperidine (20.7 g, 96.1 mmol) in dichloromethane (200 mL) was cooled to 0° C. and treated with pyridinium chlorochromate (31.1 g, 144.2 mmol). The suspension was allowed to warm to room temperature and stirred for 3 h. The mixture was then diluted with diethyl ether (250 mL), filtered through a pad of silica gel (50 mm×10 cm), and the solids washed with 4:1 hexane/acetone (3–250 mL). The filtrate was evaporated to leave a pale green oil. This oil was dissolved in ether (200 mL) and washed sequentially with 1N hydrochloric acid (2×100 mL), 1N aqueous sodium hydroxide (100 mL) and brine (100 mL). The aqueous washes were extracted with fresh diethyl ether (2×150 mL). The combined organic extract was dried over sodium sulfate, filtered and evaporated to afford the crude aldehyde (16.3 g, 76.42 mmol), which was used without purification.

$^1$H NMR (CDCl$_3$): δ 9.89 (s, 1H, CHO), 3.95 (m, 2H, eq-H-C(2)), 2.91 (m, 2H, ax-H-C(2)), 2.42 (m, 1H, H-C(4)), 1.95–1.50 (m, 4H, H-C(3)), 1.45 (s, 9H, (CH3)3C).

e. 1-(1-(1,1-Dimethylethyloxycarbonyl)-4-piperidinyl)-1-(3-pyridyl) methanol.

A solution of n-butyllithium (31.0 mL of a 2.5H solution in hexanes, 77.5 mmol) in tetrahydrofuran (80 mL) was cooled to −80° C. and treated dropwise with a solution of 3-bromopyridine (12.86 g, 81.4 mmol) in tetrahydrofuran (25 mL). The resulting green solution was stirred at −80° C. for 15 min, then was treated with a solution of 1(1,1-dimethylethyloxycarbonyl)-4-formylpiperidine (15.0 g, 70.3 in tetrahydrofuran (25 mL), added all at once. An immediate rise in the reaction temperature to ca. −50° C. was observed. The mixture was stirred at −70° C. for 45 min, then was quenched at −70° C. by addition of water (10 mL). The mixture was allowed to warm to room temperature, diluted with water (50 mL), and extracted with ethyl acetate (3×200 mL). The organic extracts were washed sequentially with 10% aqueous sodium hydroxide (100 mL) and brine (100 mL), combined, dried over sodium sulfate, filtered and evaporated to leave an amber oil (24.3 g). Purification of this oil by flash chromatography on silica gel (eluants: 2:1→1:2 hexane/acetone) afforded the title alcohol (R$_f$=0.07 (2:1 hexane/acetone)) as a white foam (9.65 g, 33.0 mmol, 47%).

$^1$H NMR (CDCl$_3$): δ 8.41 (m, 2H, H-C(2'), H-C(6')), 7.66 (ddd, J=1.4, 1.4, 8.3 Hz, H-C(4')), 7.27 (dd, J=5.1, 8.3 Hz, 1H, H-C(5')), 4.42 (d, J=7.1 Hz, CHOH), 4.09 (m, 2H, eq-H-C(2)), 2.59 (m, 2H, ax-H-C(2)), 1.95–1.65 (m, 3H, eq-H-C(3), H-C(4)), 1.43 (s, 9H, (CH3)3C), 1.20 (m, 2H, ax-H-C(3)). CIMS: m/z 294 ((M+H+1)$^+$, 13%), 293 ((M+H)$^+$, 63%), 265 (13), 238 (16), 237 (100), 175 (30).

f. 1-(1-(1,1-Dimethylethyloxycarbonylpiperidin-4-yl)-1-(3-pyridyl) methanol acetate.

A solution of 1-(1,1-dimethylethyloxycarbonylpiperidin-4-yl)-1-(3-pyridyl)methanol (900 mg, 3.08 mmol) in tetrahydrofuran (36 mL) was treated with acetic anhydride (1250 mg, 12.30 mmol), triethylamine (1560 mg, 15.40 mmol), and 4-dimethylaminopyridine (38 mg, 0.31 mmol). The resulting mixture was stirred at room temperature for 20 h. The mixture was concentrated on a rotary evaporator and the resulting residue was partitioned between dichloromethane and aqueous sodium hydroxide. The organic extract was separated and the aqueous was reextracted two more times with dichloromethane. The dichloromethane extracts were combined, dried over magnesium sulfate, filtered and concentrated on a rotary evaporator to give the crude product (1500 mg). Flash chromatography on silica gel (eluant: 25% acetone/hexanes) gave the title compound as a colorless glass (1030 mg, 3.08 mmol, 100%).

$^1$H-NMR (d$_6$-DMSO): δ 8.54–8.50(m, 2H), 7.75–7.71(d, J=8.0 Hz, 1H), 7.42–7.37(dd, J=4.8 Hz, J=7.8 Hz, 1H), 5.53–5.50(d, J=7.7 Hz, 1H), 3.98–3.88 (m, 2H), 2.63–2.50(br m, 2H), 2.08(s, 3H), 1.99–1.94(br m, 1H), 1.75–1.70 (m, 1H), 1.37(s, 9H), 1.22–1.06(m, 3H). CIMS: m/z 435 ((M+H)$^+$, 49%) 307 (10%) 280 (14%), 279 (100Z), 175 (66%).

g. 1-(1,1-Dimethylethyloxycarbonyl)-4-(3-pyridylmethyl)piperidine.

A solution of 1-(1-(1,1-dimethylethyloxycarbonylpiperidin-4-yl)-1-(3-pyridyl)methanol acetate (881 mg, 2.63 mmol) in methanol (32 mL) was treated with ammonium formate (881.mg) and 10% Pd/C. The resulting mixture was stirred at room temperature for 20 h. The mixture was filtered through celite and the cake was washed thoroughly with methanol. Concentration of the filtrates gave the crude product (920 mg). Flash chromatography on silica gel (eluant: 30% acetone/hexanes) gave the title compound as a clear glass (557 mg, 2.02 mmol, 77%).

$^1$H-NMR (d$_6$-DMSO): δ 8.41–8.40(m, 2H), 7.62–7.58(d, J=7.8 Hz, 1H), 7.33–7.29 (dd, J=4.9Hz, J=7.8Hz, 1H), 3.93–3.88(m, 2H), 2.63–2.53 m, 2H), 2.50(m, 2H), 1.70–1.50(m, 3H), 1.38(s, 9H), 1.10–0.97(m, 2H). CIMS: m/z 277 ((M+H)$^+$, 18%), 222 (14%), 221 (100%), 177 (12%).

h. 4-(3-Pyridylmethyl)piperidine.

A solution of 1-(1,1-dimethylethyloxycarbonyl)-4-(3-pyridylmethyl)piperidine (500 mg, 1.80 mmol) in chloroform (14 mL) was cooled to 0° C. and treated with trifluoroacetic acid (5 mL, 65.14 mmol). The resulting mixture was stirred for 1 h and then made basic by addition of aqueous sodium hydroxide. The organic extracts were separated and the aqueous was reextracted three more times with chloroform. The chloroform extracts were combined, dried over sodium sulfate, filtered and concentrated on a rotary evaporator to give the title compound as a colorless oil (300 mg, 1.70 mmol, 95%).

$^1$H-NMR (d$_6$-DMSO): δ 8.40–8.38 (m, 2H), 7.59–7.58 (d, J=7.8 Hz, 1H),7.32–7.28 dd, J=4.8 Hz, J=7.7 Hz, 1H), 2.89–2.86 (m, 2H), 2.5–2.48 (m, 2H), 2.40–2.33 (m, 2H), 1.58–1.44(m, 3H), 1.10–0.96(m, 2H).

EXAMPLE 55

1-((9S,10S)-2-Chloro-9,10-dihydro-9,10-methanoanthracen-9-ylmethyl)-4-(3-pyridylmethyl)piperidine.

Using a procedure similar to that described in Example 54 except starting with 1-((9S,10S)-2-chloro-9,10-dihydro-9,10-methanoanthracen-9-ylcarbonyl)-4 -(2-fluoro-3-pyridylmethyl)piperidine, the hydrochloride salt of the title compound was obtained as a white solid (540 mg, 1.20 mmol, 60%), mp 148°–156° C.

Analysis for C$_{27}$H$_{27}$ClN2.1.5HCl2.OH$_2$O: Calculated: C, 64.10; H, 6.48; N, 5.54 Found: C, 64.14; H, 6.46; N, 5.27

$^1$H-NMR (d$_6$-DMSO): δ 10.27 (br s, 1H), 8.77 (s, 1H), 8.73 (d, J=5.5 Hz, 1H), 8.28 (d, J=7.9 Hz, 1H), 7.87 (dd, J=5.5 Hz, J=7.9 Hz, 1H), 7.50 (m, 1H), 7.33–7.31 (m, 3H), 7.05–6.98 (m, 3H), 4.47 (s, 1H), 4.42–4.20 (m, 2H), 3.50–3.20 (m, 4H), 3.00–2.70 (m, 4H), 1.88–1.72 (m, 5H). CIMS: m/z 418 ((M+H+1)$^+$, $^{37}$Cl, 10%), 417 ((M+H)$^+$, $^{37}$Cl, 37%), 416 ((M+H+1)$^+$, $^{35}$Cl, 32%) 415 ((M+H)$^+$, $^{35}$Cl, 100%)

The starting amide was prepared as follows:

a. 1-((9S,10S)-2-Chloro-9,10-dihydro-9,10-methanoanthracen-9-ylcarbonyl)-4-(2 -fluoro-3-pyridylmethyl)piperidine.

Using a procedure similar to that described in Example 54a, except starting with (9S,10S)-2-chloro-9,10-dihydro-9,10-methanoanthracenecarboxylic acid, prepared as described in Example 11 and 4-(2-fluoro-3-pyridyl)piperidine, the title compound was obtained as a white solid (2.80 g, 6.28 mmol, 42%)

¹H-NMR (d₆-DMSO): δ 8.10–8.08 (m, 1H), 7.83–7.81 (m, 1H), 7.75–7.40 (br m, 1H), 7.36–7.27 (m, 4H), 7.01–6.99 (m, 3H), 4.65–4.55 (br m, 1H), 4.42 (s, 1H), 3.75–3.65 (br m, 1H), 3.00–2.65 (br m, 2H), 2.60–2.59 (m, 2H), 2.50 (m, 2H), 1.90–1.45 (br m, 3H), 1.25–1.10 (br m, 2H). CIMS: m/z 450 ((M+H+1)$^+$, $^{37}$Cl, 10%), 449 (M+H)$^+$, $^{37}$Cl, 37%), 448 ((M+H+1)$^+$, $^{35}$Cl, 33%), 447 ((M+H)$^+$, $^{35}$Cl, 100%), 291 (22%), 99 (13%).

The piperidine component was prepared as follows:

b. 1-(1-(1,1-Dimethylethyloxycarbonyl)-4-piperidyl)-1-(2-fluoro-3-pyridyl))methanol.

A solution of diisopropylamine (8.6 g, 85 mmol, freshly distilled) in tetrahydrofuran (81 mL) and hexanes (37 mL) was cooled to –78° C. and n-butyllithium (48.5 mL of a 1.6M solution in hexanes, 77 mmol) was added at a slow dropwise rate. The resulting solution was warmed to –20° C. over 20 min and then cooled again to –78° C. solution of 2-fluoropyridine (8.2 g, 85 mmol) in tetrahydrofuran (5 mL) was added dropwise over 30 min maintaining a temperature of less than –70° C. A yellow precipitate formed during this addition. The mixture was warmed to –50° C. and stirred for 30 min before cooling again to –78° C. A solution of 1-(1,1-dimethylethyloxycarbonyl)-4-formylpiperidine (15.0 g, 70 mmol), prepared as described in Example 55d, in tetrahydrofuran (15 mL) was added dropwise over 15 min maintaining a temperature of less than –70° C. The yellow solids dissolved leaving a orange solution. The solution was vigorously stirred while warming slowly to –20° C. over 1.5 h. The reaction mixture was quenched with glacial acetic acid (15 mL, pH<5) and partitioned between 1N aqueous sodium hydroxide (200 mL) and dichloromethane (500 mL, pH>12). The organic extract was separated and the aqueous was reextracted with methylene chloride (2×500 mL). The combined dichloromethane extracts were dried over sodium sulfate, filtered and concentrated on a rotary evaporator to give the crude as a tan oil (21 g). Flash chromatography on silica gel (eluant: 25% acetone/hexanes) gave the title compound as a colorless oil (15.2 g, 49 mmol, 70%).

¹M-NMR (d₆-DMSO): δ 8.14–8.12 (m, 1H), 7.99–7.93 (m, 1H), 7.39–7.35 (m, 1H), 5.53–5.52 (d, J=4.7 Hz, 1H), 4.57–4.54 (m, 1H), 3.93–3.90 (br m, 2H), 2.65–2.55 (br m, 2H), 1.75–1.60 (br m, 2H), 1.37 (s, 9H), 1.33–1.08 (br m, 3H). CIMS: m/z 521 (13%), 350 (12%), 311 ((M+H)$^+$, 28%), 256 (15%), 255 (100%), 237 (10%), 211 (46%), 193 (36%), 191 (13%).

c. 1-(1-(1,1-Dimethylethyloxycarbonyl)-4-piperidyl)-1-(2-fluoro-3-pyridyl))methanol acetate.

Using a procedure similar to that described in Example 54f, except starting with 1-(1-(1,1-dimethylethyloxycarbonyl)-4-piperidyl)-1-(2-fluoro-3 -pyridyl))methanol, the title compound was obtained as a colorless oil (14.4 g, 41 mmol, 85%).

¹H-NMR (d₆-DMSO): δ 8.21–8.19 (m, 1H), 7.98–7.91 (m, 1H), 7.42–7.37 (m, 1H), 5.59–5.57 (d, J=7.7 Hz, 1H), 3.98–3.89 (br m, 2H), 2.66–2.60 (br m, 2H), 2.07 (s, 3H), 2.07–1.97 (br m, 1H), 1.74–1.70 (m, 1H), 1.38 (s, 9H), 1.33–1.05 (m, 3H). CIMS: m/z 605 (15%), 297 253 (18%), 237 (18%), 194 (13%), 193 (100%).

d. 1-(1,1-Dimethylethyloxycarbonyl)-4-(2-fluoro-3-pyridylmethyl)piperidine.

Using a procedure similar to that described in Example 54g, except starting with 1-(1-(1,1-dimethylethyloxycarbonyl)-4-piperidyl)-1-(2-fluoro-3-pyridyl))methanol acetate, the title compound was obtained as a colorless oil (7.5 g, 25.5 mmol, 87%).

¹H-NMR (d₆-DMSO): δ 8.10–8.08 (m, 1H), 7.86–7.79 (m, 1H), 7.32–7.27 (m, 1H), 3.93–3.88 (m, 2H), 2.70–2.60 (br m, 2H), 2.56–2.52 (m, 2H), 1.75–1.65 (br m, 1H), 1.59–1.45 (m, 2H), 1.39 (s, 9H), 1.12–0.98 (m, 2H).

e. 4-(2-Fluoro-3-pyridylmethyl)piperidine.

Using a procedure similar to that described in Example 54h, except starting with 1-(1,1-dimethylethyloxycarbonyl)-4-(2-fluoro-3-pyridylmethyl)piperidine, the title compound was obtained as a tan solid (6.3 g, 32.5 mmol, 127%).

¹H-NMR (d₆-DMSO): δ 8.11–8.09 (d, J=4.8 Hz, 1H), 7.88–7.81 (m, 1H), 7.34–7.29 (m, 1H), 3.75–3.30 (br m, 1H exchangable), 3.18–3.14 (m, 2H), 2.76–2.67 (m, 2H), 2.58–2.55 (d, J=7.1 Hz, 2H), 1.81–1.73 (m, 1H), 1.66–1.59 (m, 2H), 1.34–1.20 (m, 2H). CIMS: m/z 196 ((M+H+1)$^+$, 13%), 195 ((M+H)$^+$, 100%) 175 (31%).

EXAMPLE 56

1-((9R,10R)-2-Chloro-9,10-dihydro-9,10-methanoanthracen-9-ylmethyl)-4-(3-pyridylmethyl)piperidine.

Using a procedure similar to that described in Example 54, except starting with 1-((9R,10R)-2-chloro-9,10-dihydro-9,10-methanoanthracen-9-ylcarbonyl)-4 -(3-pyridylmethyl)piperidine, the hydrochloride salt of the title compound was obtained as a white solid (227 mg, 0.50 mmol, 53%), mp 165°–170° C.

Analysis for C₂₇H₂₇ClN2.5HCl.1.25H₂O: Calculated: C, 65.90; H, 6.35; N, 5.69 Found: C, 65.89; H, 6.28; N, 5.47 ¹H-NMR (d₆-DMSO): δ 10.15 (br s, 1H), 8.65 (br s, 2H), 8.06 (d, J=7.5 Hz, 1H), 7.70 (m, 1H), 7.49 (s, 1H), 7.34–7.31(m, 3H), 7.03–6.96 (m, 3H), 4.47 (s, 1H), 4.36–4.27 (m, 2H), 3.60–3.10 (br m, 4H), 3.00–2.50 (m 4H), 2.00–1.50 (m, 5H). CIMS: m/z 418 (M+H+1)$^+$, 37Cl, 10%), 417 ((M+H)$^+$, 37Cl, 37%), 416 ((M+H+1)$^+$, 35Cl, 32%) 415 ((M+H) $^+$, 35Cl, 100%).

The starting amide was prepared as follows:

a. 1-((9R,10R)-2-Chloro-9,10-dihydro-9,10-methanoanthracen-9-ylcarbon yl)-4-(3-pyridylmethyl)piperidine.

Using a procedure similar to that described in Example 54a, except starting with (9R,10R)-2-chloro-9,10-dihydro-9,10-methanoanthracenecarboxylic acid, prepared as described in Example 2a, and 2-fluoropyridylpiperidine, prepared as described in Example 56e, the title compound was obtained as a white solid (850 mg, 1.90 mmol, 52%).

¹H-NMR (d₆-DMSO): δ 8.10–8.08 (d, J=4.5 Hz, 1H), 7.85–7.81 (m, 1H), 7.75–7.35 (br m, 1H), 7.36–7.28 (m, 4H), 7.01–7.00 (m, 3H), 4.70–4.60 (br m, 1H), 4.42 (s, 1H), 3.00–2.50 (br m, 6H), 1.90–1.75 (br m, 1H), 1.75–1.50 (br m, 2H), 1.25–1.00 (br m, 2H).

EXAMPLE 57

1-((9S,10S)-2-Chloro-9,10-dihydro-9,10-methanoanthracen-9-ylmethyl)-4-(2-dimethylsulfamoyl-5-methoxyphenylmethyl)piperidine.

Using a procedure similar to that described in Example 55, except starting with 1-((9S,10S)-2-chloro-9,10-dihydro-9,10-methanoanthracen-9-ylcarbonyl)-4 -(2-dimethylsulfamoyl-5-methoxyphenyl-methyl)piperidine, the hydrochloride salt of the title compound was obtained as a white solid (450 mg, 0.77 mmol, 87%), mp 242°–245° C.

Analysis for C₃₁H₃₅ClN2O3S.HCl.0.5H₂O: Calculated: C, 62.40; H, 6.25; N, 4.70 Found: C, 62.39; H, 6.11; N, 4.56 ¹H-NMR (d₆-DMSO): δ 7:74(d, J=8.6 Hz. 1H), 7.47(s, 1H), 7.36–7.32(m, H), 7.06–6.99(m, 5H), 4.47(s, 1H), 4.40–4.20(m, 2H), 3.85(s, 3H), 3.50–3.10(br m, 4H), 3.05–2.80(m, 2H), 2.72(s, 2H), 2.69–2.64(m, 6H), 2.00(br m, 1H), 1.66(br m, 4H). CIMS: m/z 554 ((M+H+1)⁺, 37Cl 13%), 553 ((M+H)⁺, 37Cl 41%) 552 ((M+H+1)⁺, 35Cl, 34%), 551 ((M+H)⁺, 35Cl, 100%), 549 (11%).

The starting amide was prepared as follows:

a. 1-((9S,10S)-2-Chloro-9,10-dihydro-9,10-methanoanthracen-9-ylcarbonyl)-4-(2-dimethylsulfamoyl-5-methoxyphenylmethyl)piperidine.

Using a procedure similar to that described in Example 55a, except starting with 9S,10S-2-chloro-9,10-dihydro-9,10-methanoanthracenecarboxylic acid, prepared as described in Example 11, and 4-(2-dimethylsulfamoyl-5-methoxyphenylmethyl)piperidine, the title compound was obtained as a colorless oil (630 mg, 1.11 mmol, 58%). 1H-NMR (d₆-DMSO): δ 7.75–7.72 (d, J=8.7 Hz, 1H), 7.70–7.30 (m, 4H), 7.02–6.97 (m, 5H), 4.65–4.55 (br m, 1H), 4.42 (s, 1H), 3.83 (s, 3H), 3.80–3.75 (br m, 1H), 3.00–2.60 (br m, 6H), 2.50 (m, 2H), 2.00–1.90 (br m, 1H), 1.70–1.60 (br m, 1H), 1.35–1.20 (br m, 1H). CIMS: m/z 593 (15%), 568 ((M+H+1)⁺, 37Cl, 13%), 567 ((M+H)⁺, 37Cl, 43%), 566 ((M+H+1)⁺, 35Cl, 36%), 565 ((M+H)⁺, 35Cl, 100%).

The piperidine was prepared as follows:

b. 1-(1-(1,1-Dimethylethyloxycarbonyl)-4-piperidinyl)-1-(2-dimethylsulfamoyl-5-methoxyphenyl)methanol.

A solution of n-butyllithium (7.1 mL, 1.6M in hexanes) in tetrahydrofuran (40 mL) was cooled to −70° C. A solution of N,N-dimethyl-4-methoxy-benzenesulfonamide (2.67 g, 12.4 mmol) in tetrahydrofuran (30 mL) was added and the mixture was stirred at −20° C. to −5° C. for 2 h. The mixture was cooled to −70° C. and a solution of 1-(1,1-dimethylethyloxycarbonyl)-4-formylpiperidine, prepared as described in Example 55e, (3.0 g, 14.0 mmol) in tetrahydrofuran (30 mL) was added dropwise maintaining a temperature of less than −70° C. The mixture was allowed to warm to room temperature slowly over 2 h. The mixture was partitioned between aqueous sodium hydroxide and dichloromethane. The organic extract was separated and the aqueous reextracted two more times with dichloromethane. The combined dichloromethane extracts were dried over sodium sulfate, filtered and concentrated on a rotary evaporator to give the crude as a tan oil (7 g). Flash chromatography on silica gel (eluant: 1% methanol/methylene chloride) gave the title compound as a colorless oil (2.8 g, 8.17 mmol, 58%). ¹H-NMR (d₆DDMSO): δ 7.71–7.68 (d, J=8.9 Hz, 1H), 7.23 (m, 1H), 7.00 (m, 1H), 5.36 (m, 1H), 5.10 (m, 1H, exchangable), 4.05–3.95 (br m, 4H), 3.84 (s, 3H), 2.63 (s, 6H), 1.80–1.70 (br m, 1H), 1.65–1.50 (br m, 2H), 1.38 (s, 9H), 1.35–1.10 (br m, 2 H). CIMS: m/z 383 (11%), 373 (30%), 357 (11%), 356 (10%), 355 (49%), 330 (13%), 329 (74%), 327 (15%), 312 (18%), 311 (100%).

c. 1-(1-(1,1-Dimethylethyloxycarbonyl)-4-piperidinyl)-1-(2-dimethylsulfamoyl-5-methoxyphenyl)methanol acetate.

Using a procedure similar to that described in Example 55e, except starting with 1-(1-(1,1-dimethylethyloxycarbonyl)-4-piperidinyl)-1-(2-dimethylsulfamoyl-5-methoxyphenyl)methanol, the title compound was obtained as a colorless oil (2.1 g, 4.46 mmol, 69%). 1H-NMR (d₆-DMSO): δ 7.78–7.75 (d, J=8.9 Hz, 1H), 7.11–7.08 (dd, J=2.6 Hz, J=8.9 Hz, 1H), 7.01–7.00 (d, J=2.6 Hz, 1H), 6.35–6.33 (d, 4.4 Hz, 1H), 4.10–3.95 (br m, 2H), 3.86 (s, 3H), 2.66 (m, 9H), 2.10 (s, 3H), 2.00–1.90 (br m, 1H), 1.50–1.25 (m, 12H). CIMS: m/z 416 (15%), 415 (69%), 383 (21%), 371 (31%), 369 (16%), 356 (14%), 355 (67%), 313 (16%), 312 (21%), 311 (100%).

d. 1-(1,1-Dimethylethyloxycarbonyl)-4-(2-dimethylsulfamoyl-5-methoxyphenylmethyl)piperidine.

Using a procedure similar to that described in Example 55d, except starting with 1-(1-(1,1-Dimethylethyloxycarbonyl)-4-piperidinyl)-1-(2-dimethylsulfamoyl-5-methoxyphenyl)methanol acetate, the title compound was obtained as a colorless oil (1.6 g, 3.89 mmol, 91%). ¹H-NMR (d₆-DMSO): δ 7.74–7.71 (d, J=8.5 Hz, 1H), 7.00–6.95 (m, 2H), 4.00–3.90 (br m, 2H), 3.84 (s, 3H), 2.83–2.81 (d, J=7.1 Hz, 2H), 2.63 (m, 8H), 1.80–1.65 (br m, 1H), 1.55–1.45 (br m, 2H), 1.39 (s, 9H), 1.20–1.00 (br m, 2H).

e. 4-(2-Dimethylsulfamoyl-5-methoxyphenylmethyl)piperidine.

Using a procedure similar to that described in Example 55e, except starting with 1-(1,1-dimethylethyloxycarbonyl)-4-(2-dimethylsulfamoyl-5-methoxyphenylmethyl)piperidine, the title compound was obtained as a colorless oil (1.2 g, 3.87 mmol, 100%). ¹H-NMR (d₆-DMSO): δ 7.74–7.70 (m, 1H), 7.00–6.92 (m, 2H), 3.83 (s, 3H), 3.55–3.25 (br m, 1H, exchangable), 3.00–2.70 (m, 4H), 2.63 (s, 6H), 2.50 (m, 2H), 1.80–1.70 (br m, 1H), 1.55–1.50 (br m, 2H), 1.30–1 15 (br m, 2H) CIMS: m/z 314 ((M+H+1)⁺, 11%), 313 ((M+H)⁺, 100%), 311 (12%), 268 (10%).

EXAMPLE 58

1-((9R,10R)-2-Chloro-9,10-dihydro-9,10-methanoanthracen-9-ylmethyl)-4(2-dimethylsulfamoyl-5-methoxyphenylmethyl)piperidine.

Using a procedure similar to that described in Example 55, except starting with 1-((9S,10S)-2-chloro-9,10-dihydro-9,10-methanoanthracen-9-ylcarbonyl)-4-(2-dimethylsulfamoyl-5-methoxyphenylmethyl)piperidine, the hydrochloride salt of the title compound was obtained as a white solid (365 mg, 0.62 mmol, 58%), mp 201°–204° C.

Analysis for C₃₁H₃₅ClN₂O3S.HCl.H₂O: Calculated: C, 61.50; H, 6.32; N, 4.63 Found: C, 61.52; H, 6.13; N, 4.56 ¹H-NMR (d₆-DMSO): δ 9.9 (br s, 0.5H, exchangable), 7.74 (d, J=8.7 Hz, 1H), 7.48 (s, 1H), 7.34–7.32 (m, 3H), 7.03–6.99 (m, 5H), 4.47(s, 1H), 4.40–4.20 (m, 2H), 3.85 (s, 3H), 3.50–3.10 (br m, 4H), 3.05–2.80 (m, 2H), 2.74(s, 2H), 2.69–2.64 (m, 6H), 2.00 (br m, 1H), 1.70 (br m, 4H) CIMS: m/z 554 ((M+H+1)⁺, 37Cl, 10%), 553 ((M+H)⁺, 37Cl, 34%), 552 ((M+H+1)⁺, 35Cl, 33%), 551 ((M+H)⁺, 35Cl, 100%), 549 (10%).

The starting amide was prepared as follows:

a. 1-((9S,10S)-2-Chloro-9,10-dihydro-9,10-methanoanthracen-9-ylcarbonyl)-4-(2-dimethylsulfamoyl-5-methoxyphenylmethyl)piperidine.

Using a procedure similar to that described in Example 55a, except starting with (9R,10R)-2-chloro-9,10-dihydro-9,10-methanoanthracenecarboxylic acid, prepared as described in Example 2a, and 4-(2-dimethylsulfamoyl-5-methoxyphenylmethyl) piperidine, prepared as described in Example 58e, the title compound was obtained as a white solid (617 mg, 1.09 mmol, 57%)
¹H-NMR (d₆-DMSO): δ 7.75–7.72 (d, J=8.5 Hz, 1H), 7.70–7.30 (m, 4H), 7.02–6.97 (m, 5H), 4.70–4.55 (br m, 1H), 4.42 (s, 1H), 3.83 (s, 3H), 3.82–3.75 (br m, 1H), 3.00–2.70 (br m, 6H), 2.64 (s, 6H), 2.50 (m, 2H), 2.00–1.90 (br m, 1H), 1.75–1.20 (br m, 4H). CIMS: m/z 568 ((M+H+1)⁺, 37Cl 11%) 567 ((M+H)⁺, 37Cl 35%), 566 ((M+H+1)⁺, 35Cl, 33%), 565 ((M+H)⁺, 35Cl, 100%).

EXAMPLE 59

(R,S)-1-[1-(9,10-Dihydro-9,10-methanoanthracen-9-ylmethyl)-4-piperidyl]-1-cyclohexylmethanol.

Using a procedure similar to that described in Example 40, except using cyclohexylmagnesium chloride and the piperidine aldehyde prepared as described in Example 6a, the title compound was isolated as a white powder, mp 180°–182° C.

Analysis for $C_{28}H_{35}NO \cdot HCl \cdot 0.5H_2O$: Calculated: C, 75.23; H, 8.34; N, 3.13 Found: C, 74.95; H, 8.06; N, 3.03
$^1$H NMR (d$_6$-DMSO+TFA-d): δ 7.35 (m, 4H), 4.46 (s, 1H, M-C(10)), 4.34 (s, 2H, CH2N), 3.60 (m, 2H, eq-H-C(2')), 3.29 (m, 2H, ax-H-C(2')), 2.95 (brs, 1H, CHOH), 2.73 (s, 2H, H-C(11)), 1.86–1.00 (m, 16H). CIMS: m/z 403 ((M+H+1)$^+$, 30%), 402 ((M+H)$^+$, 100), 401 (28), 400 (38), 385 (15), 384 (14).

EXAMPLE 60

2-[1-(9,10-Dihydro-9,10-methanoanthracen-9-ylmethyl)-4-piperidyl]-2-propanol.

A solution of ethyl (1-(9,10-dihydro-9,10-methanoanthracen-9-ylmethyl)-4-piperidine carboxylate (430 mg, 1.19 mmol) in tetrahydrofuran (9 mL) was cooled to −78° C. and treated dropwise with methylmagnesium chloride (1.0 mL of a 3.0M solution in ether, 3.0 mmol). The mixture was stirred at −78° C. for 20 min, then was warmed to room temperature. After 1 h at room temperature, an additional quantity (0.3 mL, 1.0 mmol) of methylmagnesium chloride was added, and the mixture was stirred at room temperature for an additional 0.5 h. The mixture was then poured into 1N aqueous sodium hydroxide (20 mL) and extracted with chloroform (2×20 mL). The organic extracts were washed with brine (20 mL), combined, dried over potassium carbonate, filtered and evaporated to leave an amber gum. Purification by flash chromatography over silica gel (eluant: 98:2 chloroform/methanol) gave a white powder, which upon treatment with ethereal hydrogen chloride gave the hydrochloride salt of the title compound (170 mg, 0.45 mmol, 37%) as a white powder, mp 289°–290° C.

Analysis for $C_{24}H_{29}NO \cdot HCl \cdot 0.1H_2O$: Calculated: C, 74.74; H, 7.89; N, 3.63 Found: C, 74.73; H, 7.79; N, 3.58
$^1$H NMR (d$_6$-DMSO+TFA-d): δ 7.35 (m, 4H), 7.00 (m, 4H), 4.46 (s, 1H, H-C(10)), 4.34 (s, 2H, CH2N), 3.63 (m, 2H, eq-H-C(2')), 3.25 (m, 2H, ax-H-C(2')), 2.72 (s, 2H, H-C(11)), 1.77 (m, 5H, H-C(3'), H-C(4')), 1.07 (s, 6H (CH3)2C) CIMS: m/z 349 ((M+H+1)$^+$, 30%) 348 ((M+H)$^+$, 100).

The starting ester was prepared as follows:
a. Ethyl 4-(1-(9,10-dihydro-9,10-methanoanthracen-9-ylmethyl)-4-piperidine carboxylate.

A solution of 9,10-dihydro-9,10-methanoanthracene-9carboxaldehyde (1.00 g, 4.54 mmol) and ethyl isonipecotate (1.07 g, 6.81 mmol) in methanol was treated with glacial acetic acid until the solution had a pH~5. Crushed 3 angstrom sieves (1.0 g) were added, and the mixture was stirred at room temperature for 2 h. Sodium cyanoborohydride (630 mg, 10.03 mmol) was then added, and the mixture was stirred at room temperature for 18 h. After this time, additional quantities of sodium cyanoborohydride (100 mg) and 3 angstrom sieves (1.0 g, crushed) were added, and the mixture was stirred an additional 6 h. The solids were removed by filtration and washed with chloroform (3×25 mL). The filtrate was washed sequentially with 10% aqueous sodium hydroxide (2×30 mL) and brine (30 mL). The aqueous washes were extracted with chloroform (2×50 mL). The organic extracts were combined, dried over potassium carbonate, filtered and evaporated to leave a dark semi-solid mass (1.4 g). Purification by flash chromatography over silica gel (eluant: 99.5:0.5 chloroform/methanol) afforded the title compound as a light yellow solid (800 mg, 2.21 mmol, 49%).

$^1$H NMR (d$_6$-DMSO): δ 7.28 (m, 2H), 7.18 (m, 2H), 6.90 (m, 4H), 4.30 (s, 1H, H-C(10)), 4.04 (q, J=7.1 Hz, 2H, CO2CH2CH3), 2.94 (m, 2H, eq-H-C(2')), 2.45 (s, 2H, H-C(11)), 2.34–2.22 (m, 3H, ax-H-C(2'), H-C(4')), 1.78–1.50 (m, 4H, H-C(3')), 1.16 (t, 3H, CO2CH2CH3).

EXAMPLE 61

(S*)-1-[1-((9S, 10S)-2-Chloro-9,10-dihydro-9,10-methanoanthracen-9-ylmethyl)-4-piperidyl]-1-(3-pyridyl)ethanol.

Using a procedure similar to that described in Example 50, except using (S*)-1-(4-piperidyl)-1-(3-pyridyl)ethanol in the amide formation step, the title compound was obtained as a white solid, mp 8°7–93° C. α$_F$=+32.7° (c=1.04, CHCl3).

Analysis for $C_{28}H_{29}ClN_2O$: Calculated: C, 75.57; H, 6.56; N, 6.29 Found: C, 75.54; H, 6.91; N, 5.97
$^1$H NMR (d$_6$-DMSO+TFA-d): δ 8.91 (m, 2H, H-C(2"), H-C(6")), 8.67 (d, J=8.3 Hz, 1H, H-C(4")), 8.12 (dd, J= 5.8, 8.3 Hz, 1H, H-C(5")), 7.47 (d, J=1.8 Hz, 1H, B-C(1)), 7.33 (m, 3H), 7.02 (m, 3H), 4.47 (s, 1H, H-C(10), 4.35 (qAB, JAB=14.4 Hz, 2H, CH2N), 3.67, 3.50 (2d, J=11.5 Hz, 2H, eq-H-C(2')), 3.17 (m, 2H, ax-H-C(2')), 2.69 (brd, J= 1.8 Hz, 2H, H-C(11)), 1.95 (m, 2H, eq-H-C(3')), 1.68 (m, 1H, H-C(4')), 1.59 (s, 3H, CH3), 1.35 (m, 2H, ax-H-C(3')). CIMS: m/z 447 ((M+H)$^+$, $^{37}$Cl, 36%), 446 ((M+H+1)$^+$, $^{35}$Cl, 33), 445 ((M+H)$^+$, $^{35}$Cl 100), 427 (17).

EXAMPLE 62

1-((9S,10S)-2-Chloro-9,10-dihydro-9,10-methanoanthracen-9-ylmethyl)-4-(2-hydroxy-3-pyridylmethyl)piperidine.

A solution of 1-((9S,10S)-2-chloro-9,10-dihydro-9,10-methanoanthracen-9-ylcarbonyl)-4-(2-methoxy-3-pyridylmethyl)piperidine (1.80 g. 3.92 mmol) in tetrahydroruran (50 mL) was treated with boron trifluoride etherate (612 mg, 4.31 mmol) and borane-tetrahydrofuran (14.9 mL of a 1.0H solution, 14.9 mmol). The resulting solution was heated to reflux for 3 h. The mixture was then concentrated on a rotary evaporator to give a colorless residue. The residue was dissolved in concentrated hydrochloric acid (50 mL, 12N) and heated to reflux for 3 h. The solution was concentrated to dryness on a rotary evaporator to give a glassy residue. This residue was dissolved in methanol (100 mL) and concentrated to dryness on a rotary evaporator (3X) to give a white foam. This foam was dissolved in methanol (5 mL) and added to rapidly stirred diethyl ether (200 mL) to give a white precipitate which was collected and washed with diethyl ether to give the hydrochloride salt of the title compound (1.3 g, 2.60 mmol, as an off-white powder, mp 211°–215° C.

Analysis for $C_{27}H_{27}ClN_2O \cdot 1.9HCl$: Calculated: C, 64.8; H, 5.82; N, 5.60 Found: C, 64.8; H, 5.80; N, 5.48
$^1$H-NMR (d$_6$-DMSO): δ 11.57 (br s, 1H, exchangable), 10.00–9.75 (br m, 1H, exchangable), 7.52–7.48 (m, 1H), 7.34–7.24 (m, 5H), 7.05–6.99 (m, 3H), 6.15–6.09 (m, 1H), 4.47 (s, 1H), 4.40–4.24 (m, 2H), 3.50–3.18 (br m, 4H), 2.74 (s, 2H), 2.56–2.30 (m, 2H), 1.89–1.58 (br m, 5H).
CIMS: m/z 434 ((M+H+1)$^+$, $^{37}$Cl, 13%) 433 ((M+H)$^+$, $^{37}$Cl, 41%) 432 ((M+H+1)$^+$, $^{35}$Cl, 32%) 431 ((M+H)$^+$, $^{35}$Cl, 100%) 430 (11%)

The starting amide was prepared as follows:
a. 1-((9S,10S)-2-Chloro-9,10-dihydro-9,10-methanoanthracen-9-ylcarbonyl)-4-(2-methoxy-3-pyridylmethyl)piperidine To a solution of 1-((9S,10S)-2-chloro-9,10-dihydro-9,10-methanoanthracen-9-ylcarbonyl)-4-(2-fluoro-3-pyridylmethyl)piperidine, (2.60 g, 5.8 mmol), prepared as described in Example 55a, in methanol (25 mL) was added potassium fluoride (4.15 g, 71.4 mmol) which caused a slight exotherm (~35° C.). Sodium methoxide solution in methanol (4.4 mL of a 25 wt % solution) was added which caused another exotherm (~50° C.) and thinned the suspension. This suspension was heated to reflux for 6 h. Additional potassium fluoride (4.15 g, 71.4 mmol) was added and the suspension was refluxed for 18 h. Additional sodium methoxide solution (1.0 mL) was added and the suspension was refluxed for 5 h. The mixture was cooled to room temperature, partitioned between basic brine and dichloromethane. The organic extract was separated and the aqueous was extracted with dichloromethane (2X). The dichloromethane extracts were combined, dried over sodium sulfate, filtered and concentrated on a rotary evaporator. The crude foam was purified by flash chromatography on silica (eluant: 15% acetone/hexanes) to give the title compound as a white solid (1.82 g, 3.95 mmol, 68%).

$^1$H-NMR (d$_6$-DMSO): δ 8.03–8.01 (m, 1H), 7.65 (br s, 1H), 7.51–7.30 (m, 4H), 7.02–6.89 (m, 4H), 4.60 (br m, 1H), 4.41 (s, 1H), 3.86 (s, 3H), 3.68 (br m, 1H), 3.00–2.45 (br m, 5H), 2.00–1.10 (br m, 5H).

CIMS: m/z 462 ((M+H+1)$^+$, $^{37}$Cl, 11%), 461 ((M+H)$^+$, $^{37}$Cl, 37%), 460 ((M+H+1)$^+$, $^{35}$Cl, 33%), 459 ((M+H)$^+$, $^{35}$Cl 100%).

EXAMPLE 63

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
|---|---|
| (a) Tablet |  |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule |  |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

FORMULAE

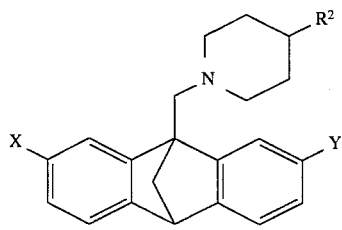

I

-continued
FORMULAE

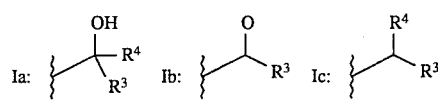

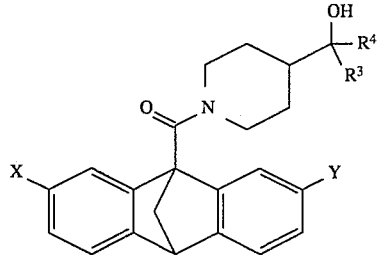

II

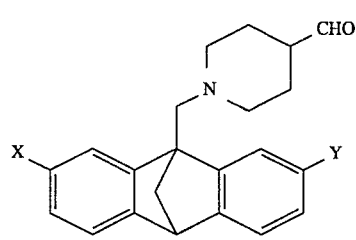

III

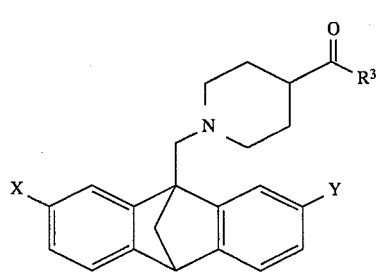

IV

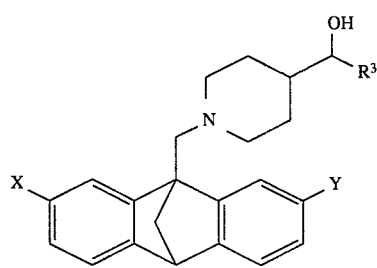

V

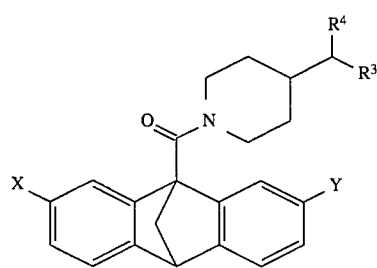

VI

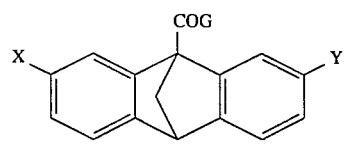

VII

57
-continued
FORMULAE
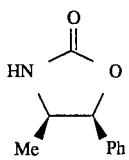
Scheme I
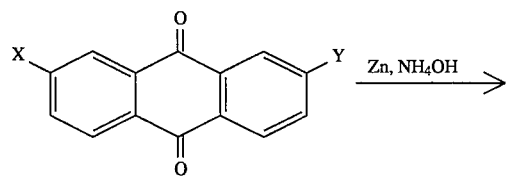
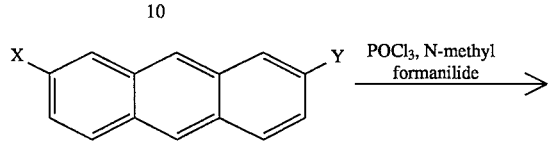
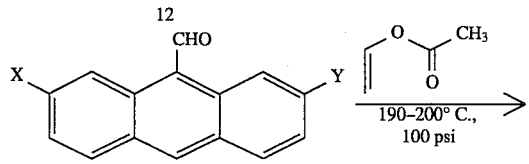
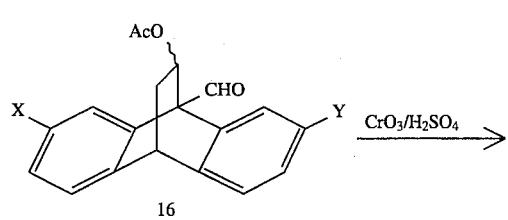
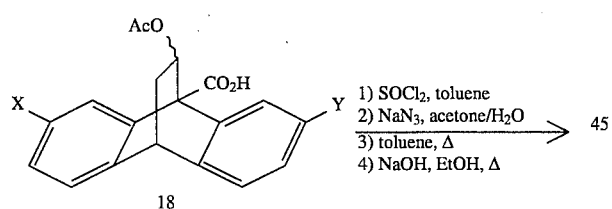
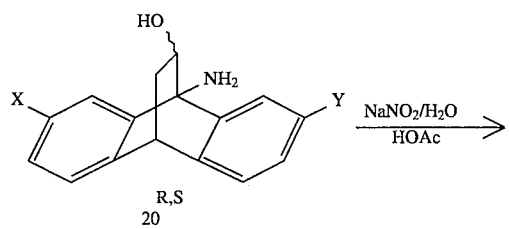
58
-continued
Scheme I
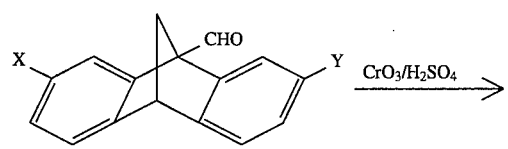
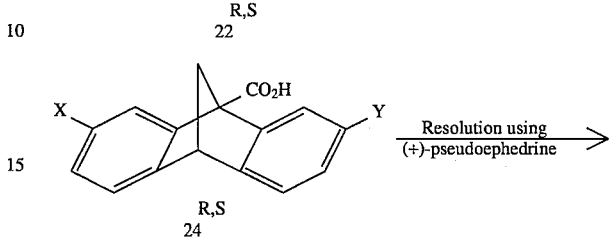
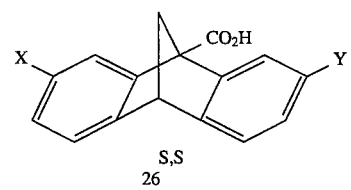
Scheme IIa
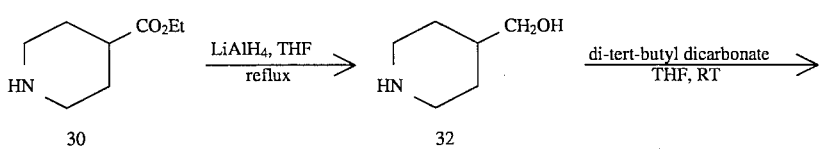

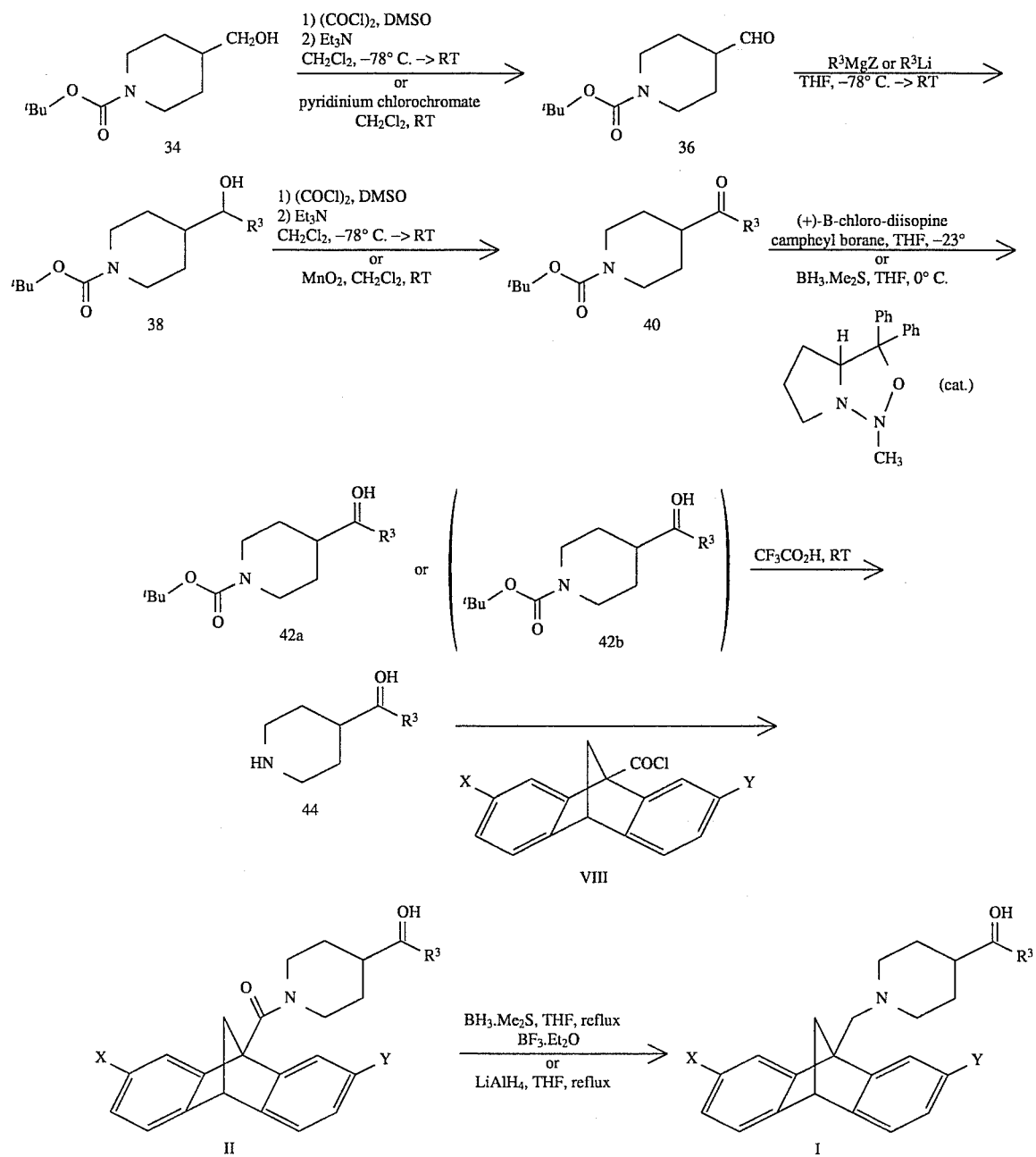
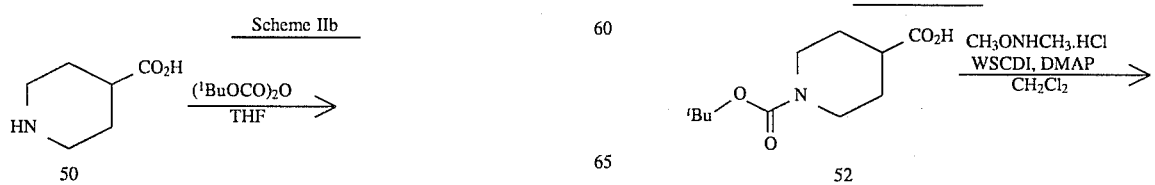

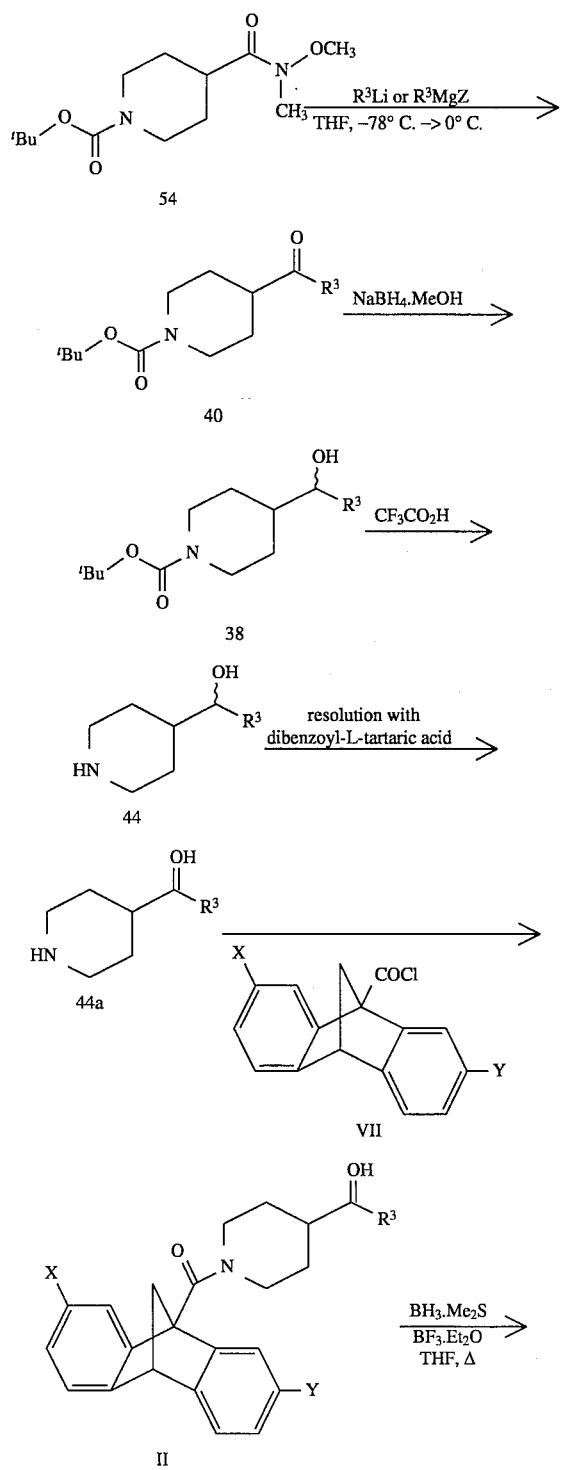

63
-continued
Scheme IIc
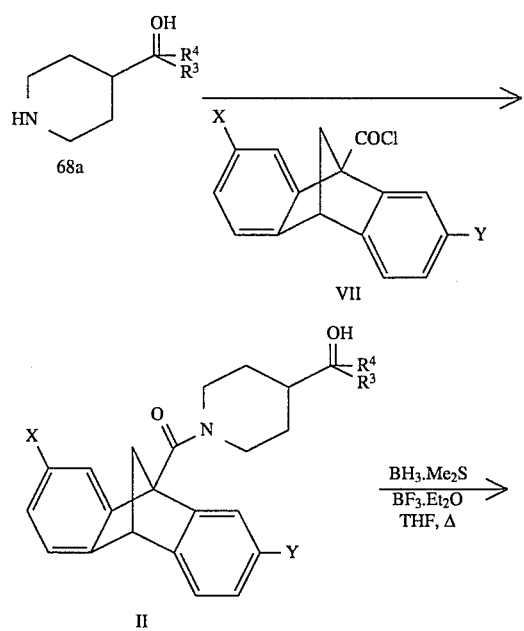
64
-continued
Scheme III
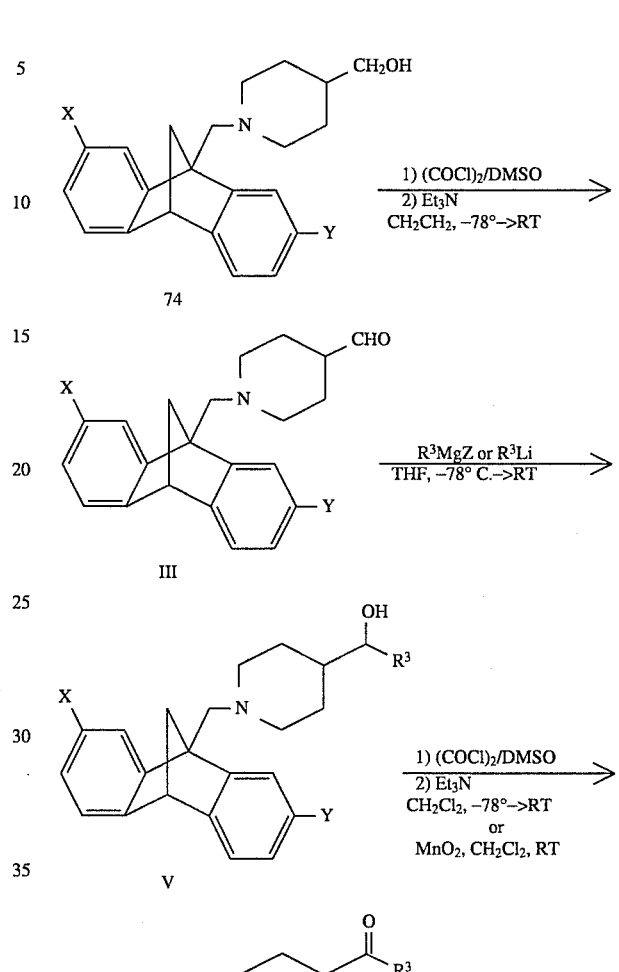
Scheme III
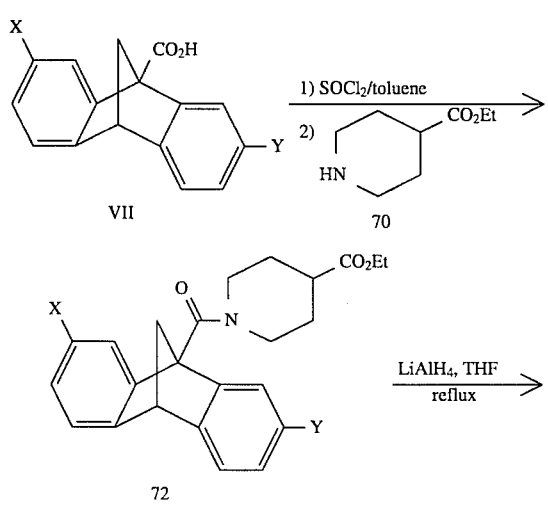
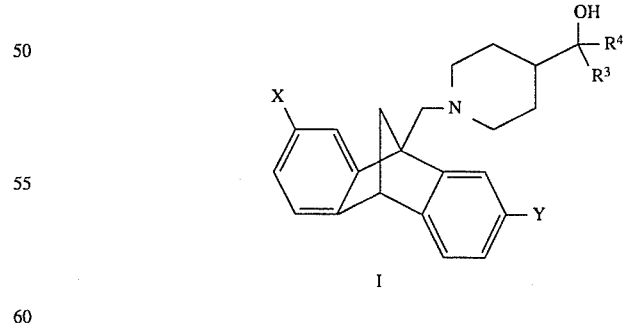

Scheme IV

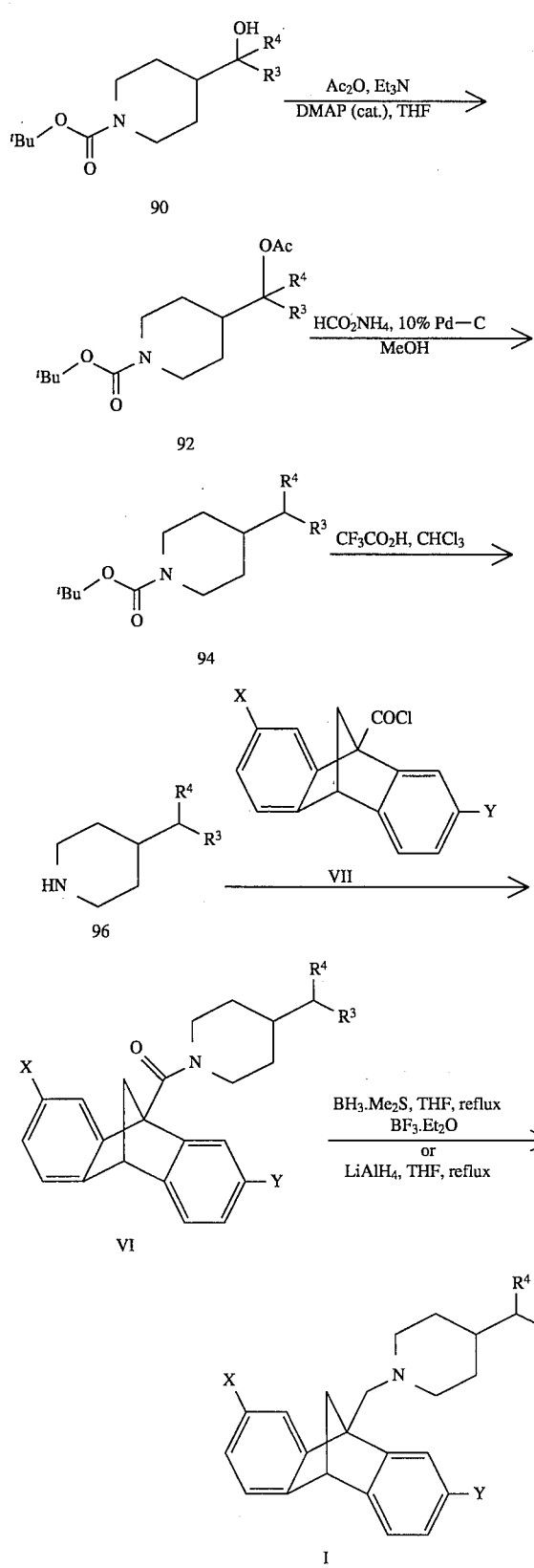

What is claimed is:

1. A compound of formula I

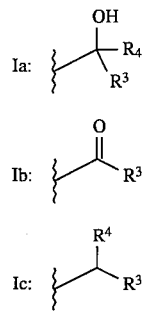

or a pharmaceutically acceptable salt thereof, wherein
X and Y are independently selected from hydrogen and halo; and
$R^2$ is selected from the structures shown as formulae Ia, Ib, and Ic, Ia: $\begin{array}{c} OH \\ {-}R_4 \\ R^3 \end{array}$ Ib: $\begin{array}{c} O \\ \| \\ {-}R^3 \end{array}$ Ic: $\begin{array}{c} R^4 \\ {-}R^3 \end{array}$ wherein:
$R^3$ is selected from
(3–6C)cycloalkyl;
phenyl and naphthyl each of which may bear 0–3 substituents independently selected from the group consisting of (1–6C)alkyl, (1–6C)alkoxy, hydroxy, halo, cyano, nitro, benzoyl, di(1–6C)alkylamino(1–6C)alkyl, aminosulfonyl having the formula $SO_2NR^aR^b$ and aminocarbonyl having the formula $CONR^cR^d$ wherein $R^a$, $R^b$, $R^c$ and $R^d$ are independently selected from hydrogen and (1–6C)alkyl, or wherein $R^a$ and $R^b$, and $R^c$ and $R^d$, together with the nitrogen atom to which each is attached, form a 5-membered or 6-membered heterocyclic ring in which the said nitrogen is the only heteroatom; or
a isothiazolyl, oxazolyl, thiazolyl, oxadiazolyl, furyl, imidazolyl, thienyl or benzimidazolyl ring, which may bear 0–2 substituents selected from hydroxy, (1–6C)alkyl, (1–6C)alkoxy, (1–6C)hydroxyalkyl, phenyl, chloro, and fluoro; and
$R^4$ is selected from hydrogen and (1–6C)alkyl.

2. A pharmaceutical composition comprising a compound of formula I,

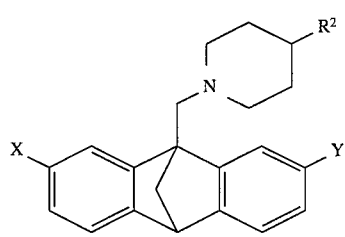

or a pharmaceutically acceptable salt thereof, wherein
X and Y are independently selected from hydrogen and halo; and $R^2$ is selected from the structures shown as formulae Ia, Ib, and Ic,

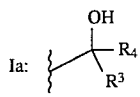

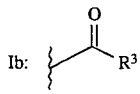

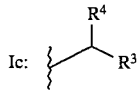

wherein:

$R^3$ is selected from (3–6C)cycloalkyl;

phenyl and naphthyl each of which may bear 0–3 substituents independently selected from the group consisting of (1–6C)alkyl, (1–6C)alkoxy, hydroxy, halo, cyano, nitro, benzoyl, di(1–6C)alkylamino(1–6C)alkyl, aminosulfonyl having the formula $SO_2NR^aR^b$ and aminocarbonyl having the formula $CONR^cR^d$ wherein $R^a$, $R^b$, $R^c$ and $R^d$ are independently selected from hydrogen and (1–6C)alkyl, or wherein $R^a$ and $R^b$, and $R^c$ and $R^d$, together with the nitrogen atom to which each is attached, form a 5-membered or 6-membered heterocyclic ring in which the said nitrogen is the only heteroatom; or a isothiazolyl, oxazolyl, thiazolyl, oxadiazolyl, furyl, imidazolyl, thienyl or benzimidazolyl ring, which may bear 0–2 substituents selected from hydroxy, (1–6C)alkyl, (1–6C)alkoxy, (1–6C)hydroxyalkyl, phenyl, chloro, and fluoro; and $R^4$ is selected from hydrogen and (1–6C)alkyl.

3. A method of treating psychoses comprising administering to a patient in need of such treatment an effective amount of a compound of formula I,

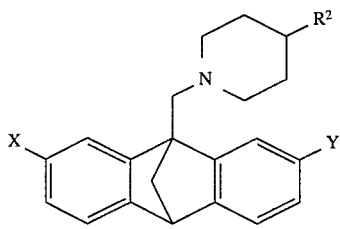

or a pharmaceutically acceptable salt thereof, wherein

X and Y are independently selected from hydrogen and halo; and $R^2$ is selected from the structures shown as formulae Ia, Ib, and Ic,

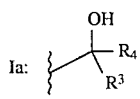

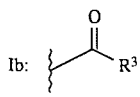

-continued

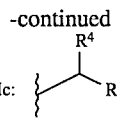

wherein:

$R^3$ is selected from (3–6C)cycloalkyl;

phenyl and naphthyl each of which may bear 0–3 substituents independently selected from the group consisting of (1–6C)alkyl, (1–6C)alkoxy, hydroxy, halo, cyano, nitro, benzoyl, di(1–6C)alkylamino(1–6C)alkyl, aminosulfonyl having the formula $SO_2NR^aR^b$ and aminocarbonyl having the formula $CONR^cR^d$ wherein $R^a$, $R^b$, $R^c$ and $R^d$ are independently selected from hydrogen and (1–6C)alkyl, or wherein $R^a$ and $R^b$, and $R^c$ and $R^d$, together with the nitrogen atom to which each is attached, form a 5-membered or 6-membered heterocyclic ring in which the said nitrogen is the only heteroatom; or a isothiazolyl, oxazolyl, thiazolyl, oxadiazolyl, furyl, imidazolyl, thienyl or benzimidazolyl ring, which may bear 0–2 substituents selected from hydroxy, (1–6C)alkyl, (1–6C)alkoxy, (1–6C)hydroxyalkyl, phenyl, chloro, and fluoro; and $R^4$ is selected from hydrogen and (1–6C)alkyl.

4. A compound of formula II,

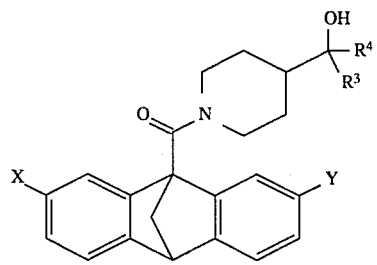

wherein:

X and Y are independently selected from hydrogen and halo;

$R^3$ is selected from (3–6C) cycloalkyl;

(1–6C)alkyl;

phenyl and naphthyl each of which may bear 0–3 substituents independently selected from the group consisting of (1–6C)alkyl, (1–6C)alkoxy, hydroxy, halo, cyano, nitro, benzoyl, di(1–6C)alkylamino (1–6C) alkyl, aminosulfonyl having the formula $SO_2NR^aR^b$ and aminocarbonyl having the formula $CONR^cR^d$ wherein $R^a$, $R^b$, $R^c$ and $R^d$ are independently selected from hydrogen and (1–6C)alkyl, or wherein $R^a$ and $R^b$, and $R^c$ and $R^d$, together with the nitrogen atom to which each is attached, form a 5-membered or 6-membered heterocyclic ring in which the said nitrogen is the only heteroatom; or a isothiazolyl, oxazolyl, thiazolyl, oxadiazolyl, furyl, imidazolyl, thienyl or benzimidazolyl ring, which may bear 0–2 substituents selected from hydroxy, (1–6C)alkyl, (1–6C)alkoxy, (1–6C)hydroxyalkyl, phenyl, chloro, and fluoro; and $R^4$ is selected from hydrogen and (1–6C)alkyl.

5. A compound of formula V,

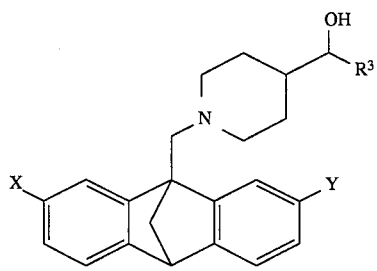

wherein:
X and Y are independently selected from hydrogen and halo; and

R$^3$ is selected from (3–6C)cycloalkyl;

(1–6C)alkyl;

phenyl and naphthyl each of which may bear 0–3 substituents independently selected from the group consisting of (1–6C)alkyl, (1–6C)alkoxy, hydroxy, halo, cyano, nitro, benzoyl, di(1–6C)alkylamino (1–6C)alkyl, aminosulfonyl having the formula SO$_2$NR$^a$R$^b$ and aminocarbonyl having the formula CONR$^c$R$^d$ wherein R$^a$, R$^b$, R$^c$ and R$^d$ are independently selected from hydrogen and (1–6C)alkyl, or wherein R$^a$ and R$^b$, and R$^c$ and R$^d$, together with the nitrogen atom to which each is attached, form a 5-membered or 6-membered heterocyclic ring in which the said nitrogen is the only heteroatom; or a isothiazolyl, oxazolyl, thiazolyl, oxadiazolyl, furyl, imidazolyl, thienyl or benzimidazolyl ring, which may bear 0–2 substituents selected from hydroxy, (1–6C)alkyl, (1–6C)alkoxy, (1–6C)hydroxyalkyl, phenyl, chloro, and fluoro.

6. A compound of formula VI,

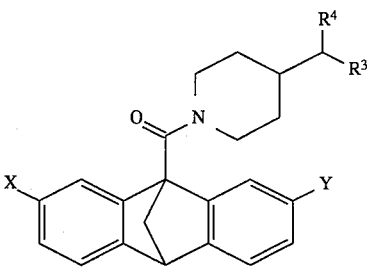

wherein:
X and Y are independently selected from hydrogen and halo;
R$^3$ is selected from (3–6C)cycloalkyl;

(1–6C)alkyl;

phenyl and naphthyl each of which may bear 0–3 substituents independently selected from the group consisting of (1–6C)alkyl, (1–6C)alkoxy, hydroxy, halo, cyano, nitro, benzoyl, di(1–6C)alkylamino (1–6C)alkyl, aminosulfonyl having the formula SO$_2$NR$^a$R$^b$ and aminocarbonyl having the formula CONR$^c$R$^d$ wherein R$^a$, R$^b$, R$^c$ and R$^d$ are independently selected from hydrogen and (1–6C)alkyl, or wherein R$^a$ and R$^b$, and R$^c$ and R$^d$, together with the nitrogen atom to which each is attached, form a 5-membered or 6-membered heterocyclic ring in which the said nitrogen is the only heteroatom; or a isothiazolyl, oxazolyl, thiazolyl, oxadiazolyl, furyl, imidazolyl, thienyl or benzimidazolyl ring, which may bear 0–2 substituents selected from hydroxy, (1–6C)alkyl, (1–6C)alkoxy, (1–6C)hydroxyalkyl, phenyl, chloro, and fluoro; and R$^4$ is selected from hydrogen and (1–6C)alkyl.

* * * * *